US011788114B2

(12) United States Patent
Talebpour et al.

(10) Patent No.: US 11,788,114 B2
(45) Date of Patent: *Oct. 17, 2023

(54) METHODS AND DEVICES FOR ELECTRICAL SAMPLE PREPARATION

(71) Applicant: QVELLA CORPORATION, Richmond Hill (CA)

(72) Inventors: Samad Talebpour, Richmond Hill (CA); Aye Aye Khine, Thornhill (CA); Robert Maaskant, King City (CA); Tino Alavie, Thornhill (CA)

(73) Assignee: QVELLA CORPORATION, Richmond Hill (CA)

( * ) Notice: Subject to any disclaimer, the term of this patent is extended or adjusted under 35 U.S.C. 154(b) by 842 days.

This patent is subject to a terminal disclaimer.

(21) Appl. No.: 16/510,253

(22) Filed: Jul. 12, 2019

(65) Prior Publication Data
US 2020/0102596 A1 Apr. 2, 2020

Related U.S. Application Data

(63) Continuation of application No. 15/401,291, filed on Jan. 9, 2017, now Pat. No. 10,378,043, which is a
(Continued)

(51) Int. Cl.
*C12M 1/42* (2006.01)
*C12M 1/00* (2006.01)
(Continued)

(52) U.S. Cl.
CPC ...... *C12Q 1/6806* (2013.01); *B01L 3/502715* (2013.01); *B01L 3/502738* (2013.01);
(Continued)

(58) Field of Classification Search
CPC ......... B01L 3/502715; B01L 3/502738; B01L 7/52; B01L 2300/0645; B01L 2300/0681;
(Continued)

(56) References Cited

U.S. PATENT DOCUMENTS 6,174,675 B1 * 1/2001 Chow ..................... B01L 7/52
435/6.19
9,574,245 B2 * 2/2017 Talebpour ......... B01L 3/502738
(Continued)

OTHER PUBLICATIONS

Stark, The Use of a Microelectroporatorto Study Poration of Jurkat Cells, pp. 1-79 (Year: 2009).*

*Primary Examiner* — Matthew D Krcha
*Assistant Examiner* — Austin Q Le
(74) *Attorney, Agent, or Firm* — Hill & Schumacher

(57) ABSTRACT

Devices and methods are provided for electrically lysing cells and releasing macromolecules from the cells. A microfluidic device is provided that includes a planar channel having a thickness on a submillimeter scale, and including electrodes on its upper and lower inner surfaces. After filling the channel with a liquid, such that the channel contains cells within the liquid, a series of voltage pulses of alternating polarity are applied between the channel electrodes, where the amplitude of the voltage pulses and a pulse width of the voltage pulses are effective for causing irreversible electroporation of the cells. The channel is configured to possess thermal properties such that the application of the voltage produces a rapid temperature rise as a result of Joule heating for releasing the macromolecules from the electroplated cells. The channel may also include an internal filter for capturing and concentrating the cells prior to electrical processing.

13 Claims, 41 Drawing Sheets
Specification includes a Sequence Listing.

Related U.S. Application Data continuation of application No. 13/750,723, filed on Jan. 25, 2013, now Pat. No. 9,574,245, which is a continuation-in-part of application No. PCT/CA2012/000698, filed on Jul. 25, 2012.

(60) Provisional application No. 61/586,906, filed on Jan. 16, 2012, provisional application No. 61/511,201, filed on Jul. 25, 2011.

(51) Int. Cl.

| | | |
|---|---|---|
| *C12N 1/06* | (2006.01) | |
| *C12N 1/08* | (2006.01) | |
| *C12N 13/00* | (2006.01) | |
| *C12Q 1/6806* | (2018.01) | |
| *C12Q 3/00* | (2006.01) | |
| *C12Q 1/686* | (2018.01) | |
| *B01L 3/00* | (2006.01) | |
| *B01L 7/00* | (2006.01) | |

(52) U.S. Cl.
CPC ........... *B01L 3/502753* (2013.01); *B01L 7/52* (2013.01); *C12M 35/02* (2013.01); *C12M 47/06* (2013.01); *C12N 1/066* (2013.01); *C12N 1/08* (2013.01); *C12N 13/00* (2013.01); *C12Q 1/686* (2013.01); *C12Q 3/00* (2013.01); *B01L 2200/0631* (2013.01); *B01L 2200/143* (2013.01); *B01L 2300/0645* (2013.01); *B01L 2300/0681* (2013.01); *B01L 2300/087* (2013.01); *B01L 2300/0809* (2013.01); *B01L 2300/0858* (2013.01); *B01L 2300/0874* (2013.01); *B01L 2300/0887* (2013.01); *B01L 2300/14* (2013.01); *B01L 2300/1833* (2013.01); *B01L 2400/0694* (2013.01)

(58) Field of Classification Search
CPC ..... B01L 2300/0809; B01L 2300/0819; B01L 2300/0858; B01L 2300/087; B01L 2300/0887; B01L 2300/1833; B01L 2400/0424; C12M 35/02; C12M 47/06; C12Q 1/6806; C12Q 1/686; G01N 27/02; G01N 27/04; G01N 27/045; G01N 27/046; G01N 27/06; G01N 27/221; G01N 27/26; G01N 27/447

See application file for complete search history.

(56) References Cited

U.S. PATENT DOCUMENTS

| | | | |
|---|---|---|---|
| 2007/0178529 A1* | 8/2007 | Breidford | F16K 15/1825 435/7.1 |
| 2011/0062025 A1* | 3/2011 | Albrecht | G01N 27/44795 204/644 |

* cited by examiner without plasmid with purified plasmid control with purified plasmid
from Glass Bead lysis with purified plasmid
from E-lysis

| Condition | Pulse train duration (ms) | Peak current (A) | Peak maximum sample temperature (°C, estimate) | Peak average sample temperature (°C, estimate) |
|---|---|---|---|---|
| 1 | 6.2 | 3.7 | 55 | 50 |
| 2 | 9.5 | 4.1 | 75 | 67 |
| 3 | 12 | 3.0 | 93 | 82 |
| 4 | 20 | 7.4 | 164 | 140 |

Figure 23

| Lysis condition | $C_T$ value |
|---|---|
| Condition 1 | 28 |
| Condition 2 | 26 |
| Condition 3 | 25 |
| Condition 4 | 24 |
| GB lysis | 23 |

| Lysis condition | $C_T$ value |
|---|---|
| Condition 1 | 28 |
| Condition 2 | 28 |
| Condition 3 | 25 |
| Condition 4 | 24 |
| No Control | 21 |

| C.albicans Samples/Controls | Fluorescence intensity |
|---|---|
| Buffer negative control | 115 |
| Buffer negative control | 107 |
| Open | 137 |
| Open | 145 |
| Closed | 170 |
| Closed | 175 |
| GB lysis | 161 | dom
METHODS AND DEVICES FOR ELECTRICAL SAMPLE PREPARATION

CROSS-REFERENCE TO RELATED APPLICATION

This application is a continuation of U.S. patent application Ser. No. 13/750,723, titled "METHODS AND DEVICES FOR ELECTRICAL SAMPLE PREPARATION" and filed on Jul. 25, 2013, which is a continuation-in-part of PCT Application No. PCT/CA2012/000698, titled "METHODS AND DEVICES FOR ELECTRICAL SAMPLE PREPARATION" and filed on Jul. 25, 2012, and claims priority to U.S. Provisional Application No. 61/511,201, titled "METHODS AND DEVICES FOR ELECTRICAL SAMPLE PREPARATION" and filed on Jul. 25, 2011, and U.S. Provisional Application No. 61/586,906, titled "METHODS AND DEVICES FOR ELECTRICAL SAMPLE PREPARATION" and filed on Jan. 16 2012, the entire contents of which are all incorporated herein by reference.

BACKGROUND

This disclosure relates to methods of preparation and processing of biological samples. More particularly, the disclosure relates to the processing of biological samples to be used for performing diagnostic assays and for therapeutic uses.

Despite unprecedented progress in measurement techniques over the recent years, satisfactory noninvasive measurements of target analytes in biological samples are still not possible in most cases. Generally, one or more sample pretreatment steps are necessary. These steps are referred to as sample preparation, the goal of which is to render a raw sample suitable for a measurement with a satisfactory signal to noise ratio. The sample preparation is accomplished by proceeding through cleanup, enrichment or concentration, and medium balance steps. In addition, in the case of measuring cellular contents, the molecules of interest must be released to the medium via cell lysis. Frequently, a lysate treatment step, involving various reagents, is needed to make the lysate assay-ready by modifying the target and non-target molecules or adjusting the lysate composition. Sample preparation is often the bottleneck in the measurement process, as it tends to be slow and generally involves multiple reagents and manual steps that require substantial time, complexity and cost.

The complexity of sample preparation can be better appreciated by referring to a typical example in which pathogenic bacteria in human urine are identified through rRNA hybridization where a specific sequence on the 16S rRNA is hybridized with a labeled complementary nucleic acid probe. An exemplary sample preparation protocol employs the foretold five steps as follows: 1) relatively large particles, such as crystals, and excess ions are removed (cleanup); 2) the bacteria count per unit volume is increased by reducing the water (liquid) content (enrichment); 3) the ribosomes are released by lysing the cells (lysis); 4) the lysate is treated such that the rRNA is partially untangled from the accompanying proteins and its conformation is modified to better expose the target region to the probes (lysate treatment); and 5) the chemical and ionic composition of the lysate is adjusted to support hybridization (medium balance).

In some instances, the sample preparation is further complicated by the need to process the sample with various reagents. For example, reagents may be needed for lysis, binding and elution, precipitation, removal or inhibition of interferants and/or contaminants, denaturing of DNA to obtain single stranded DNA, separation of rRNA from ribosomal proteins, and denaturing of enzymes or other proteins such as DNAse and RNAse. One example of a reagent treatment for the purification of nucleic acids involves cell lysis and molecular denaturation by a chaotropic agent (guanidinium thiocyanate) followed by nucleic acid extraction by phenol-chloroform liquid-liquid separation, which is a complex method involving very hazardous reagents. Further, sample processing by reagents may involve additional steps such as heating and bead milling, for example, to enhance the function and effectiveness of reagents.

SUMMARY

Devices and methods are provided for electrically lysing cells and releasing macromolecules from the cells. A microfluidic device is provided that includes a planar channel having a thickness on a submillimeter scale, and including electrodes on its upper and lower inner surfaces. After filling the channel with a liquid, such that the channel contains cells within the liquid, a series of voltage pulses of alternating polarity are applied between the channel electrodes, where the amplitude of the voltage pulses and a pulse width of the voltage pulses are effective for causing irreversible electroporation of the cells. The channel is configured to possess thermal properties such that the application of the voltage produces a rapid temperature rise as a result of Joule heating for releasing the macromolecules from the electroporated cells. The channel may also include an internal filter for capturing and concentrating the cells prior to electrical processing and removal of cellular debris from the cell lysate after electrical processing.

Accordingly, in a first embodiment, there is provided a method of electrically processing a liquid within a microfluidic device to release macromolecules from at least one cell within the liquid;

the microfluidic device including:
an upper planar substrate formed from a thermally insulating material;
a lower planar substrate formed from a thermally insulating material; and
a side wall having a thickness on a submillimeter scale, wherein said upper planar substrate, said lower planar substrate and said side wall define a channel;
an upper electrode provided on an inner surface of said upper planar substrate; and
a lower electrode provided on an inner surface of said lower planar substrate;

the method including:
flowing the liquid into the channel;
applying bipolar voltage pulses between the upper electrode and the lower electrode and electrically heating the liquid to an elevated temperature between approximately 30 degrees Celsius and 250 degrees Celsius;
wherein the voltage pulses are applied such that the liquid is heated faster than a timescale of thermal diffusion from the channel; and
wherein the voltage pulses are applied such that a rate of change of the temperature of the liquid is sufficient to effect lysis of the at least one cell.

In another aspect, there is provided a microfluidic device for processing a liquid to release macromolecules from at least one cell within the liquid, the microfluidic device comprising:

an upper planar substrate formed from a thermally insulating material;

a lower planar substrate formed from a thermally insulating material; and a side wall having a thickness on a submillimeter scale, wherein said upper planar substrate, said lower planar substrate and said side wall define a channel;

an upper electrode provided on an inner surface of said upper planar substrate; and a lower electrode provided on an inner surface of said lower planar substrate;

a first port in flow communication with a first side of said channel;

a second port in flow communication with a second side of said channel; and a voltage controller configured to:

apply bipolar voltage pulses between the upper electrode and the lower electrode and electrically heat the liquid to an elevated temperature between approximately 30 degrees Celsius and 250 degrees Celsius; and apply the voltage pulses such that the liquid is heated faster than a timescale of thermal diffusion from the channel, and such that a rate of change of the temperature of the liquid is sufficient to effect lysis of the at least one cell.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which:

FIG. 4(B) shows a schematic plan view of the electrical sample processing device of FIG. 4a.

FIG. 5(B) shows an approximation to the equivalent circuit in FIG. 5a.

FIG. 23 lists the electrical and corresponding thermal conditions for the lysis of fungal cells used to demonstrate the dependence of the lysis efficiency on the electrical channel temperature.

DETAILED DESCRIPTION

Figure 1:
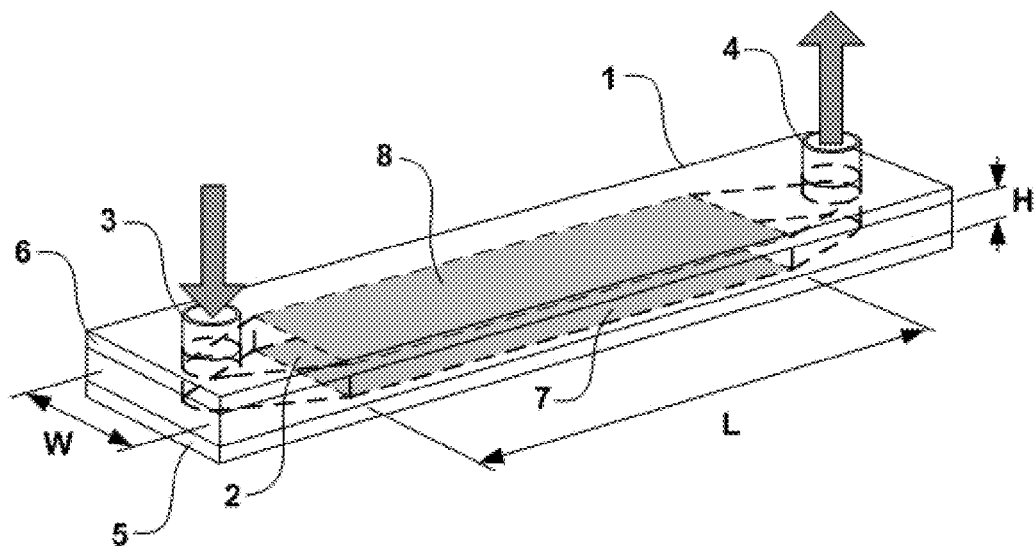
FIG. 1 shows a schematic of an electrical sample processing device.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure. It should be understood that the order of the steps of the methods disclosed herein is immaterial so long as the methods remain operable. Moreover, two or more steps may be conducted simultaneously or in a different order than recited herein unless otherwise specified As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately", when used in conjunction with ranges of dimensions of particles, compositions of mixtures or other physical properties or characteristics, are meant to cover slight variations that may exist in the upper and lower limits of the ranges of dimensions so as to not exclude embodiments where on average most of the dimensions are satisfied but where statistically dimensions may exist outside this region. It is not the intention to exclude embodiments such as these from the present disclosure.

In selected embodiments disclosed below, methods and devices are provided for subjecting a sample to electrical lysis of cells and/or the electrical treatment of molecular species within the sample. Methods disclosed below involve subjecting a liquid sample to an amplitude modulated electrical pulse train in a confined fluidic channel for the cell lysis and/or treatment of macromolecules. The pulse train generates a pulsed electric field across the thickness of the channel and responsively generates heat within the channel, where the thickness is small compared to at least one other dimension of the channel. The channel may be closed or open during the application of the voltage pulses, as further described below.

In selected embodiments in which the sample may or may not include cells, an electric field is applied as a series of pulses whereby macromolecules within the sample are treated or processed. Without intending to be limited by theory, it is believed that as the voltage pulse train acts on the liquid within the channel, appreciable ion current is established. This causes the liquid medium (generally, an aqueous medium) to be rapidly heated by Joule heating, thereby providing an electrical treatment mechanism to macromolecules within the liquid medium. The maximum temperature depends on the timescale of the electric pulse train, the applied voltage, the ionic strength of the liquid, the electrical and thermal characteristics of the channel and the pressure regulation of the channel.

The channel temperature may be maintained at the desired temperature for a period, termed herein as the residence time, by passive feedback through conductivity change arising from liquid-gas phase transition, or active feedback through current measurements.

Due to the large surface to volume ratio of the liquid confined in the channel, and the thermal properties of the channel (described in further detail below), and the sub-second duration of the pulse train, the heating and cooling of the liquid is rapid. In the context of the present disclosure, this process of heating and cooling in sub-second time scale is referred to as "flash heating". In some embodiments, the heating rate is faster than a timescale for thermal diffusion.

In one embodiment, in which the liquid sample provided within the channel includes cells, the application of the electric pulses causes the cells to undergo irreversible electroporation. The mechanism of irreversible electroporation of microorganisms is not completely elucidated in the literature. It has been postulated that when a pulse with high enough intensity is applied to the cell suspension, such that a voltage higher than 1 V is established across the cell membrane, pores are generated in the membrane. The process is known as electroporation. When the number of pulses and/or pulse-width is large enough, the cell membrane will be ruptured, permanently compromising the integrity of the cell membrane. This process is known as irreversible electroporation, which is accompanied by the release of some intracellular contents from the cell. In general, the electric field intensity required to achieve the irreversible electroporation of microorganisms is greater than about 10 kV/cm. For example, many microorganisms can be subjected to irreversible electroporation for electric fields within the range of approximately 12-45 kV/cm. The action of such an intense electric field in the suspension medium is accompanied by appreciable ion currents, which for the device disclosed herein increases the temperature of the medium via Joule heating. This may increase the efficacy of irreversible electroporation, lowering the threshold of irreversible electroporation and contributing to cell membrane/wall damage as the heating has a significant influence on cell membrane fluidity and stability.

Without wanting to be limited by theory, it is believed that the effects of irreversible electroporation and heat induced cell disintegration act together to enhance the release of cellular contents. The combined process by which desired macromolecules are released from cells will be henceforth referred to as "electrical lysis".

In the case of microorganisms with protective cell walls in addition to the cell membrane, the influence of irreversible electroporation alone may be insufficient for releasing some of the cellular contents of interest when not aided by this heating. The heating may be responsible for disintegration of the cell wall to the extent that it enables release of higher molecular weight cellular contents.

Without being bound to any theory, it is believed that the intense electric field may cause structural modification in macromolecules, such as proteins, due to a modification of the balance of forces that maintains their native structures. The alterations in conformation may disengage the chemically reactive functional groups on a macromolecule and render it incapable of performing its catalytic or other designated functions. However, macromolecules are generally more resistant to electric fields than comparatively larger microorganisms. Excess heat acting for a period of up to 100 ms, can cause excessive thermal fluctuation of structure and can deprive some of the macromolecules of their functionality. Generally speaking, flash heating and the intense electric field contribute to the electrical treatment mechanism described herein, which causes macromolecular species within the liquid to experience irreversible conformation changes. In selected embodiments, the electrical treatment method described above is employed such that the sample (such as a lysate for example) is rendered more suitable for downstream applications such as diagnostic assays. The electrical lysis of cells and subsequent electrical treatment of the lysate is, either singly or in combination, termed electrical processing throughout this disclosure.

As further described below, the ionic strength of the sample may be selected to be below a maximal value in order to support the establishment of an effective electric field with a suitable timescale for effecting electrical processing. The specific maximal value or range of suitable values of the ionic strength will mainly depend on the capability of the applied voltage source to deliver high voltage along with the corresponding current over the timescale over which the processing is desired to occur. It is to be understood that those skilled in the art may perform routine experimentation in order to determine a suitable upper limit or range of values for the ionic strength in a given application. Since both electrical lysis and electrical treatment are performed according to selected embodiments in a medium with low ionic strength and in the absence of additional reagents, a post lysis medium balance step, generally required in traditional sample preparation methods, may not be necessary. In other applications, the ionic strength suitable for a subsequent step can be easily altered by adding an appropriate concentration of ions to the processed sample or lysate.

In some embodiments, additional sample processing steps such as sample cleanup and sample concentration may be readily incorporated into the device, potentially without adding significant complexity or cost to the device or the manufacturing process. Examples of the incorporation of such additional processing steps are described in further detail below. Accordingly, selected embodiments provided herein include devices and methods that enable the direct and rapid processing of samples without requiring additional reagents and additional processing steps.

In selected embodiments, devices and methods are provided for preparation of samples containing microorganisms, such as, but not limited to, blood, urine or a growth medium, for diagnostic assays. The device, which may be provided in the form of a disposable cartridge, can be optionally interfaced to reaction chambers where the target molecules undergo a detection or identification process.

Referring now to FIG. 1, an example embodiment of a device for performing electrical sample processing is provided. FIG. 1 shows an example configuration of the device 1, while more details are provided by the schematic cross section of shown in FIG. 2. The device has a thin channel 2 (where the thickness of the channel is small compared to lateral dimensions of the channel) which is defined on one side by the base plate 5, insulating layer 9 and electrode 7 and on the opposite side by top plate 6, insulating layer 10 and electrode 8. The upper and lower portions are separated by a thin spacer, in which material is removed to form the channel cavity. Typically, the spacer is made of a dielectric material which may be slightly deformable under an applied clamping pressure, or which is bonded to the upper and lower surfaces of the channel cavity. The spacer thus defines the side walls of the channel, provides the fluid seal, and electrically insulates the top and bottom electrodes from each other.

In alternative embodiments, the device need not include a separate spacer, and side walls defining the lateral portions of the channel may be formed, at least in part, within a substrate, such that the substrate includes a recessed portion having a bottom surface and lateral side walls adapted to form at least a portion of the channel.

The lower electrode 7 and upper electrode 8 are electrically isolated from the base and top plates (substrates) by lower and upper electrically insulating layers, 9 and 10. In an alternative embodiment, one or both of the upper and lower plates are nonconductive and the electrical insulating layer may be omitted. In accordance with thermal requirements, thermal insulating layers may also be provided which may be separate from or be at least a portion of the electrical insulating material.

The channel includes an inlet port 3 through which fluid sample and other fluids may be introduced and which may be in fluid communication with upstream chambers where pre-filtering may optionally be performed and which may include chambers where fluids are stored. The device is also equipped with an outlet port 4 that may be in fluid communication with a collecting apparatus or chamber, such as a waste chamber or downstream assay reaction chamber. Flow along the channel is provided by a pressure differential between inlet and outlet ports. The device may include additional fluid features, such as valves for opening and closing ports 3 and 4.

The channel has dimensions H×W×L which, in one example implementation, may be on the order of 0.1×5×10 mm³, but which may be greater or lesser in accordance with operational requirements. Two electrodes 7 and 8 are intended for inducing an electric field across the channel.

The microfluidic channel has a thickness on a submillimeter (i.e. micron) scale. An example range for the channel thickness is 5 µm<H<1000 µm. In some embodiments, a suitable channel thickness for obtaining effective electrical lysis and treatment with practical voltage sources (for example, in the 10-200 V range) may be between approximately 50 µm and 500 µm. The channel length and width may be selected to provide a suitable channel volume and optionally a suitable flow rate through the channel. Without excluding the use of the methods and devices described herein for microfluidic applications in which the channel length and width are also on a submillimeter scale, more typical example ranges for the length and width of the channel are approximately 1 mm<W<10 mm and 5 mm<L<50 mm.

In one example implementation, one or more of the first and second electrodes may be provided as metal coatings that are deposited on electrically insulating layers provided on the upper and lower channel surfaces. Example thicknesses for the deposited electrode include 1 nm<h<1 µm, although thicker layers may also be realized.

In another example, one or more of the first and second electrodes may be provided as metal foils, for which material properties and dimensions are chosen in accordance with electrical and thermal requirements. Example thicknesses for the metal foil include 10 µm<h<500 µm, or 20 µm<h<200 µm.

In embodiments intended for samples which contain cells or viruses, collectively referred to here as cells, the channel may be operated to concentrate the cells prior to electrical lysis. Applying a time dependent unipolar voltage on the electrodes, an electric field is established in the channel, which exerts an effective force on charged cells and carries them to a thin region at the immediate vicinity of the anodic electrode while the excess fluid is carried out of the outlet port. For improved retention of the cells, the anodic electrode may be coated with capture ligands specific to a class of cells that are desired to be retained. As the cells, concentrated at the lower extremity of the channel, slowly move over the electrode, they specifically bind or hybridize with their corresponding capture ligands. This mode of sample concentration has been disclosed in co-pending patent PCT Application Number WO/2011/014946A1.

Figure 3A:
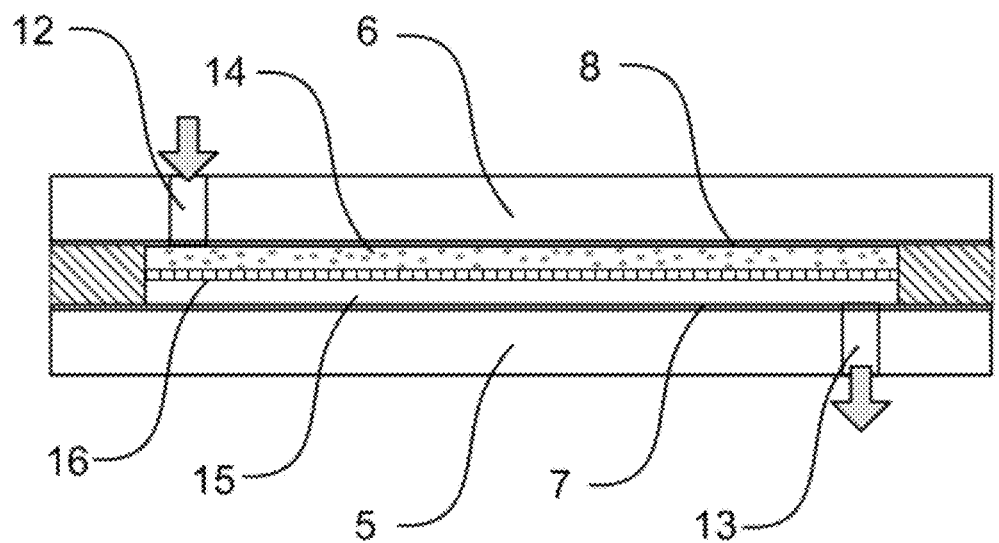
FIGS. 3(A) and 3(B) show schematic cross-sectional views of the electrical sample processing device, which has been equipped with sample cleanup and sample concentration capability, where (a) shows a filter dividing the channel into two portions, and where (b) illustrates the use of microspheres as an example material for supporting a filter within the channel.

An alternative embodiment in which the device is adapted for concentration and cleanup capabilities is presented in FIG. 3(A). A filter 16, for example a membrane filter, having a thickness less than that of the channel (or equivalently, the channel spacer) is secured within the channel such that the channel is divided into two portions 14 and 15, thereby enabling cells (or other particulate matter) within the sample to be retained by the filter as the sample is flowed between the inlet port 12 and outlet port 13. In some embodiments, at least a portion of the filter is placed between the upper and lower electrodes.

Figure 3B:
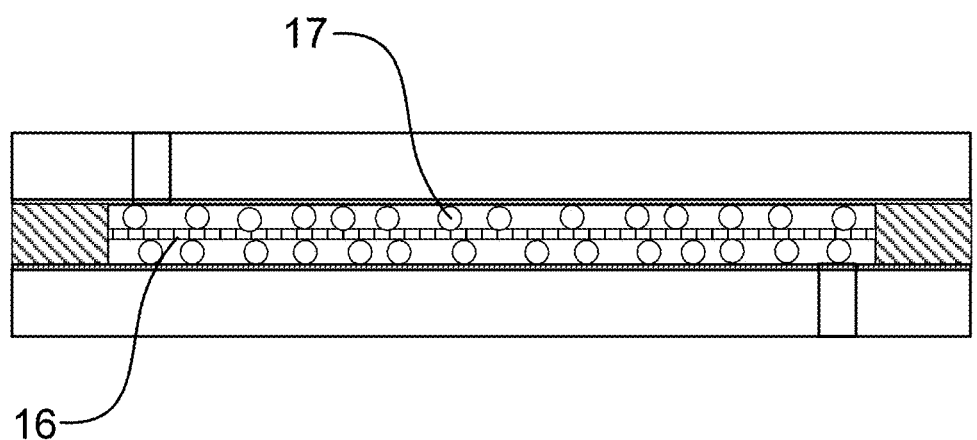

In one example implementation, the filter may be made of chemical and/or thermal resistant material, such as high density polyethylene, or polycarbonate membrane. For example, a thermally resistant filter may be beneficial in applications involving rapid thermal treatment to avoid degradation of the filter during electrical processing. Since such membrane filters are typically very thin, for example, approximately 10-20 microns, a support may be required to prevent the collapse of the filter onto the channel surface due to fluid pressure, which may prevent fluid flow through the device. Filter support may be added in the form of structures introduced into the channel which retain the electrical isolation of the upper and lower electrodes and which do not significantly impede sample flow. In one embodiment, a suitable filter support is monodispersed microspheres 17 which are bound to the membrane filter or the channel surface as shown in the cross-section diagram of FIG. 3(B). In another embodiment, the filter support may be provided by additional spacer structures located on either side of the filter, where the additional spacers are placed such that they do not substantially impede the flow of liquid within the channel. The filter support and/or the filter may be selected to be formed from a material having dielectric properties suitable for inducing the electric field to flow through the liquid within the channel, as opposed to bypassing the liquid and flowing through the filter and filter support.

Figure 4A:
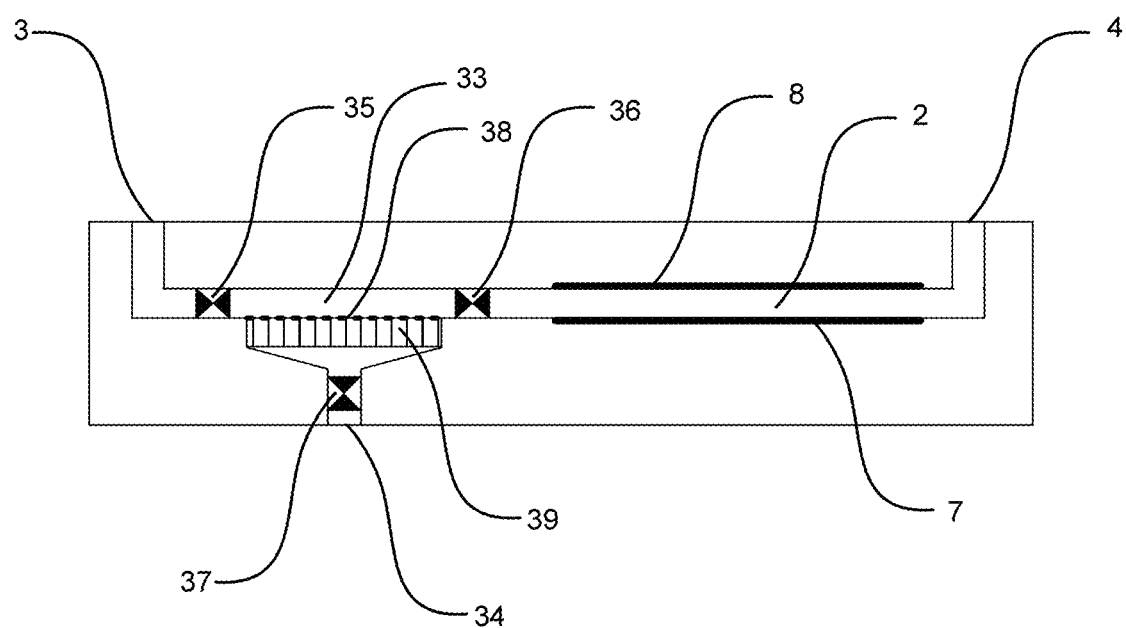
FIG. 4(A) shows a schematic cross-sectional view of the electrical sample processing device which has been equipped with an alternative sample cleanup and sample concentration capability.
Figure 4B:
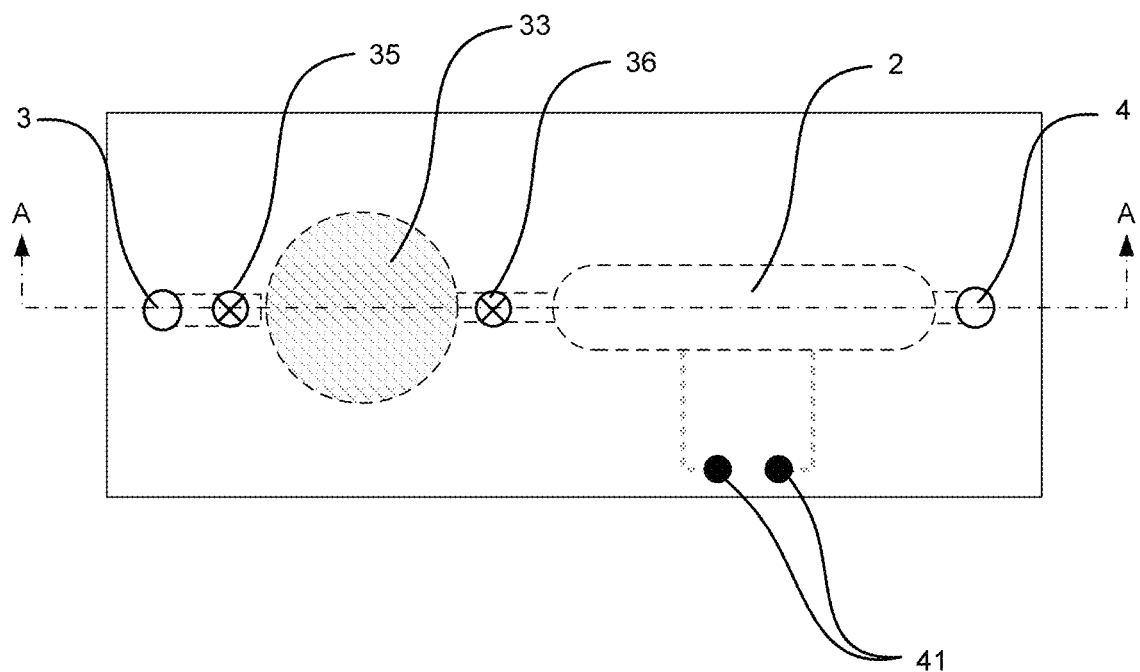

An alternative embodiment of the device adapted for concentration and cleanup capabilities is presented in cross section view A-A in FIG. 4(A) and plan view in FIG. 4(B). A filter 38, for example a membrane filter as described above, is secured within a chamber 33 fluidically connected to the inlet port 3, the electrical channel 2 and the filter outlet port 34. A diffuser support 39 is provided for the filter if necessary. When the channel inlet valve 36 is closed and the inlet port valve 35 and the filter outlet port valve 37 are open sample fluid can be flowed through the filter from the inlet port 3 to the filter outlet port 34 and then to a waste chamber in fluid connection with outlet port 34 and thereby cells within the sample are retained by the filter. A resuspension fluid of suitable composition and ionic strength for subsequent electrical processing and downstream processes is then passed from the inlet port 3 until the sample fluid has been sufficiently cleared through the filter outlet port 34. The filter outlet port 37 is then closed and the channel inlet port 36 is opened and the resuspension fluid is flowed from the inlet port thereby carrying the retained cells to the electrical channel for subsequent electrical processing. Alternatively the retained cells are resuspended and carried to the electrical channel by flow from the filter outlet port 34 while the filter outlet port 37 is open and the inlet port 35 is closed. Electrical contacts 41 are provided for the application of the electric field.

The passage of a large volume of sample fluid through the filter together with the relatively small volume of resuspension fluid used to carry the retained cells to the electrical channel allows the cell concentration for subsequent lysing and treatment to be arbitrarily increased from the initial sample concentration. It also allows for the substitution of the sample fluid by a suspension fluid appropriate for downstream processes including electrical lysing and electrical treatment and subsequent assays. The foregoing is one of a number of different arrangements of valves and fluid movements that produce equivalent functionality which can be varied by those skilled in the art based on the present disclosure.

The application of a suitable amplitude modulated electric pulse train on the two electrodes causes the cells to lyse. Depending on the magnitude and duration of the resulting electric field, the electric field and its associated temperature rise causes or induces molecules such as proteins and nucleic acids to be released from the cell as a lysate. The released molecules further undergo a transformation in the period between release and cooling down of the liquid. These processes constitute what are identified herein as electrical lysis and electrical treatment, which can provide useful steps in the preparation of cellular biological samples for diagnosis or other purposes. As discussed above, the underlying mechanisms enabling these electrical processing steps are believed to result from the electrical and thermal response in the channel from the application of the prescribed pulse train.

It is believed that the operation of the device involves establishing an electric field with consequent electric current in the channel of sufficient magnitude to cause electrical lysis of cells and/or electrical treatment of macromolecules in the channel fluid. For enhanced performance the electrolysis of the fluid at the electrode interface with its attendant gas production and bubble formation should be minimized. Some embodiments provided herein accomplish this by insulating one or more of the electrodes from the sample with a thin layer of dielectric coating, thus forming a blocking electrode that is free from direct electrical communication with liquid within the channel, which serves to eliminate any charge transfer processes from occurring across the electrode-electrolyte interface.

In other embodiments, the channel may include non-blocking electrodes that are capable of directly contacting the liquid, thereby supporting a Faradic current. The electrolysis products are avoided by operating the device using a high frequency bipolar pulse train. The ions produced at the liquid-electrode interface are significantly neutralized in alternating cycles before significantly diffusing away into the bulk medium. Unfortunately the presence of the Faradic current at the interface supports redox reactions which may damage the macromolecules in the proximity of the electrode. This effect could be alleviated by providing a protective permeation layer. Generally speaking, the permeation layer may be provided for allowing the movements of solute ions to the electrode while preventing the macromolecules from reaching the electrolyte-electrode interface.

Exemplary methods for preparing a solid support with a permeation layer are henceforth described. These examples are intended to be non-limiting, and it is to be understood that any suitable material or coating may be provided that permits solute ion transport to the electrode while restricting macromolecule transport. Permeation layer materials may optionally include functional groups for achieving the desired selective transport function of the layer.

Examples of surface preparations are the deposition of small molecules such as organosilanes and thiol linkers by covalent interaction or macromolecules such as poly-L-Lysine and PEI by physical adsorption.

In an exemplary, yet non-limiting embodiment, a heterobifunctional silane layer with functional groups, X—Si—X', can be deposited on any surface (Y) on which a silane layer can be applied to form Y—O—Si—X'. X' may be trimethoxy (—OCH$_3$)$_3$, triethoxy (—OC$_2$H$_5$)$_3$ or trichloro (Cl$_3$) and form Y—O—Si—X' chemistry upon hydrolysis.

One example of such a surface is a hydroxylated surface of aluminum, with a naturally or artificially processed oxide layer, and a heterobifunctional silane layer that is generated by Al—O—Si—X' formation. X may vary and covalently interacts with the respective functional group of any additional molecule to be attached to the silane layer via any appropriate chemistry. For example, X can be glycidyl functional group of glycidyloxipropyl-trimethoxysilane (GOPTS) or amino functional group of 3-aminopropyltriethoxysilane (APTS). Glycidyl functional group of GOPTS will interact readily with an amino functional group of the molecule to be attached. An additional activation of amino functional group of APTS with any crosslinking chemistry, for example, 1-ethyl-3-(3-dimethylaminopropyl) carbodiimide) (EDC) and N-hydroxysuccinimide (NHS), may be provided for covalent interaction with a carboxyl functional group of the molecule to be attached. Optionally, amino functional group of APTS can be pre-activated with any known chemistry, for example, with a glutaraldehyde homobifunctional crosslinker, to interact readily with amino functional group of the molecule to be immobilized.

Alternatively, protein molecules with high affinity and specificity such as avidin or streptavidin can be immobilized on the functionalized surface via any suitable chemistry and a biotinylated molecule can be readily immobilized on the surface by biotin-avidin affinity interaction.

The surface can be prepared by procedures presented in the following non-limiting example. Polished aluminum support plates were cleaned with water then rinsed twice with methanol and air-dried. 2% 3-Aminopropyl Triethoxysilane is prepared in 95% Methanol 5% water and the plates were immersed in silane for 5 min. Then, the plates were rinsed in methanol twice, air-dried and baked at 110° C. for 10 min. After cooling, the plates were immersed in 2.5% glutaraldehyde homobifunctional crosslinker in phosphate buffered saline, pH 7.4 at room temperature for 1 hour. The plates were rinsed thoroughly with water and air-dried.

In another embodiment the permeation layer can be a hydrogel, such as a polyacrylamide based network-like hydrogel (e.g., Yu et al., BioTechniques 34:1008-1022, 2003) or, for example, a brush-like hydrogel such as the hydrogel disclosed in U.S. Pat. No. 6,994,964.

As noted above, the application of an electric potential difference between two electrodes separated by an electrolytic solution can result in electrochemical reactions at the electrode-electrolyte interface if the applied voltage exceeds a threshold value. In such a case, gas bubbles may be generated at the electrodes due to electrolysis of water or electrochemical reactions of electrolytic ions. The gas formation can rapidly obstruct the channel leading to disruption in normal flow characteristics. In addition, the pressure increase in the channel could cause mechanical damage of the device. Finally, the products of the redox reactions due to Faradic currents may degrade the biological molecules in the solution rendering the sample preparation unsuitable for the downstream assays.

One method for avoiding such problems is the application of an alternating voltage with sufficiently high frequency such that gas bubble formation is minimized as discussed above. In another approach the generation of oxygen and hydrogen bubbles can be suppressed by adding a redox-couple to the sample flowing along the electrodes. As an example, quinhydrone, which is a complex between hydroquinone (H$_2$Q) acting as an electron donor and p-benzoquinone (Q) acting as an electron acceptor, can be added to the flow streams. Instead of water oxidation and reduction that generates oxygen and hydrogen, now H$_2$Q is oxidized and Q is reduced without any bubble generation. A drawback of both foretold methods is that the interfacial electrochemical reactions involving macromolecules cannot be fully avoided. It is further noted that most macromolecules are charged in an aqueous medium, and thus may drift to the interfaces under the influence of high fields typically used for the electrical lysis.

As noted above, the generation of gas bubbles and interfacial electrochemical reactions can be avoided by providing a channel that incorporates blocking electrodes to suppress a Faradic current. It is well known, however, that the application of a constant electric field in a channel containing an aqueous ionic solution, where the channel is configured to suppress a Faradic current, results in formation of electric double layers near the electrodes which rapidly screen the applied electric field in the inner regions of the channel. Accordingly, the actual electric field experienced by the suspended cells, referred to as the "effective field", may drop to a small fraction of the nominally applied field shortly after the field is switched on.

In one embodiment, the aforementioned drawbacks associated with screening of the electric field within the liquid are avoided as follows. As noted above, the applied voltage is provided as a train of amplitude modulated pulses. If the duration of the pulses does not exceed the characteristic charging time of the electrodes, then the shielding effects on the effective electric field can be tolerated. Accordingly, in one embodiment the electrodes (for example, electrodes 7 and 8 in FIGS. 1-3) are provided as a thin conductive substrate and with a thin dielectric coating in contact with the channel fluid, where the surface profile of the conductor and dielectric is microstructured for surface area enhancement such that the blocking electrode surface area substantially exceeds the surface area of the corresponding flat surface. The large capacitance thereby achieved enables a charging time greater than one microsecond, such as on the order of tens of microseconds.

The capacitance of the blocking layer can also be enhanced by providing a thin dielectric layer having a high dielectric constant. In one example implementation, the metal substrate is aluminum, and the dielectric layer is aluminum oxide (Al$_2$O$_3$). This aluminum oxide (Al$_2$O$_3$) dielectric layer is formed by electrochemically oxidizing the aluminum (anodized aluminum). In order to increase the effective surface by as much as 100 times and to provide a corresponding increase to the capacitance per unit nominal area, the electrode is etched with a dense network of microscopic cavities and tunnels.

In the context of the present disclosure, these types of electrodes are identified by the term SEOA (surface enhanced oxidized aluminum). The thickness of the dielectric layer is determined by the applied voltage during the electrochemical forming (anodizing) process. In one example implementation, the thickness is chosen to be 2 nm per each volt that can be safely applied on the electrode. In examples for which the applied voltages are about 200 V, the thickness of the dielectric layer for safe operation under long duration pulses is thereby estimated to be on the order of 400 nm. This thickness can in some cases result in a charging time that is too short, thus reducing the duration of the effective field in the channel to undesirably short periods. In addition, an appreciable amount of the applied voltage is dropped in the dielectric layer, which generally has much lower dielectric constant as compared to water. In practice, when the duration of the pulses in the train, $t_p$, do not exceed 1 ms, much lower dielectric thickness of about 50 nm can be used without the hazards of establishing Faradic current due to onset of anodization processes on the electrode. Investigations by the inventors have indicated that an aluminum oxide layer thickness of 50-200 nm is suitable for most applications described herein. For example, in the case of the electrical lysis of Gram positive bacteria, electric fields of over 10 kV/cm are desirable, and a thickness greater than 50 nm is desired to avoid electrical breakdown. In some embodiments, the dielectric thickness and surface area enhancement may be selected to provide a capacitance in the range of approximately 0.5 µF/cm² to 200 µF/cm². In other embodiments, the capacitance of the dielectric layer may be between approximately 2 µF/cm² to 50 µF/cm². The selected dielectric constant may depend on the ionic strength of the suspension liquid and the constraints of the frequency response of the driving electronics. For example, when the ionic strength of the liquid is below 1 mM and cost considerations requires the maximum operating frequency of the driving electronic to less than 10 kHz, the capacitance may be chosen to be greater than 5 µF/cm².

Although aspects of the disclosure are described with reference to surface enhanced oxidized aluminum (SEOA), it is to be understood that SEOA is merely one example material for implementing the present embodiments. In another example, a substrate with a different metal (with high surface area) and an oxide layer may be employed, such as tantalum and tantalum oxide. In another embodiment, silicon and silicon dioxide may be employed, where the silicon may be doped with appropriate concentration to provide suitable conductivity.

In one example embodiment involving a blocking electrode formed from silicon and silicon dioxide, the silicon may be porous silicon, such as macroporous silicon or microporous silicon. In one example, the silicon is macroporous silicon with pore walls that are sufficiently thick to support the growth of an oxide layer with a thickness on the nanometer scale, while maintaining an underlying layer of conductive silicon. Suitable oxide layer thickness and surface enhancement are selected as described above in the SEOA example.

In the preparation of porous silicon, the silicon substrate is typically doped, thereby providing a conductive electrode for use with the present methods. In some implementations, the porosity of the silicon can be controlled by varying the etching conditions, and/or post-etching the structure in a suitable etchant (such as hydrofluoric acid). The oxide layer may be added after etching, where the oxide is generated by oxidation in a suitable thermal environment. As will be apparent to those skilled in the art, the thickness of the oxide layer can be controlled according to the time and temperature of the thermal incubation. The pores may be formed as an ordered array of two-dimensional pores, for example, by photolithographically defining pore nucleation sites, or the pores may be form as a disordered structure.

Figure 5A:
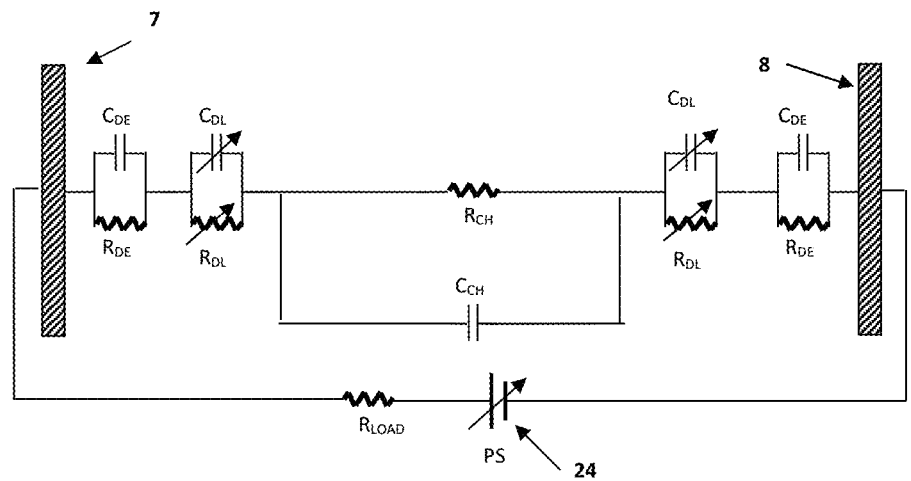
FIG. 5(A) shows an equivalent circuit model for the device of FIG. 2.

The electrical properties of the channel can be modeled by the equivalent electrical circuit presented in FIG. 5(A). The capacitance $C_{DL}$ corresponds to the dynamic double-layer capacitance at the interfaces of dielectric layer and the liquid in the channel. $R_{DL}$ is the parallel (in the direction of the channel thickness) resistance corresponding to leakage current in the double layer.

In general, values of $C_{DL}$ for flat metal surfaces fall in the range 5-50 µF/cm² depending on the type of electrode, ionic strength and composition of the solution, temperature and voltage. However, roughness of the surface can increase the capacitance to higher values. Capacitance $C_{DE}$ is the capacitance of the dielectric layer whose value depends on the layer thickness and the effective area of the electrode. The capacitance for the SEOA electrodes used in the experiments described herein was either 6 or 36 µF/cm². These electrodes were designated as SEOA1 and SEOA2, respectively.

Resistance $R_{DE}$ is the equivalent parallel resistance of the dielectric layer and accounts for leakage current in the capacitor. It decreases with increasing capacitance, temperature and voltage. Typical values for $R_{DE}$ are on the order of $100/C_{DE}$ MΩ with $C_{DE}$ in µF. $R_{CH}$ represents the bulk solution resistance and $C_{CH}$ the bulk capacitance. The value of $C_{CH}$ is so small that it can be approximated with open circuit. For a channel with a height of 100 µm, the resistance $R_{CH}$ is about 200Ω per cm² of the electrode, when the ionic strength of the liquid is 0.5 mM. $R_{LOAD}$ is the sum of the power supply output resistance and the input resistance of the electrodes. All the electrical parameter values, with the exception of $R_{LOAD}$, $R_{DE}$ and $C_{DE}$ are dependent on the ionic strength of the carrier solution. The load resistance modifies the voltage division among the circuit components and becomes particularly important at higher ionic strengths.

Figure 5B:
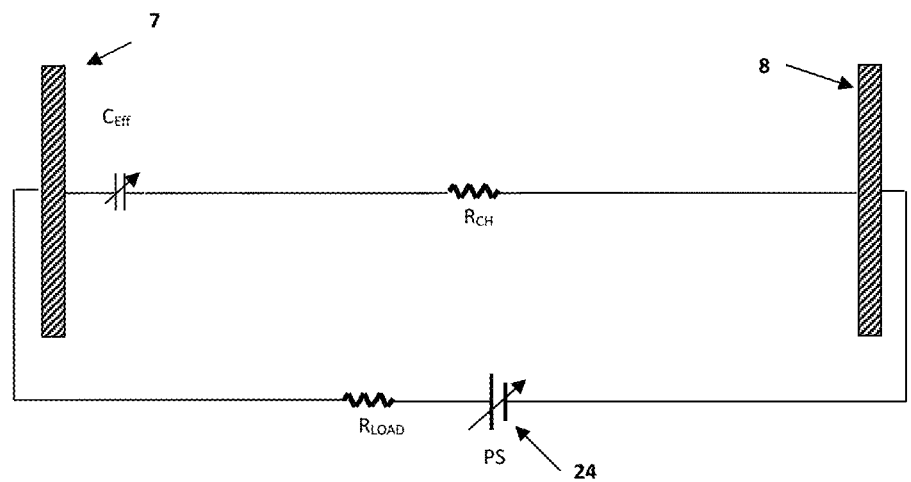

Considering the typical values of the electrical parameters, the equivalent circuit can be simplified as presented in FIG. 5(B). The resistances $R_{DE}$, and $R_{DL}$ are sufficiently large that they can be approximated as open. The double layer capacitances and dielectric layer capacitances have been combined in series as $C_{Eff}$. The double layer charging time, according to this circuit model, is given by $$t_c \approx (R_{LOAD}+R_{CH})(C_{DE}C_{DL})/2(C_{DE}+C_{DL}) \equiv (R_{LOAD}+R_{CH})C_{Eff} \qquad (1)$$

Figure 5C:
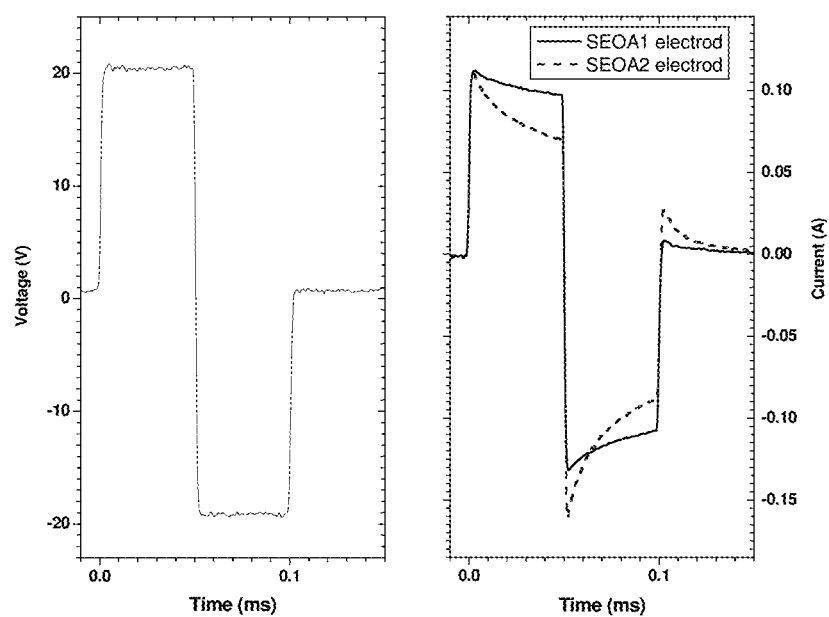
FIG. 5(C) shows the current response of two typical channels using SEOA1 or SEOA2 electrodes to a bipolar pulse.

It is noted that this charging time is 1-2 orders of magnitude larger than that achievable without surface enhancement of the electrode. Accordingly, the use of SEOA as one or more of the electrodes in the device provides a substantial increase in the charging time. For example, in one embodiment, the charging time may be at least one microsecond for liquids having an ionic strength below about 10 mM, thereby supporting the aforementioned methods of electrical lysis and sample treatment. FIG. 5(C) presents a typical current response of the channel to an applied bipolar square pulse for electrodes SEOA1 and SEOA2. As is observed, the decrease in the current, which is an indicator of the effective field, is sufficiently small over the 50 µs duration of the square pulses. The channels, which were filled with 0.4 mM phosphate buffer, had dimensions 28×3.17×0.1 mm³.

Figure 2:
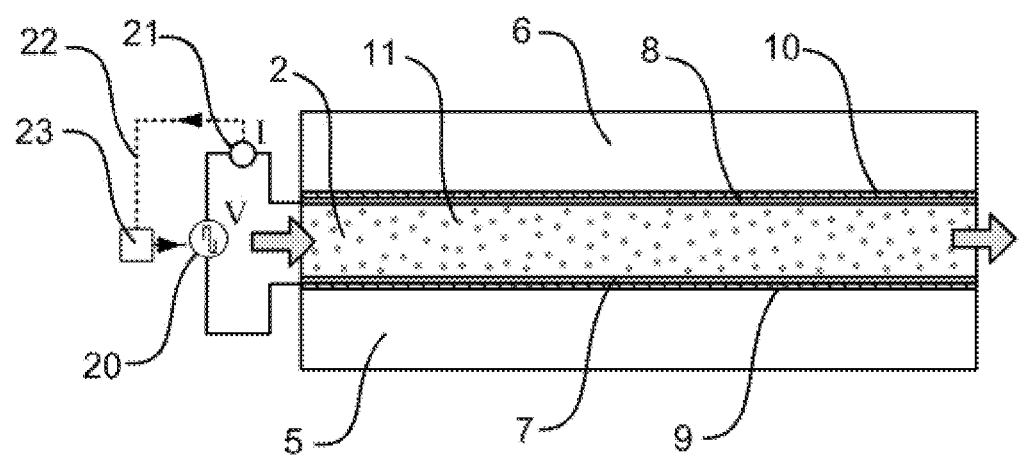
FIG. 2 shows a schematic cross-sectional view parallel to the flow of the electrical sample processing device.

An example method of employing the present device for sample processing is now illustrated with reference to FIG. 2. The external voltage source, 20, applies a potential difference between the two electrodes, 7 and 8, in the form of an amplitude modulated train of pulses. In one example, the pulses are bipolar square pulses. Other pulse shapes, which may ease the design of driving electronics, can be utilized. However, the published data on inactivating microorganisms in food samples indicate that square pulses are more effective in terms of irreversible electroporation.

The electrical characteristics of the channel depend on the ionic strength of the aqueous solution. Accordingly, in example embodiments, the selection of an appropriate applied voltage, pulse duration and pulse count may be performed based on a prior knowledge of the ionic strength of the sample solution, or alternatively based on in-situ electrical measurements for setting the parameters of the pulse train. In one example, this may be done according to the feedback based on the electrical current monitored by the meter 21 via the control feedback loop 22 and the controller unit 23.

In some embodiments, the maximum channel temperature may be maintained at the desired temperature during the residence time, while avoiding an extensive liquid to vapour phase change in the sample. This may be done by controlling the temperature within the channel using the measured current as a feedback parameter, and providing this feedback parameter to the voltage controller 23. the temperature and/or the residence time for effecting a desired change in the sample may be controlled, in response to the measured current, according to many possible methods. In several non-limiting examples, the current (and/or a parameter related to the current, such as the impedance) may be employed to control the channel temperature by controlling the voltage pulse train amplitude, pulse-density (the number of pulses with fixed duration in given time interval), duty cycle, and/or pulse width.

In some embodiments, the temperature dependence of the electrical conductivity of the sample fluid may be used to monitor the temperature of the liquid. The electrical conductivity of aqueous fluids typically increases with temperature at a rate, depending on the composition of the fluid, of approximately 2% to 3% per degree Celcius (R. B. McCleskey, *J. Chem. Eng. Data* 2011, 56, 317-327).

Figure 5D:
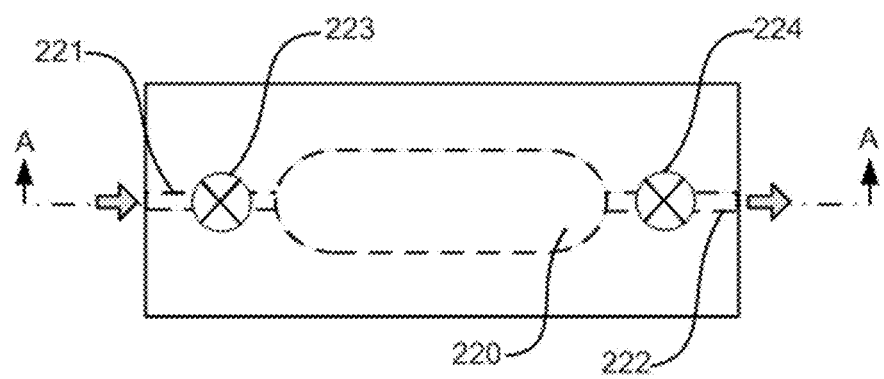
FIGS. 5(D) and 5(E) schematically depict the plan FIG. 5(D) and cross sectional FIG. 5(E) views of an example electrical chamber.
Figure 5E:
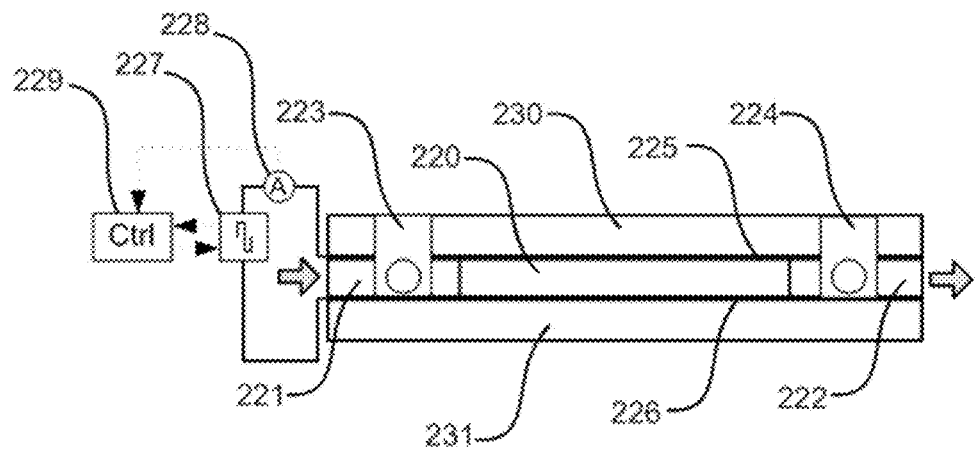

FIG. 5(D) illustrates an example implementation of the electrical processing channel 20 of a microfluidic device, which shown in cross-sectional view A-A in FIG. 5e. Channel 220 is connected by inlet and outlet channels 221 and 222 to inlet and outlet ports respectively through which fluids of interest enter and exit from the electrical channel. The electrical channel has top and bottom surface electrodes 225 and 226 which allow the application of an electric field across the channel by the external voltage source 227, which is capable of supplying an amplitude modulated train of voltage pulses. The device includes valves 223 and 224 for opening and closing inlet and outlet ports to enable superheating. Alternatively, flow restrictions in the inlet and outlet ports and/or channels may be used to enable superheating of the liquid. In both cases, temperature control is accomplished through feedback from the detection of electrical current flowing across the channel.

The resulting electrical current flowing across the channel is measured by a current monitor 228 and supplied to the voltage controller 229. The applied voltage amplitude may also be supplied to controller 229, as required, for example, for measurement and subsequent control of electrical channel impedance. In one embodiment, the voltage pulses are regulated by controller 229 in response to current and voltage feedback to maintain electrical channel impedance at a desired level. In another embodiment, the current monitor can be used to measure current during initial operation of the electrical channel and the controller 229 can be used to determine the appropriate subsequent voltage train parameters in response to the measured current. The latter embodiment may be used, for example, to determine appropriate voltage train parameters for fluids of unknown ionic strength.

Figure 5F:
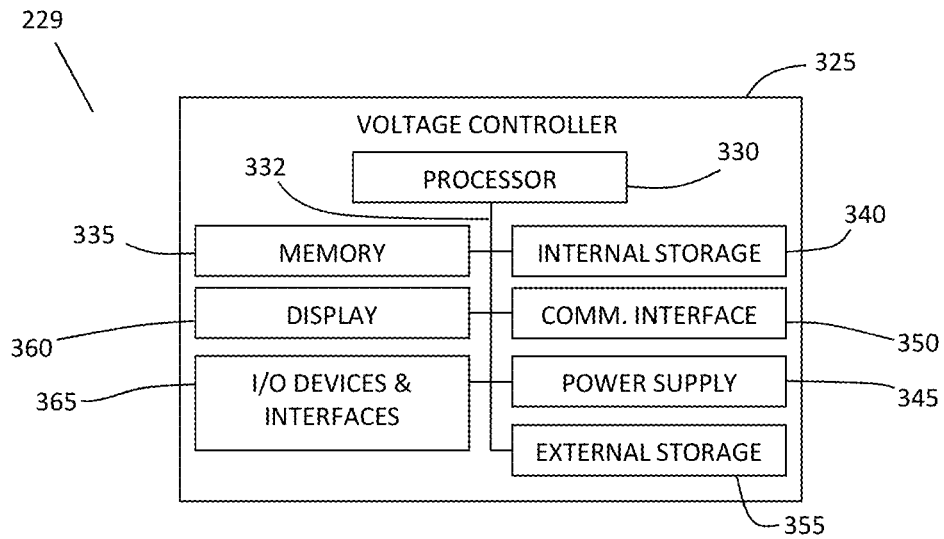
FIG. 5(F) is an example implementation of a voltage controller.

FIG. 5(F) illustrates an example embodiment of voltage controller 229. Voltage controller 229 may include one or more processors 330 (for example, a CPU/microprocessor), bus 332, memory 335, which may include random access memory (RAM) and/or read only memory (ROM), one or more internal storage devices 340 (e.g. a hard disk drive, compact disk drive or internal flash memory), a power supply 345, one more communications interfaces 350, external storage 355, a display 360 and various input/output devices and/or interfaces 355.

Although only one of each component is illustrated in FIG. 5(F), any number of each component can be included in voltage controller 229. For example, a computer typically contains a number of different data storage media. Furthermore, although bus 332 is depicted as a single connection between all of the components, it will be appreciated that the bus 332 may represent one or more circuits, devices or communication channels which link two or more of the components. For example, in personal computers, bus 332 often includes or is a motherboard.

In one embodiment, voltage controller 229 may be, or include, a general purpose computer or any other hardware equivalents. Control and processing unit 325 may also be implemented as one or more physical devices that are coupled to processor 330 through one of more communications channels or interfaces. For example, control and processing unit 325 can be implemented using application specific integrated circuits (ASICs). Alternatively, control and processing unit 325 can be implemented as a combination of hardware and software, where the software is loaded into the processor from the memory or over a network connection.

Voltage controller 229 may be programmed with a set of instructions which when executed in the processor causes the system to perform one or more methods described in the disclosure. Voltage controller 229 may include many more or less components than those shown.

As described above, the voltage pulse train applied across the channel electrodes will cause substantial current to flow in the channel fluid causing rapid Joule heating of the fluid. The thermal behavior of the electrical channel is influenced by a number of factors including the amplitude, frequency and duration of the applied voltage pulses, the thermal properties of the channel, the ionic concentration of the solution, and the pressure in the channel.

Figure 5G:
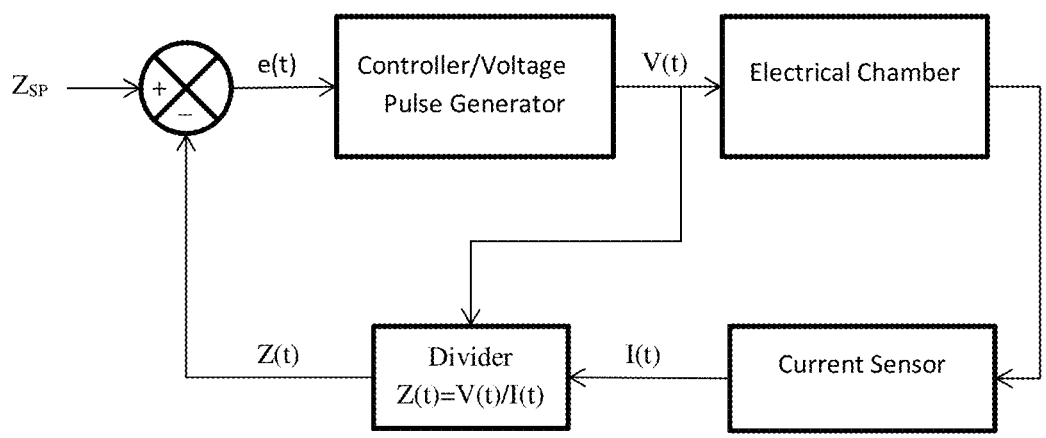
FIG. 5(G) shows the block diagram of the impedance based temperature regulation scheme.

Active feedback control of the voltage pulse train applied to the channel is described by the example implementation of the control diagram shown in FIG. 5(G). As the temperature of the fluid in the channel is represented by the electrical impedance of the channel, impedance $Z(t)$ obtained from measured voltage $V(t)$ and current $I(t)$ is used as the feedback signal. An error parameter $e(t)$ is obtained from the impedance relative to a predetermined setpoint impedance $Z_{SP}$ and provided to the controller.

It is to be understood that a wide range of choices exist for controlling the voltage pulse train in response to the error signal $e(t)$. In some non-limiting examples, the voltage pulse train amplitude may be modulated, an inter-pulse delay may be introduced and modulated, or pulses may be skipped in relation to the magnitude of the error signal. In the latter two cases the voltage amplitude is held constant and hence the feedback signal may more simply be the measured current. For example, as shown in Example 6 below, the limiting case of pulse skipping was employed, whereby the voltage pulse train was halted when a predetermined current level was reached.

Active feedback control is now described in an example implementation in which voltage amplitude is modulated to reach and maintain predetermined minimum impedance. An initial voltage pulse train of constant amplitude and frequency is applied and upon reaching a predetermined setpoint current level, active feedback control is activated. Thereafter the voltage controller adjusts the voltage pulse amplitude in response to measured electrical impedance in order to maintain the impedance at a predetermined setpoint level for the remainder of the voltage pulse train.

The performance or effectiveness of the electrical lysing and electrical treatment methods may be enhanced by increasing the maximum temperature reached in the channel fluid and/or by increasing the residence time of the channel at elevated temperatures. The peak temperature which can be reached by the fluid in the channel is limited to the boiling temperature of the fluid, which is influenced by bubble nucleation conditions and pressure. Since the fluid temperature in the channel is generally non uniform and greater in a central region, bubble nucleation may be delayed until fluid temperatures in this region have exceeded normal boiling temperature. Further increases in the boiling temperature can be achieved when the pressure in the channel is greater than atmospheric pressure.

When fluid temperatures are achieved which are greater than the boiling temperature at atmospheric pressure, the fluid is said to be superheated. This can be done actively by pressurizing the channel prior to or during the application of voltage pulses. Alternatively, by closing the inlet and exit ports of the channel, increased pressure can be developed in the channel as the temperature of the fluid is increased during the application of voltage pulses. Increased pressure in the channel can also be achieved with open inlet and outlet ports by providing features at the inlet and outlet to the channel which restrict fluid flow.

Figure 19A:
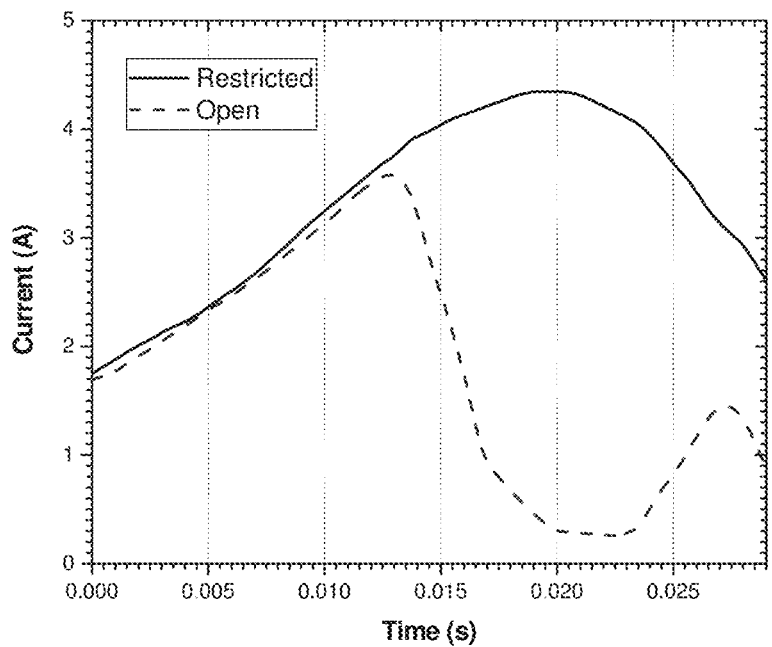
FIG. 19(A) shows the measured current envelopes for the channels in which *S. cerevisiae* cells were electrically lysed, for both restricted and open channels.

In the latter case, as the voltage pulses are applied, the temperature of the fluid increases, causing expansion of the fluid and ultimately the generation of a gas phase when the fluid reaches its boiling temperature. During the application of the voltage pulses, the channel entrance and exit flow restrictions cause a pressure drop between the electrical channel and the exit to atmosphere which results in elevated pressure in the electrical channel, leading to superheating of the fluid. Various mechanisms for providing flow restrictions are known by those skilled in the art and include choosing appropriate electrical channel inlet and outlet orifice size and geometry and/or providing inlet and outlet channels for which the hydraulic diameter, length, surface roughness and the addition of bends are chosen so as to increase pressure drop along its length during fluid flow. Residence times can also be effectively increased using this method by slowing the formation of the gas phase, which results in the lower rate of decrease of current following the peak in the current response of the channel, as can be seen in the example presented below (FIG. 19A).

The current or impedance feedback control methods described previously provide a means to control the maximum temperature in the channel and/or the residence time at predetermined temperatures. When used in conjunction with an electrical channel with closed or restricted inlet and outlets, as described above, superheating of the fluid can be achieved and monitored via the electrical current and/or impedance of the channel.

It may be desirable under these superheating conditions to limit the pressure buildup in the channel. This may be achieved, for example, by halting the delivery of voltage pulses or by modulating the electrical energy delivered to the electrical channel once a predetermined setpoint impedance is reached.

Channels with minimal or no flow restriction at the inlet and outlet, herein termed open channels, may also be so controlled, albeit at lower temperatures, prior to the onset of liquid to vapour transition. Longer residence time at elevated temperatures may be achieved by active control of the voltage pulse train in response to measured impedance in such way as to maintain predetermined minimum impedance.

In addition to increasing the exposure time of cells and macromolecules to elevated temperatures, longer residence times also allow time for heat transfer to occur from hot central zones in the fluid to the cooler boundary regions thus exposing more cells and macromolecules to the higher temperature levels.

Upon applying the voltage to the electrodes, the passage of the ionic current through the sample liquid results in the generation of heat during the pulse train which is followed by rapid cooling after the pulse train is ceased. As it will be seen in the experimental examples presented below, the performance of the channel during electrical treatment depends on its thermal characteristics, and the channel geometry, dimensions, and thermal material properties are selected to be sufficiently thermally insulating to support flash heating under the application of voltage pulses to the electrodes (for example, such that the temperature of the liquid increases at a rate in excess of approximately 250 degrees Celsius per second), while also being sufficiently thermally conductive to provide for rapid, sub-second cooling time after removing the applied voltage pulses. In other words, by selecting channel materials with an appropriate thermal conductivity, and channel dimensions and geometries that provide an appropriate heat capacity (or, equivalently, an appropriate thermal mass or heat sinking capability) for the surface to volume ratio of the channel, the initial heat rise can be followed by a rapid cooling cycle. It will be understood that there are many different configurations of the channel dimensions and geometry and choices for the channel materials that will exhibit a suitable thermal response. Accordingly, the specific examples provided herein, and in the examples below, are provided as heuristic and non-limiting examples. Other configurations and material choices may be made by routine experimentation without departing from the scope of the present disclosure.

The thermal properties of the channel are dependent on many different channel parameters. For example, the channel conductivity and heat capacity can be controlled according to the geometry and/or thickness of the metal electrode. Most electrodes will have a high thermal conductivity, but the thermal properties of the channel can be tailored by selecting an appropriate electrode thickness to provide a suitable heat capacity and an appropriate (e.g. thermally insulating) substrate upon which the electrodes are supported.

Accordingly, one or more of the channel electrodes may be provided as a metal foil or coating having a high thermal conductivity and/or a high heat capacity relative to the total volume of fluid in the channel to promote rapid cooling after electrical treatment, while at the same time providing a sufficiently small heat capacity such that the flash heating can produce a rapid temperature rise within the channel during the application of the voltage pulses (for example, a temperature rise greater than approximately 250 degrees Celsius per second).

Alternatively or additionally, the channel may include lateral heat sinking elements. In one embodiment, the thermal conductivity of the side walls of the channel may be selected such that the side walls can act as a lateral heat sink. In another example, one or both electrodes may extend beyond the channel-defining region, thus providing another lateral heat sinking path.

Figure 6:
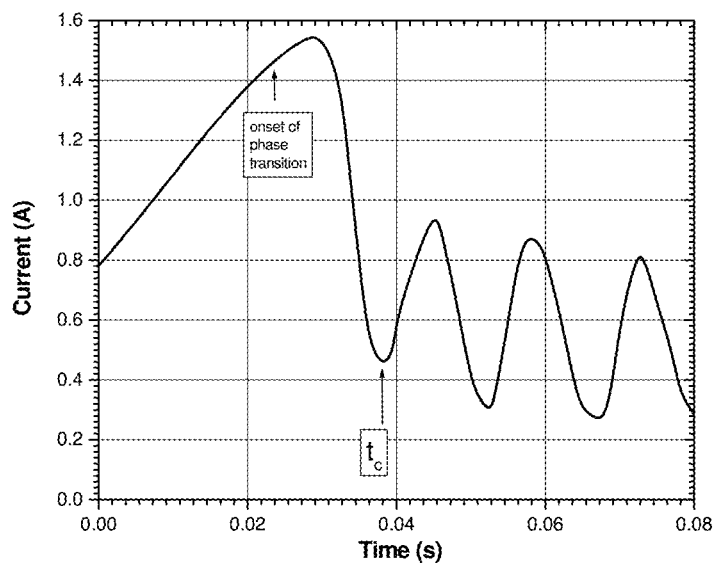
FIG. 6 shows the measured current envelope for an open channel.

The electrical and thermal behavior of the channel is now illustrated with an example of measurements taken during a typical channel experiment. FIG. 6 shows the envelope of the measured electrical current pulses in a channel whose inlet and outlet ports were open to atmospheric pressure and which was subjected to an applied voltage in the form of a square bipolar pulse train with n=800 pulses, an amplitude of 196 V and a frequency of 10 kHz (the load resistance, $R_{LOAD}$ in FIG. 5B, was 10 Ohm). The channel structure comprised an aluminum upper plate, glass lower plate, with an inner surface of each plate including a 0.1 mm polyimide insulating layer, and with a SEOA electrode (SEOA1) provided on each polyimide insulating layer, such that the oxidized electrodes contact a fluid within the channel, and with a 0.1 mm polyimide spacer defining the channel height.

The channel with dimensions 28×3.17×0.1 mm³ was filled with 0.4 mM phosphate buffer. The characteristic feature of the channel electrical current response is the initial monotonic rise of current to a maximum value, followed by a rapid reduction to a minimum value at time $t_c$, accompanied in some cases by quasi periodic fluctuations as seen in FIG. 6.

Because, in general, the conductivity of an aqueous solution is a linearly increasing function of temperature (Aqueous Systems at Elevated Temperatures and Pressures, Chapter 10, Elsevier 2004), one may conclude that the initial rising current is due to Joule heating of the fluid in the channel. Since the channel is open to the atmosphere, one would expect that the fluid temperature will be limited to the liquid saturation state temperature at atmospheric pressure which for the solution used is approximately 100° C. Without intending to be limited by theory, it is believed that further energy input will result in a phase transition occurring in those areas of the channel which have reached this temperature. The presence of vapor in the channel, as a result of the phase transition, will significantly reduce the conductance of the channel, leading to the observed decrease of current.

A finite differences analysis of transient heat transfer in the channel was used to estimate channel temperatures both during and following the electrical pulse train. Fourier's law of heat conduction was solved numerically in conjunction with conservation of energy for a channel spatially discretized across the thickness and the width of the layered channel assembly. Joule heating of the channel fluid is calculated assuming a linear thermal dependence of the conductance of the fluid the linear parameters of which are determined from the experimentally measured current at the initiation of electrical pulses and the iterative solution of the current at 100° C. which lies on the experimentally measured curve of FIG. 6. Thereby the onset of phase change is estimated to occur at the center of the channel at t=0.024 s, as identified in FIG. 6.

Figure 7:
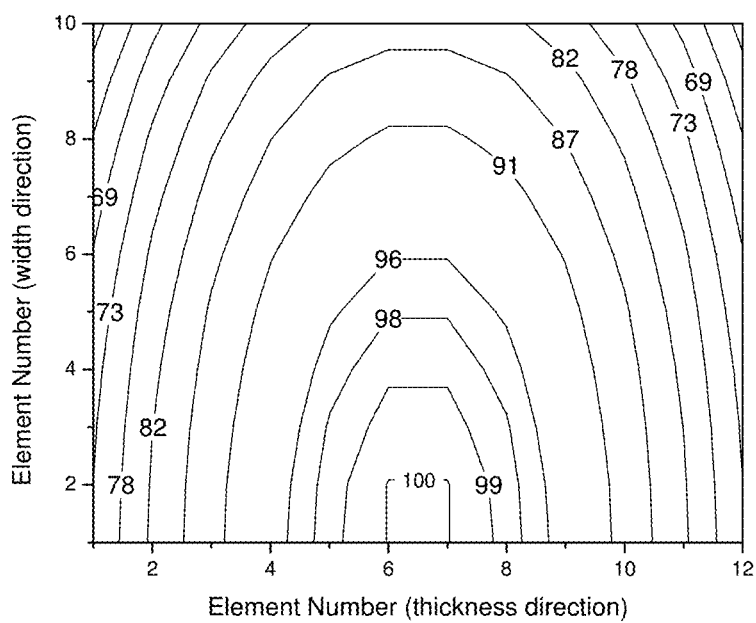
FIG. 7 shows the channel temperature distribution for the open channel joule heating analysis.
Figure 8:
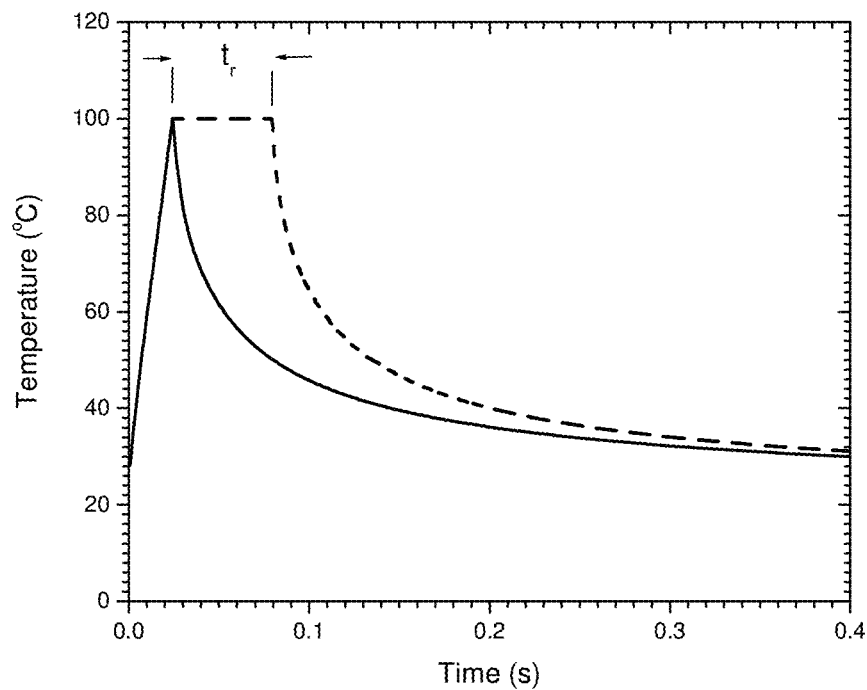
FIG. 8 shows the temporal dynamics of the maximum channel transient temperature joule heating analysis.

The simulated spatial temperature distribution in the channel at t=0.024 s is provided in FIG. 7. FIG. 8 shows the calculated time dependence of the spatial maximum temperature, assuming that the applied voltage is set to zero at t=0.024 ms. In this model, if the voltage remains applied for a further time $t_r$, the peak temperature will be maintained and that portion of the fluid which reaches 100° C. will undergo a phase transition.

The existence of a mixed liquid-vapour phase that occurs following the initiation of the phase transition is believed to result in a localized reduction of conductivity, which in turn leads to a redistribution of current within the channel. It is further believed that after the onset of the phase transition, the mixed phase region undergoes expansion due to the continued increase in fluid temperatures outside the region of vaporization. Accordingly, as the mixed phase region expands further, the current within the channel is expected to decrease substantially as net conductivity of the channel falls.

Referring now to FIG. 6, the time dependent current profile appears to behave in a manner that is consistent with the interpretation provided above. Specifically, the current initially rises towards a maximum value as the phase transition is expected to be initiated, after which the current decreases as predicted by the mixed-phase model.

Furthermore, the quasi-periodic features following the maximum current may be attributed to further phase transition cycles, with corresponding increases and decreases in conductivity and current. These phase transition cycles are believed to be a result of the reduction in current and subsequent cooling and condensation, which in turn leads again to a rise of current and another cycle of vaporization and condensation.

The temperature of the channel fluid is expected to be in a quasi steady state during the phase transition cycles. As a result, this mechanism may provide passive control of the peak temperature during electrical processing. This constitutes a self-limiting passive feedback mechanism for the temperature control.

In another example implementation, the current flowing between the device electrodes may be monitored by identifying an initial peak in the time-dependent current (which may correspond to the onset of a phase transition in the liquid), and continuing to apply to voltage pulses for a prescribed time duration after the detection of a reduction in current below the peak. The current may also or alternatively be monitored to detect the presence of one or more features in the time-dependent current, such as for example local current minima or maxima, and the application of the voltage pulses may be maintained during a time interval corresponding to one or more of these features.

Referring again to FIG. 8, the simulations indicate that following the removal of the voltage, the channel fluid cools down rapidly due to thermal diffusion from the relatively small volume of channel fluid to the neighboring materials of the flow cell, returning close to initial temperatures in less than 1 second. This is a useful mechanism that can be taken advantage of to avoid thermal damage to macromolecules arising from prolonged exposure to high temperatures.

In another embodiment, the pressure within the channel may be controlled in order to superheat the fluid within the channel during electrical treatment. For example, the channel may include valves for enclosing the internal volume, thereby increasing the pressure within the channel in response to an electrically induced increase in temperature.

Figure 9:
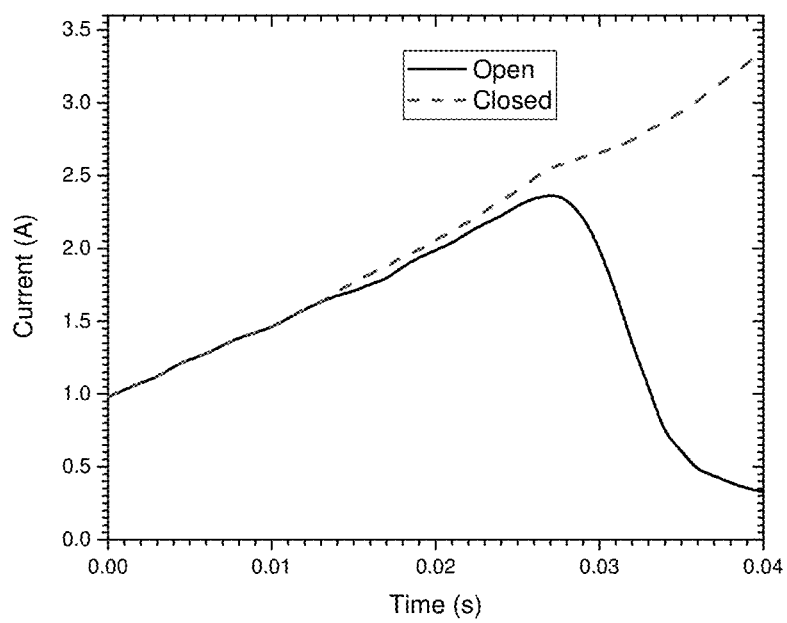
FIG. 9 shows the time dependent peak current envelope for channel with a shutoff valve at inlet and outlet ports in an open and closed position.

FIG. 9 shows the envelope of experimentally measured electrical current pulses in a channel having a configuration as described above, but further including a shutoff valve at the inlet and the outlet port. The channel was subjected to an applied voltage in the form of a bipolar square pulse train with n=400 pulses, an amplitude of 200 V and a frequency of 10 kHz. As can be seen in FIG. 9, when the channel inlet and outlet ports are closed, the current initially follows the behavior of the open port channel, but instead of reaching a maximum value with a subsequent decrease of current, the current monotonically increases until the end of the pulse train.

Accordingly, during electrical heating, pressure in excess of atmospheric pressure builds up in the closed channel, such that the channel fluid remains in a liquid phase and becomes superheated as its temperature exceeds the atmospheric liquid saturation state temperature. Estimates obtained from the finite differences thermal analysis suggest that the confined liquid in the closed channel reaches temperatures which are on average approximately 35° C. higher than the open channel in this example. The thermal analysis also indicates that after removing the applied voltage, the superheated fluid rapidly cools, returning close to initial temperatures within 1 second.

By regulating the pressure in the channel, the superheated fluid temperature can be controlled to limit the peak temperature and/or to maintain a temperature near the peak temperature. More specifically, when the pressure is maintained at a fixed value, the continued application of voltage pulses after reaching the peak current value (i.e. near the time of phase transition initiation) will maintain a quasi-steady state in which the current, temperature and conductivity may oscillate within a range of values.

Figure 10:
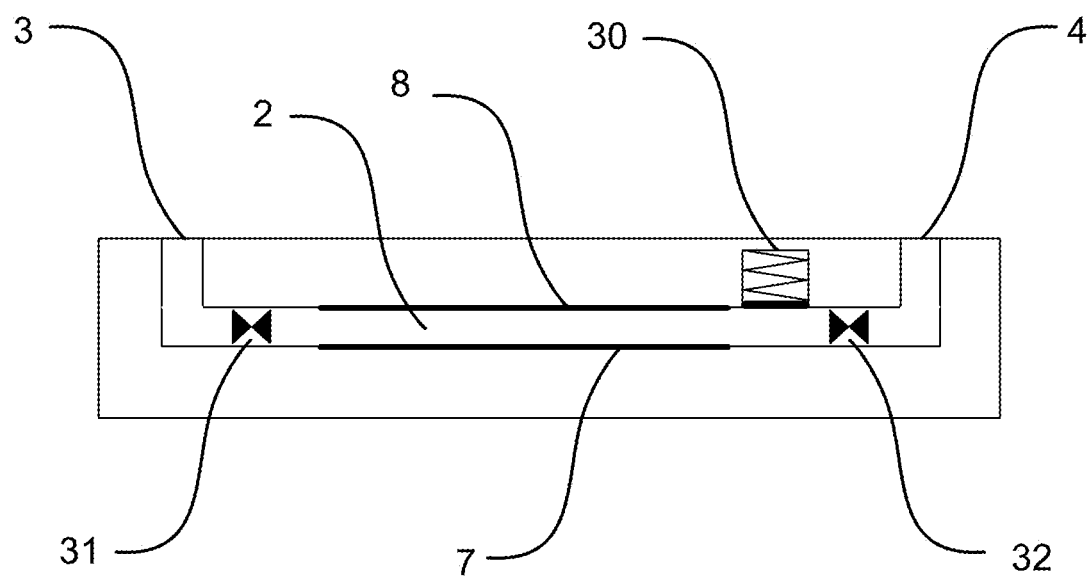
FIG. 10 shows a schematic cross-sectional view of the electrical sample processing device, which has been equipped with a pressure regulation capability.

Referring to FIG. 10, an example embodiment of a channel device is illustrated which incorporates such a pressure regulation mechanism (for example, an active pressure regulation mechanism, or a passive pressure regulation mechanism). The device, similar in other respects to devices described earlier, has a shutoff valve 31 at the inlet port 3 and a shutoff valve 32 at the outlet port 4 section of the channel. In addition, a pressure regulation mechanism 30 is in fluid communication with the channel 2 between the inlet and outlet shutoff valves. This pressure regulation mechanism can be of the form of any such back pressure regulators or pressure relief valves well known in the art and is represented here by a spring loaded plunger and expansion cavity.

In one example embodiment, the pressure regulation device is a spring-loaded plunger or membrane where the spring is preloaded such that the regulator activates at a pre-determined minimum pressure which corresponds to the desired superheated fluid temperature. When this minimum pressure is reached in the channel as a result of heating of the fluid, the plunger will move into the expansion chamber, expanding the effective channel volume in response to a further increase in pressure. If the spring constant is sufficiently low and a sufficiently large expansion cavity is provided, the pressure will be maintained approximately at a constant peak value and a saturated liquid state will be achieved in the fluid when a requisite amount of energy is supplied to the channel. With further energy input a phase transition will occur in the region of the channel which has achieved the liquid saturation state and a mixed liquid-vapour phase will be generated at approximately a constant temperature.

In an alternate embodiment the spring may have no pre-force and the spring stiffness may be chosen such that the pressure increases with temperature but at a rate which allows the liquid to reach saturation at a pre-determined temperature. Thus the resulting temperature will not be constant but will be controlled or will be responsive to applied voltage in a pre-determined manner.

An example of this later embodiment is a membrane of pre-determined stiffness either as part of the whole of one or both of the channel walls or one or more of the walls of a sealed cavity in fluid communication with the channel. A further example of this embodiment is a cavity or channel which is separated from the main channel by a gas-permeable membrane allowing the transport of gas but not liquid. Thus the compressibility of the air or gas will provide the compliance to control the pressure in the manner described.

In yet another embodiment, the device may include an active pressure regulation mechanism that is externally controllable. Such an active pressure regulation device may be controlled such that the pressure is regulated within the channel in synchronization with the timing of the applied voltage. In another example, the device may include both a controllable pressure regulation device and a pressure sensor, where the pressure sensor signal is provided as an input (feedback) signal to a controller, and where the controller is interfaced with the pressure regulation device for controlling the pressure within the channel.

In general, the device can be designed to operate over a wide range of ionic strengths. However, high ionic strength, such as ionic strength above approximately 1 mM, generally requires circuitry capable of delivering higher currents. This results in higher electrical power requirements with its added complications. Therefore, reducing the ionic strength may be performed prior to the application of the voltage.

Figure 4C:
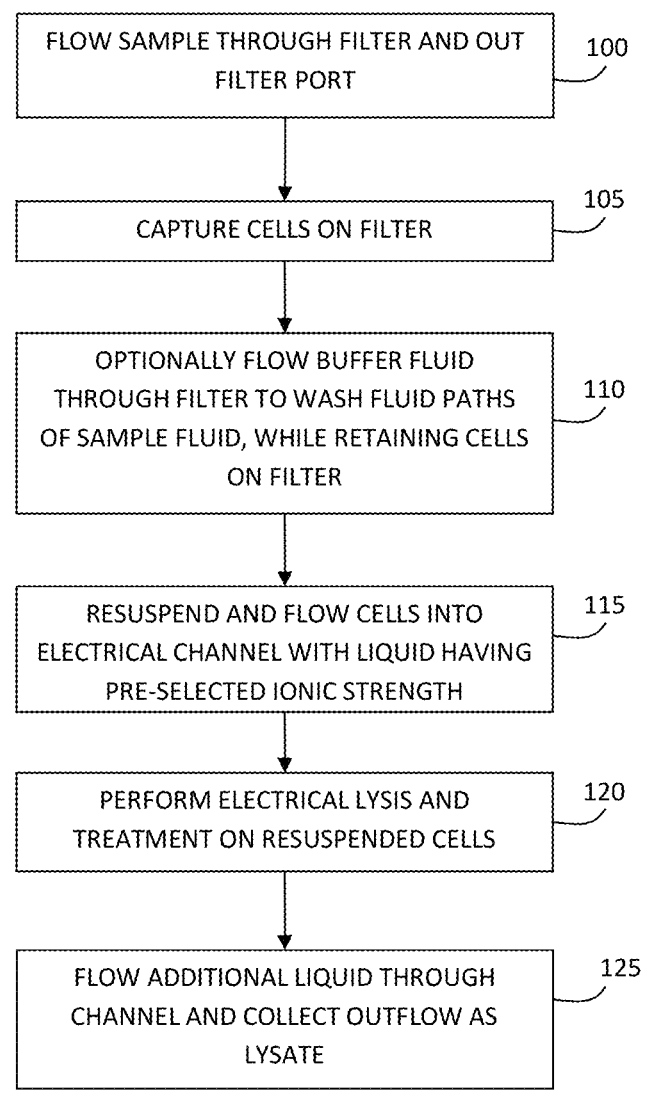
FIG. 4(C) provides a flow chart illustrating a method of electrical processing of cells within a liquid.

The reduction in ionic strength may be readily accomplished in cases where the sample liquid includes cells by filtering the cells as shown in FIG. 3 and FIG. 4 and flowing a low-ionic strength liquid into the channel prior to electrical processing. FIG. 4(C) provides a flow chart that illustrates a method of performing electrical processing of cells after initially capturing the cells on a filter as described in FIG. 4. In step 100, a sample liquid is flowed (such as from a first port 3 to a second port 34 in FIG. 4), through the filter (such as filter 33 in FIG. 4). Cells within the liquid sample are captured by the filter, as described in step 105. After having captured the cells an additional liquid is optionally flowed through the filter to wash the cells and fluid paths of the sample fluid, as in step 110. Then a fluid suitable for performing electrical lysis and treatment and optionally appropriate for downstream processes is flowed to resuspend the cells and carry them to the electrical channel as in step 115. After having carried the cells to the electrical channel suspended in this liquid, the electrical processing may be performed, as shown in step 120. Then the lysate may be extracted by flowing the additional liquid through the channel and collecting the outflow as in step 125. After performing the electrical processing step, the ionic strength of the additional liquid residing within the channel may be increased. For example, this may be achieved by adding a salt-containing reagent to the additional liquid, or, in another example, by flowing the additional liquid through an additional channel containing dried salts that can be dissolved to achieve the desired ionic strength.

Figure 11:
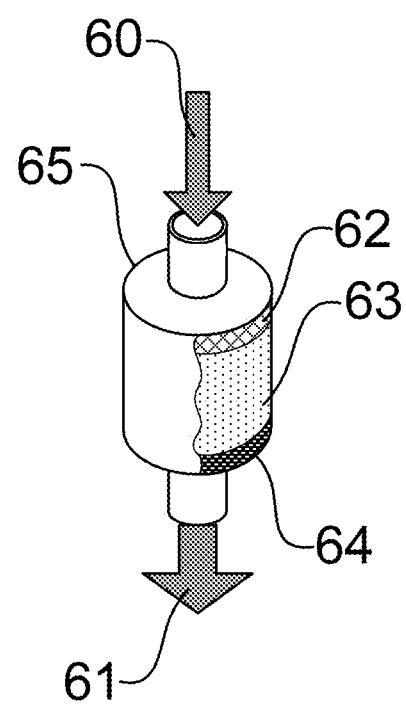
FIG. 11 shows the sample pre-treatment module for reducing ionic content.

In another embodiment, ion reduction in the sample can be performed by the sample cleanup module 65 of FIG. 11 that may be integrated in the inlet port 3 of the device (see FIG. 1) or in a chamber fluidically connected upstream of the inlet port. The sample cleanup module, 6, consists of inlet 60, outlet 61, an optional pre-filter, 62, packed ion exchange resins, 63, and a filter, 64. The optional pre-filter 62 excludes large particles such as cationic exchange resins and non-ionic adsorbing resins, which are employed in some samples such as the blood culture media of the Becton Dickinson blood culturing system.

The ion exchange resins (63) include mixed cationic and anionic resins which serve to deionize the sample, and to optionally capture smaller ionic particles that may be present in the sample. In the case of blood culture samples, some blood culture media includes activated charcoal and fuller's earth powder, for example, as in the BioMerieux system. The filter 64 retains the ionic resins and bound ions and ionic particles to prevent them from entering the device.

For the deionization of ions and ionic particles, mixed $H^+$ form cation exchange resin and $OH^-$ form anion resin may be used. In a specific example involving $Na^+$ and $Cl^-$ ions in solution, $Na^+$ in the medium binds to the cation resin in exchange of $H^+$ and $Cl^-$ binds to the anion resin in exchange of $OH^-$. Removed $H^+$ and $OH^-$ will form water molecules.

This method is widely applied in water deionization applications. In one example implementation, microporous gel resins with the pore size larger than the size of bacteria may be used. In addition, in applications involving bacteria, negatively charged bacteria can still bind to the surface of the anionic resin and nonspecifically bind to the surface of the resins, and this may be prevented by treating both types of resins with a non-ionic surfactant such as TritonX-100. Examples of mixed resins are Amberlite MB-150 from Rohm & Hass and Dowex-Marathon MR-3 from Dow Chemicals with particle sizes ranging from 500-700 µm.

The operation of the ion reduction device is henceforth described by referring to FIG. 3, as applied for treating a urine sample containing bacterial cells for obtaining an assay-ready lysate for a 16S rRNA hybridization assay. Once the entire sample liquid has passed through the channel and the suspended cells are retained on the membrane filter (i.e. concentrated on the filter) an optional washing step can be performed by injecting a washing liquid into the channel. The flow of the washing liquid carries away excess ions (e.g. this step achieves sample cleanup). The channel may then be filled with a low ionic strength liquid, such as a 0.5 mM phosphate buffer.

The release of cellular contents is accomplished by applying a pulse train to the electrodes, thereby causing the electrical lysis. Amongst the released cell contents are ribosomes that contain 16S rRNA entangled with ribosomal proteins. In one embodiment, the electrical pulses are applied such that the combined action of the persisting pulses and flash heated medium untangles/denatures rRNA from the proteins, possibly by denaturing the ribosomal proteins. Furthermore, flash heating of medium may also play a role in achieving a re-conformation of the rRNA molecule that is appropriate for hybridization assays. Moreover, the RNAse enzymes may also be deactivated via the electrical treatment mechanism described above involving electric field effects and flash heating. Finally, a pressure differential may be applied to the channel to deliver the lysate through the outlet port to a downstream chamber where an assay may be performed. Prior to performing a hybridization assay, the ionic strength of the lysate may be increased to a suitable level. As noted above, this may be achieved by adding a salt-containing reagent to the lysate, or, in another example, by flowing the lysate through a channel containing dried salts that can be dissolved by the lysate to achieve the desired ionic strength.

As noted above, the present devices and methods may be employed for a wide range of diagnostic methods and other sample processing applications. In some example applications, the electrical lysis and electrical treatment steps may be performed in a single step, where a cell is lysed and the lysate is treated. Alternatively, electrical lysis may be initially performed, where the electrical parameters of the electrical lysis steps are selected to provide efficient lysis. Electrical treatment of the lysate may then be provided in a subsequent step, where the electrical parameters of the electrical treatment step are chosen to provide efficient or sufficient electrical treatment.

In other example implementations, the sample may be delivered to the channel in the form of a lysate based on a preceding or separate lysis step. Alternatively, the sample may contain molecules that are to be treated according to the aforementioned electrical treatment methods, but where the molecules may not originate from a preceding lysis step.

In one example implementation, the devices and methods may be employed for applications involving the rapid lysis of bacteria and the preparation of the lysed bacteria for PCR. In particular, the present methods may be employed as a sample preparation method for colony PCR, in which PCR is employed to screen transformed bacterial colonies with successful incorporation of a gene insert into a plasmid. The present electrical treatment methods may be employed to denature or deactivate PCR inhibitors and/or contaminants, such that PCR may be performed without performing a previous nucleic acid extraction or purification step. For example, bacteria obtained from a bacterial colony may be suspended in a low ionic strength buffer and provided to a device as described above, such that the buffer is flowed into the channel. A suitable voltage pulse train is then applied to obtain lysis and electrical treatment of the lysate (example suitable values are provided in the preceding disclosure). The processed lysate may then be directly mixed with the appropriate PCR reagents for performing direct PCR.

In another example application, the present electrical treatment method may be employed for the denaturing of enzymes used for nucleic acid digestion or modifications. The present devices and methods may be employed for the electrical treatment of a sample in order to denature or deactivate the enzymes. It is to be understood, however, that the effectiveness of this method may be limited by the ionic strength of the sample, and the ability to employ ion exchange resins for the deionization of samples. The electrical parameters required for a specific enzyme inactivation without compromising the integrity of the nucleic acid may be determined by performing a series of experiments.

Suitable values for the various parameters employed in electrical lysis and treatment will depend on the properties of the liquid, cells, and macromolecules of interest that are to be processed in the device. Suitable values may also depend on the application. For example, in some applications, in may be preferable to lyse a cell and release intracellular macromolecules (such as nucleic acids or proteins) without causing substantial denaturing or degradation. In such a case, an electrical processing protocol may be preferred in which the thermal environment, electric field, and timescale of treatment are chosen to lyse the cells without denaturing or degrading the macromolecules.

In other applications, may be preferable to lyse a cell and release selected intracellular macromolecules (such as nucleic acids) while causing substantial denaturing or degradation of other intracellular macromolecules that are released (such as a nuclease). In such a case, a different electrical processing protocol may be preferred in which the thermal environment, electric field and timescale of treatment are chosen to lyse the cells and to denature or degrade the other macromolecules.

Generally speaking, the following ranges may be employed for electrical processing of cells. The electric field strength within the channel that is produced by the application of the voltage pulses may range between approximately 200 V/cm<E<50 kV/cm, depending on the type of cell that is to be processed and the degree of electrical processing that is desired. A range of approximately 2 kV/cm<E<30 kV/cm may be preferable for lysis of microorganisms and using the lysate for performing diagnostic tests on the released nucleic acids.

According to different example implementations, the pulse width of individual voltage pulses may range between approximately 1 µs<$t_p$<10 ms, depending on the type of cell that is to be processed and the degree of electrical processing that is desired. A range of approximately $t_p$<1 ms may be preferable for avoiding the electrical breakdown of the dielectric coating in the case of blocking electrodes, minimizing the accumulation of the electrochemical products in the case of non-blocking electrodes. A range of approximately $t_p > 10$ μs is preferred for lowering the high frequency demands of driving electronics.

According to other example implementations, the time duration over which the voltage pulses are applied may be less than about 5 s, depending on the type of cell that is to be processed and the degree of electrical processing that is desired. In some cases, such as to minimize the heat induced degradation of target macromolecules and decrease the power demands of the driving electronics, an effective time duration for electrical processing may be less than about 100 ms.

According to other example implementations, the ionic strength of the cell containing liquid may range from approximately 0.1 mM<I<100 mM, depending on the ionic composition of the initial sample that is to be processed and the degree of electrical processing that is desired. In some cases, when filtering is used and fluid exchange is allowed, a more suitable range for the ionic strength may be from approximately 0.1 mM<I<10 mM, or 0.2 mM<I<1 mM.

According to other example implementations, the peak temperature of the liquid within the channel during the application of voltage pulses may range from approximately 30° C.<$T_p$<250° C., depending on the type of cell that is to be processed and the degree of electrical processing that is desired. In some applications, such as lysis of microorganisms and using the lysate for performing diagnostic tests on the released nucleic acids, it may be preferable for the temperature range to lie within approximately 80° C.<$T_p$<200° C.

The heating rate of the liquid for the electrical processing may be greater than approximately 250° C./s, depending on the type of cell that is to be processed and the degree of electrical processing that is desired. In some cases, such as lysis of Gram positive bacteria, fungi, and spores, a suitable range may include rates greater than about 2000° C./s.

The cooldown time of the liquid following electrical treatment may be less than approximately 1 s, depending on the thermal sensitivity of the target macromolecule. In some cases, such as when the target macromolecule is particularly sensitive, a preferred range may include times below about 100 ms.

As described above and in the forthcoming examples, the present devices and electrical processing methods may be employed for the preparation of a wide variety of sample types. In many cases, a wide variety of cell types may be processed with the same device properties, but with different electrical parameters and/or pressure regulation during electrical processing. Specific types of cells are considered briefly below.

The preceding ranges of parameters are provided as examples and are not intended to limit the scope of the disclosure. It will be understood that those skilled in the art, aided by the present disclosure, may identify additional suitable ranges or combinations of parameters by routine experimentation.

In the examples which follow, the pulse train consisted of a number, n, of bipolar square pulse cycles with a frequency of 10 or 20 kHz. Three types of channels with the following dimensions (H×W×L) were utilized: 0.1×6.4×28 mm³ (wide-long, with a volume of about 18 μl), 0.1×6.4×16 mm³ (wide, with a volume of about 10 μl) and 0.1×3.2×28 mm³ (narrow, with a volume of about 9 μl). The sets of pulse amplitude, V, the train duration, t, and the ionic strength are known as test parameters in the context of this disclosure.

The following examples are presented to enable those skilled in the art to understand and to practice embodiments of the present disclosure. They should not be considered as a limitation on the scope of the present embodiments, but merely as being illustrative and representative thereof. The examples may also serve to provide example and/or suitable ranges of parameters that for the operation of the device in various applications.

Example 1: Deactivation of Enzymes

The experiments described in this example are intended to demonstrate the effects of electrical and thermal parameters on the capacity of the device for altering the structure and function of proteins by demonstrating deactivation (complete or partial) of selected example enzymes. The experiments demonstrate an aspect of the electrical treatment function and capability of the devices disclosed herein, involving the modification of protein conformation.

A mixture of three enzymes, glucose-6-phosphate dehydrogenase (G6PDH) (G-8629, Sigma) 1 unit/mL, beta-glucuronidase (G-7396, Sigma) 100 units/mL and horseradish peroxidase (HRP) 1:500,000 dilutions (A-0168, Sigma) were prepared in 0.1 and 0.4 mM phosphate buffer pH 7.4. The sample volume of 200 μL was passed through a narrow channel in steps of 5 μL at intervals of 10 s during which a single pulse train, with amplitude of 150 V and frequency of 10 kHz, was applied.

The treated sample was tested for the enzyme activity compared to the untreated sample. The enzyme activity was measured using the respective substrates; glucose-6-phosphate (G6P) 6.6 mM, nicotinimide adenine dinucleotide (NAD) 4.0 mM, sodium chloride 90 mM, bovine serum albumin (BSA) 1%, sodium azide 0.09% in Tris 20 mM pH 5.0 for G6PDH, 4-Nitrophenyl 3-D-glucuronide (N-1627, Sigma) 1 mM in 50 mM phosphate buffer pH 7.4 for Glucuronidase and 3, 3',5,5'-Tetramethylbenzidine (TMB) followed by stop solution for HRP. The absorbance was measured at 340 nm, 405 nm and 450 nm respectively.

Figure 12A:
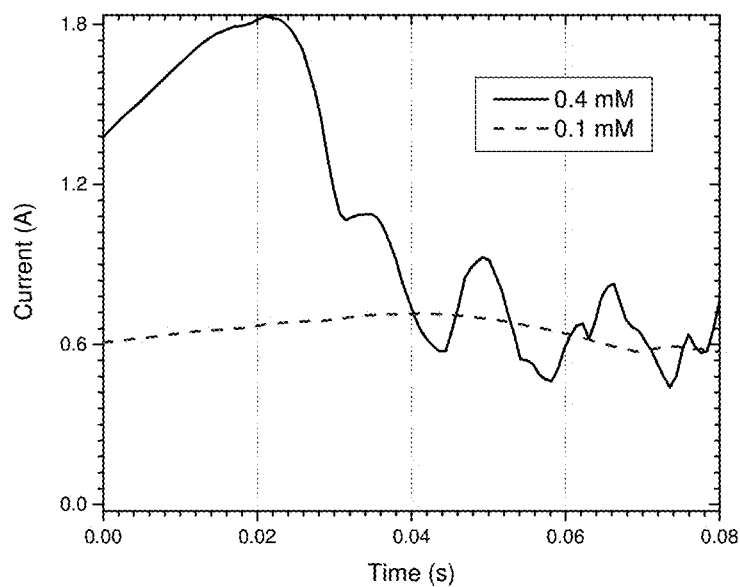
FIG. 12(A) shows the measured current envelope for the channel in which the enzyme suspensions were subjected to electrical treatment.
Figure 12B:
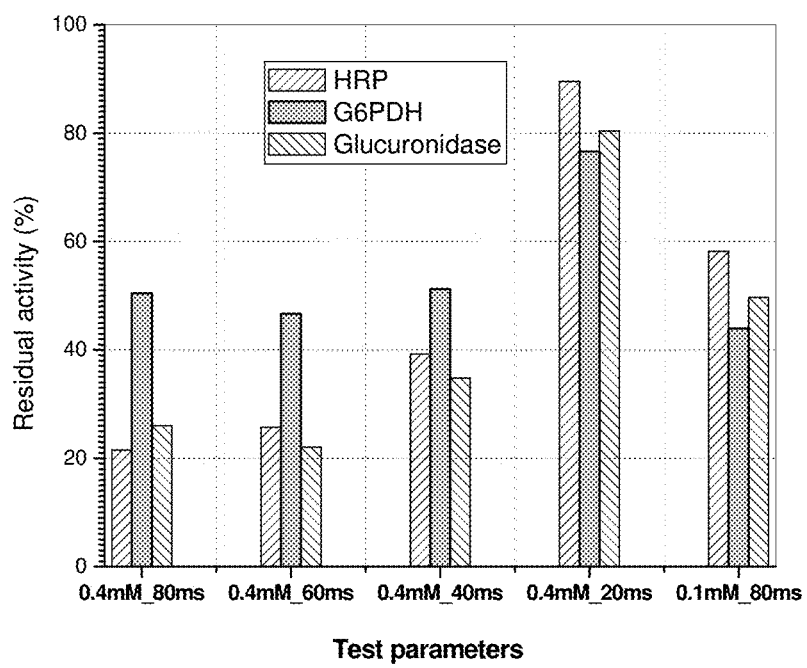
FIG. 12(B) shows the measured residual enzyme activity following the electrical treatment with different test parameters.

The current envelopes corresponding to different ionic strengths are presented in FIG. 12(A). The residual enzyme activities, for different combinations of pulse train durations and ionic strengths are presented in FIG. 12(B). As it is observed the enzyme activity undergoes a drastic reduction for train durations exceeding the critical duration, $t_c$, of about 40 ms. The results suggest that the residence time after $t_c$ does not have a pronounced effect on the enzyme activity reduction beyond this time duration. In the case of lower ionic strength of 0.1 mM, even though the critical time $t_c$ at approximately 70 ms has been passed, the activity reduction is moderate, implying a possible correlation between heating rate and enzyme deactivation.

Example 2: Electrical Lyslis of *Escherichia coli*

The experiments described in this example are intended to demonstrate the effects of the electrical parameters on the efficiency of the device for lysing *E. coli* cells. NEB 5-alpha competent *E. coli* cells, transformed with pUC19 plasmid which contains ampicillin resistance gene and beta-galactosidase gene, were grown on LB agar plates supplemented with 100 μg/mL Ampicillin, 60 μg/mL X-gal and 0.1 mM isopropylthio-β-D-galactosidase (IPTG). A single blue colony of *E. coli* was cultured in LB broth supplemented with 100 μg/mL Ampicillin overnight at 37° C. The cells were centrifuged at 7000 rpm for 5 min. The cell pellet was washed twice and re-suspended in 0.1 to 0.4 mM phosphate buffer pH 7.4 at a concentration of 0.5 to 1×10⁹ CFU/mL.

To perform electrical lysis, 200 µL of the sample was passed through a channel in steps of 5 µL every 10 s. Then, three different analytical tests were performed for assessing the efficiency of cell lysis; total protein assay, quantitative total nucleic acid assay, and 16S rRNA hybridization assay.

Figure 13:
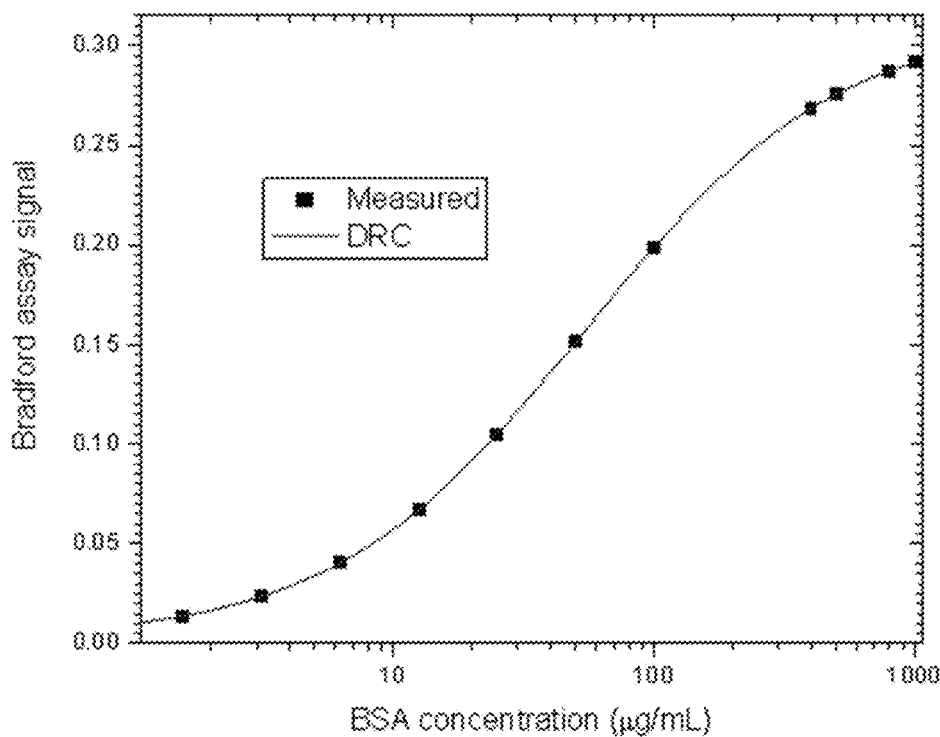
FIG. 13 illustrates the dose response curve of Bradford protein assay determined by assaying BSA standards.

Total protein released in the cell lysate was assayed by Bradford Reagent (B-6916, Sigma). The cell lysate was centrifuged at 7000 rpm for 5 min and 50 µL of the supernatant was mixed with an equal volume of Bradford protein assay reagent. The color development was measured by spectrophotometer at absorbance 595 nm. As a reference cell lysis control, cells were lysed mechanically by beating with an equal volume of glass beads (106 µm, Sigma) for 2 min and the supernatant of glass bead cell lysate (GB) was assayed after centrifugation. The protein concentration was calculated by referring to the dose response curve of FIG. 13, which has been prepared by running Bradford assay on different concentrations of BSA.

To measure the released nucleic acid quantitatively, the cell lysate was centrifuged at 7000 rpm for 5 min and 50 µL of the supernatant was mixed with an equal volume of SYTO-9 nucleic acid stain (S-34854, Invitrogen), 2.5 µM concentration in 0.1 mM phosphate buffer pH 7.4. The fluorescence signal was measured by fluorospectrophotometer at excitation wavelength 485 nm and emission wavelength 515 nm.

Bacteria-specific 16S rRNA in the cell lysate was detected by a solid-phase sandwiched nucleic acid hybridization assay. Although total cell lysate can be used as an assay-ready sample, to demonstrate the efficient release of rRNA out of the cells, the supernatant of the cell lysate was used in the assay. The cell lysate was centrifuged at 7000 rpm for 5 min to collect the supernatant containing released rRNA. The supernatant of 50 µl volume was added to Immobilizer Amino plate (Nunc) assay wells, in which 5 µM of biotinylated capture probe and 20 µg/mL streptavidin (R1) were immobilized by spotting and non-specific binding sites were blocked with 0.2% BSA and 0.1% Tween-20 in PBS pH 7.4. R2 reagent, 0.2 µM FITC-conjugated detector probe in 1 M phosphate buffer pH 7.4, of 50 µL volume was added to the assay well and incubated at 55° C. for 20 min. After washing, 100 µL of R3 reagent, 1:1000 dilution of HRP-conjugated anti-FITC antibody in the blocking buffer, was added to the well and incubated at room temperature for 10 min. TMB substrate of 100 µL volume was added after washing followed by addition of the stop solution. The color development was measured by spectrophotometer at 450 nm wavelength.

Example 2.1 Effects of Pulse Amplitude on Electrical Lysis Efficiency

Figure 14A:
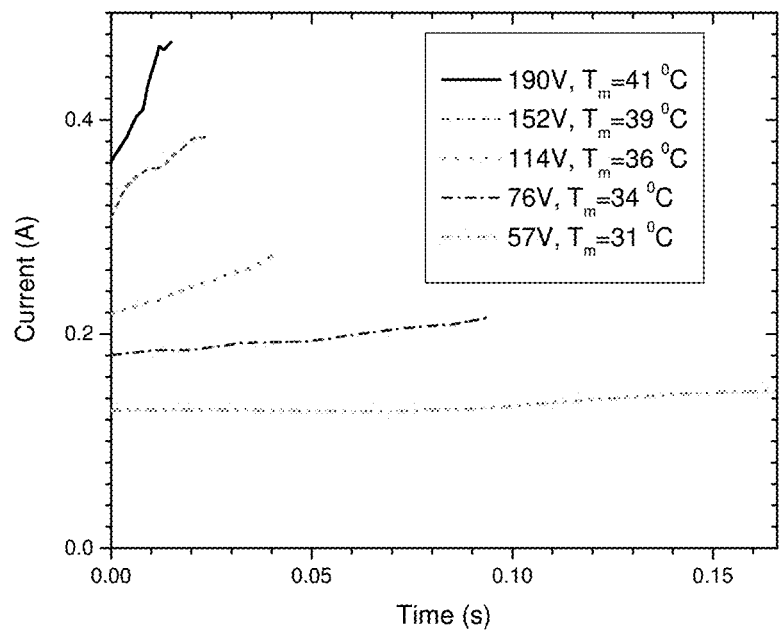
FIG. 14(A) shows the measured current envelope for the channel in which E. coli suspension underwent electrical lysis under different test

The bacteria suspension of $5 \times 10^8$ CFU/mL in 0.1 mM phosphate buffer pH 7.4 was passed through a narrow channel in steps of 5 µL/10 s and 10 kHz pulse trains with different durations and amplitudes were applied to the suspension. The duration, t, and amplitude, V, of any two different parameter sets, $(t_1, V_1)$ and $(t_2, V_2)$, were related by $t_1/t_2 = (V_2/V_1)^2$ to ensure nearly equivalent electrical power delivery to the channel for both cases. Moreover, besides selecting low ionic strength of 0.1 mM, the durations were chosen short enough not to heat up the liquid much above the biological temperatures. The average temperature of the channel achieved, $T_m$, was estimated and recorded on the legend of FIG. 14(a), which illustrates the current envelope for different test parameters.

Figure 14B:
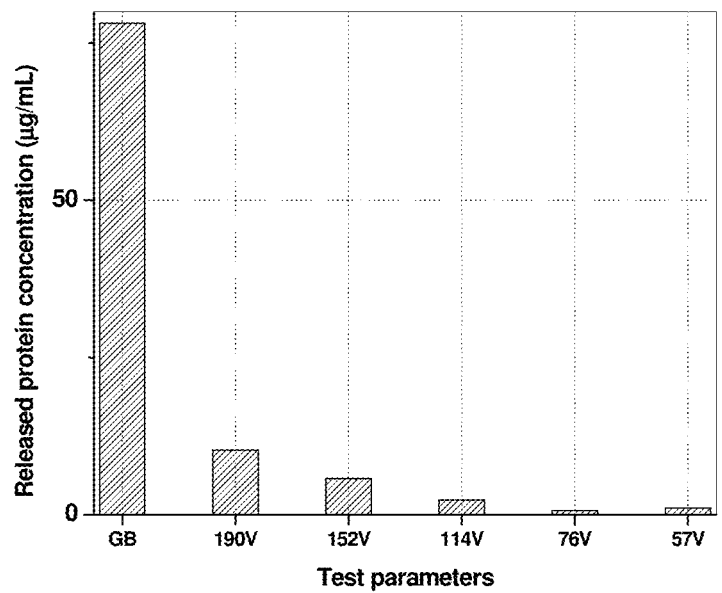
FIG. 14(B) shows the effects of pulse amplitude on the electrical lysis performance of the device as determined by quantifying the release of proteins from E. coli cells.
Figure 14C:
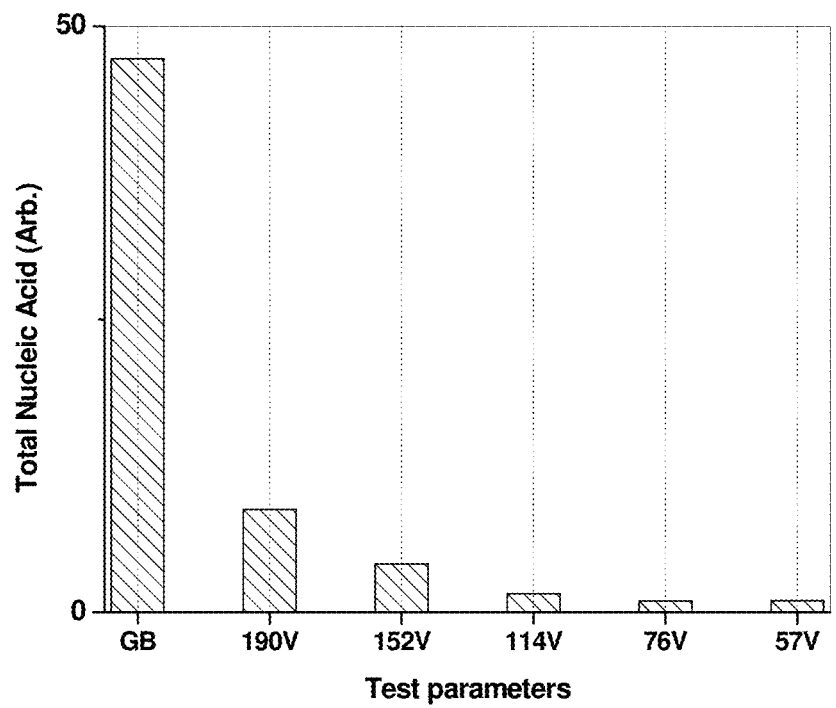
FIG. 14(C) shows the effects of pulse amplitude on the electrical lysis performance of the device as determined by quantifying the release of nucleic acids from E. coli cells.
Figure 14D:
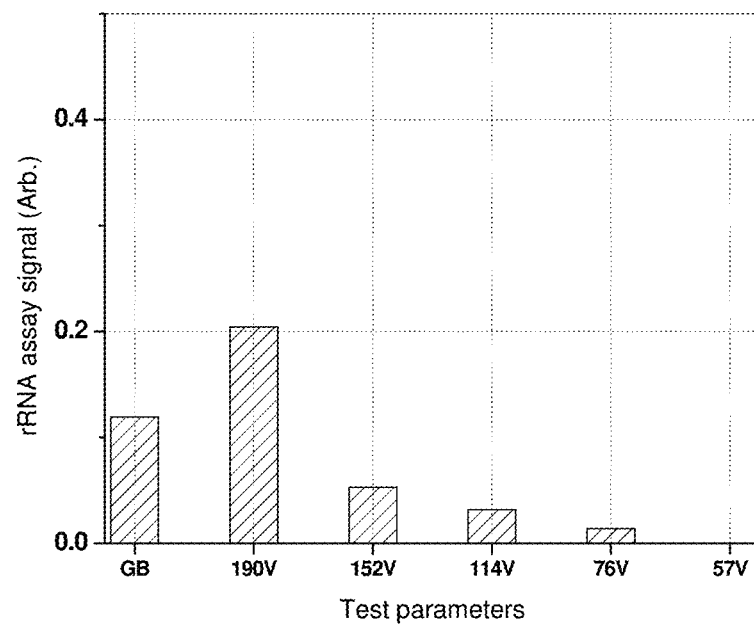
FIG. 14 (D) shows the effects of pulse amplitude on the electrical lysis performance of the device as determined by measuring the hybridization of 16 rRNA released from E. coli cells to specific probes.

The results of 3 analytical assays; detections of total protein, total nucleic acid and 16S rRNA, are presented in FIGS. 14(b)-14(d). Though the amplitude has a deterministic effect on the release of the intracellular materials, the level of lysis as judged by total protein and nucleic acid release is much lower than the case of the comparative method of GB lysis. However, in the case of the 16S rRNA assay, despite less efficient total nucleic acid release, higher signal of 16S rRNA was detected for electrical lysis (with 190 V) compared to the GB lysis. This finding indicates the significance of the accessibility of the specific hybridisation region on the rRNA in addition to the rRNA concentration in the cell lysate. The capability of the electrical method to modify macromolecular conformation appears to provide more effective assay-ready cell lysate preparation for rRNA assays.

Figure 15A:
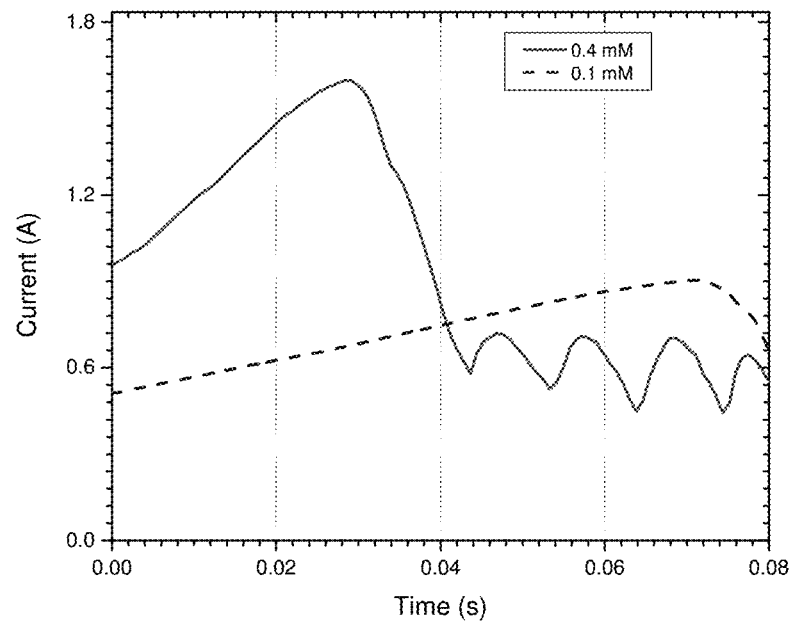
FIG. 15(A) shows the measured current envelope for the channel in which E. coli suspension underwent electrical lysis under different test parameters and constant pulse amplitude.

Example 2.2 Effects of Train Duration and Ionic Strength on Electrical Lysis Efficiency The bacteria suspension of $1 \times 10^9$ CFU/mL in 0.1 or 0.4 mM phosphate buffer pH 7.4 was passed through a narrow channel in steps of 5 µL/10 s and 10 kHz and 155 V pulse trains with different durations were applied to the suspension. The current envelopes are presented in FIG. 15(a).

Figure 15B:
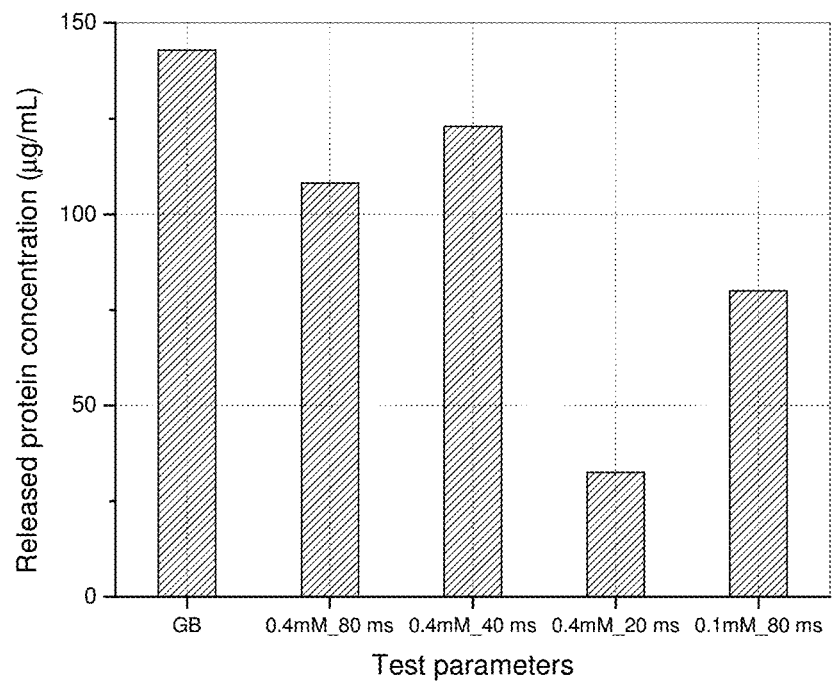
FIG. 15(B) shows the effects of train duration and ionic strength on the electrical lysis performance of the device as determined by quantifying the release of proteins from E. coli cells.
Figure 15C:
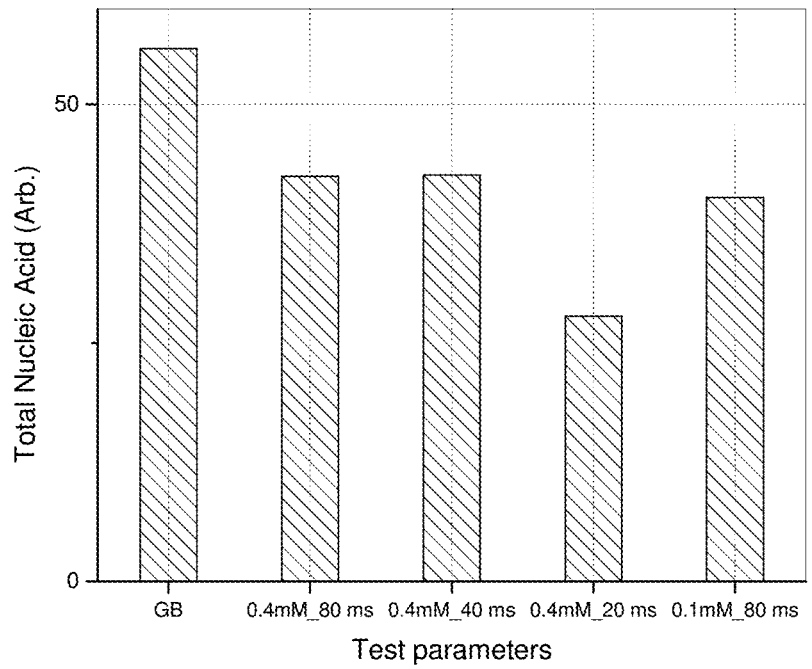
FIG. 15(C) shows the effects of train duration and ionic strength on the electrical lysis performance of the device as determined by quantifying the release of nucleic acids from E. coli cells.
Figure 15D:
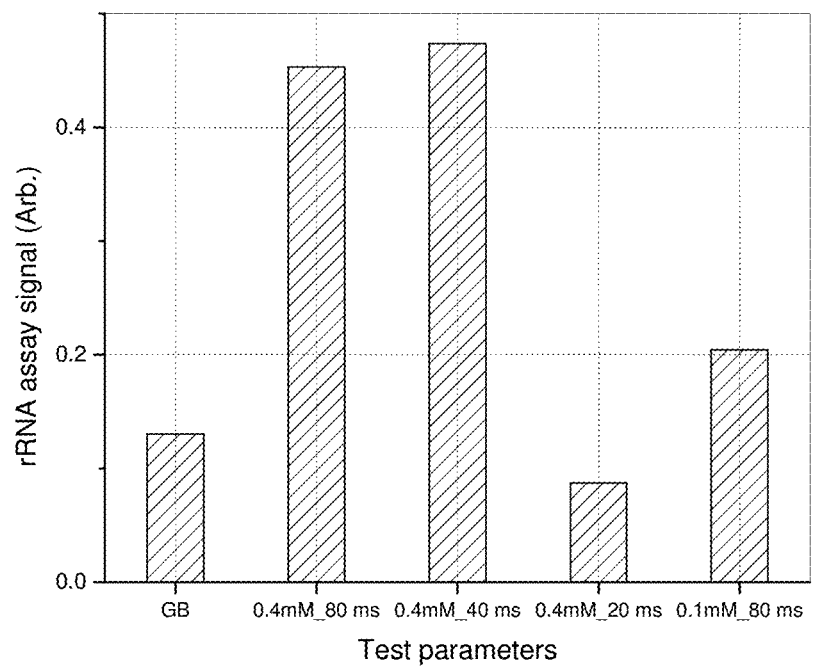
FIG. 15(D) shows the effects of train duration and ionic strength on the electrical lysis performance of the device as determined by measuring the hybridization of 16S rRNA released from E. coli cells to specific probes.

The results of 3 analytical assays are presented in FIG. 15(B)-15(D). In general, the release of intracellular materials increases drastically when the train duration is close to the critical duration $t_c$. In the case of 0.1 mM ionic strength, though the pulse duration approaches $t_c$, the level of released molecules is well below the corresponding case of higher ionic strength. This implies that the heating rate may have a deterministic effect on the electric lysis and treatment.

Example 2.3 the State of Proteins in the Electrically Prepared Lysate

Figure 15E:
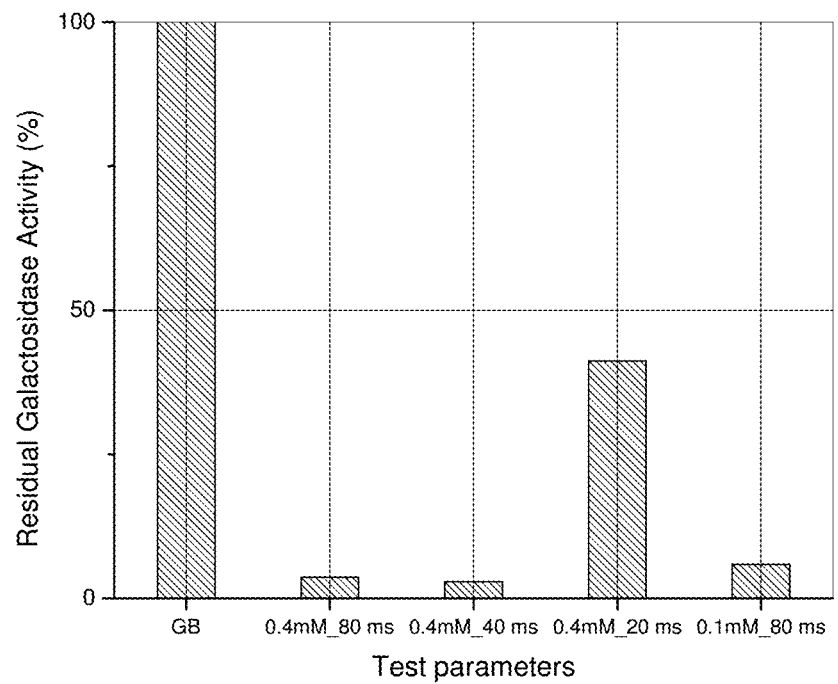
FIG. 15(E) shows the effects of train duration and ionic strength on the activity of E. coli cells-associated beta-galactosidase after electrical lysis.

In order to demonstrate the action of electrical treatment on the biomolecules, the activity of the endogenous enzyme beta-galactosidase, expressed by the pUC19 plasmid vector, was measured. To detect the enzyme activity of beta-galactosidase, the cell lysate of the previous example was centrifuged at 7000 rpm for 5 min and 50 µL of the supernatant was mixed with an equal volume of 2-Nitrophenyl β-D-galactopyranoside (N-1127, Sigma) 4 mg/mL in 0.1 mM phosphate buffer pH 7.4. The color development was measured by spectrophotometer at absorbance 420 nm. The measured residual enzyme activity, normalized to the activity in the case of GB lysis, is presented in FIG. 15(E). Again, the increase in the train duration close to and beyond $t_c$ have a significant effect on the deactivation of the enzyme. This finding indicates that electrical lysis modifies the conformation of macromolecules.

Example 2.4 the State of Nucleic Acids in the Electrically Prepared Lysate

To assess the spectrum of different types of nucleic acids released by electrical lysis, in the example of section 2.2, the cell lysates were centrifuged at 10000 rpm for 5 min and the nucleic acids in the supernatants were resolved by gel electrophoresis on 0.5% agarose gel in 0.5×TBE buffer and 0.5 µg/mL ethidium bromide (EtBr) at 150 volts for 45 min. The release of genomic DNA, plasmid DNA and total RNA by electrical lysis was shown in FIG. 15(F).

In comparison with GB lysis, the released genomic DNA by electrical lysis was mainly observed as a slower mobility band with less fluorescence intensity. To further clarify this observation, electrical treatment was applied to the purified genomic DNA prepared by using GenElute Bacterial Genomic DNA kit (NA2100, Sigma) and the results were shown in FIG. 16.

DH5-alpha competent *E. coli* cells were grown on LB agar plates and a single colony of *E. coli* was cultured in LB broth overnight at 37° C. Following the manufacturer's protocol, the cells were pre-treated with RNase A and Proteinase K solutions prior to the addition of cell lysis solution and incubation at 55° C. for 10 min. The genomic DNA, purified by using a spin column and eluted in nuclease-free water, was re-suspended in 0.2 mM phosphate buffer pH 7.4 to an equivalent concentration of $0.5 \times 10^9$ CFU/mL.

Purified genomic DNA was passed through a wide and long channel in steps of 10 μL/10 s and electrically treated with train durations of 34 or 44 ms and pulse amplitude of 140 V. The current profile is presented in FIG. 16(*a*). Genomic DNA with or without electrical treatment was resolved by agarose gel electrophoresis and the results are presented in FIG. 16(*b*). The electrical treatment resulted in a mobility shift of genomic DNA as was observed in FIG. 15*f*, indicating the change in conformation of genomic DNA during electrical lysis.

Figure 15F:
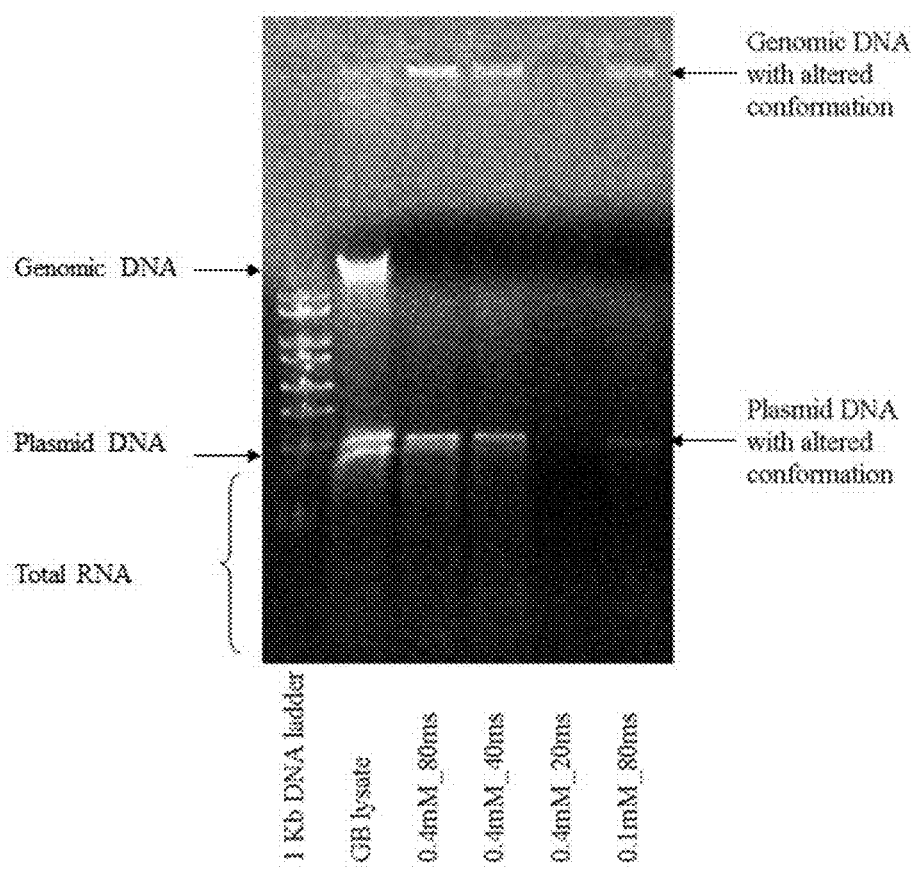
FIG. 15(F) shows the release of nucleic acids from E. coli cells by electrical lysis, visualized after resolving total nucleic acids on agarose gel electrophoresis.

The plasmid DNA released by electrical lysis also was resolved as a slower mobility band in FIG. 15(F). To further clarify this observation, electrical treatment was applied to the purified pUC19 plasmid DNA prepared by using GenElute Plasmid Miniprep kit (PLN10, Sigma)) and the results were shown in FIG. 16.

NEB 5-alpha competent *E. coli* cells, transformed with pUC19 plasmid were grown on LB agar plates supplemented with 100 μg/mL Ampicillin. A single blue colony of *E. coli* was cultured in LB broth supplemented with 100 μg/mL Ampicillin overnight at 37° C. Following the manufacturer's protocol, the cells were lysed in sodium hydroxide lysing buffer and re-suspended in the neutralization/binding buffer. The plasmid, purified by using a spin column and eluted in nuclease-free water, was re-suspended in 0.2 mM phosphate buffer pH 7.4 to an equivalent concentration of $1 \times 10^9$ CFU/mL.

Purified pUC19 plasmid was passed through a wide and long channel in steps of 10 μL/10 s and electrically treated with train durations of 34 or 44 ms and pulse amplitude of 140 V. The current profile is presented in FIG. 16(*a*). Plasmid DNA with or without electrical treatment was resolved by agarose gel electrophoresis and as indicated in FIG. 16(*c*) the electrical treatment results in a mobility shift similar to what was observed following the electrical lysis in FIG. 15(*f*), indicating the change in conformation of plasmid DNA during electrical lysis.

Example 2.5 Capability of the Device to Prepare Sample for Polymerase Chain Reaction (PCR)

This example demonstrates the effectiveness of the electrical treatment action of the device in terms of reducing the inhibitory factors of PCR, enabling direct PCR processing without the need for additional reagents or process. Bacteria-specific 16S rRNA gene (rDNA) was amplified by PCR, using Bacteria Identification Kit (BioChain Institute, Inc.). The experiments were performed by lysing NEB 5-alpha competent *E. coli* cells re-suspended in 0.1 and 0.4 mM phosphate buffer pH 7.4.

Although total cell lysate can be used as an assay-ready sample, to demonstrate the efficient release of genomic DNA out of the cells, the supernatant of the cell lysate was used for PCR. The cell lysate prepared by electrical lysis was centrifuged at 7000 rpm for 5 min and the supernatant containing released genomic DNA was collected. As a reference cell lysis control, cells were lysed mechanically by vortexing with an equal volume of glass beads. PCR reaction was prepared by mixing 1 μL of the cell lysate supernatant, 1 μL of universal control primer mix, 12.5 μL of 2×PCR mix and 10.5 μL of TE buffer. Universal bacteria specific 16S rRNA gene fragment of 475 base pairs was amplified by 1 cycle of 95° C. for 120 seconds, 35 cycles of 95° C. for 30 seconds, 56° C. for 45 seconds and 72° C. for 40 seconds, and 1 cycle of 72° C. for 600 seconds. The resulting PCR product was resolved by gel electrophoresis on 1.2% agarose gel in 0.5×TBE buffer and 0.5 μg/mL ethidium bromide at 150 volts for 30 min.

Figure 15G:
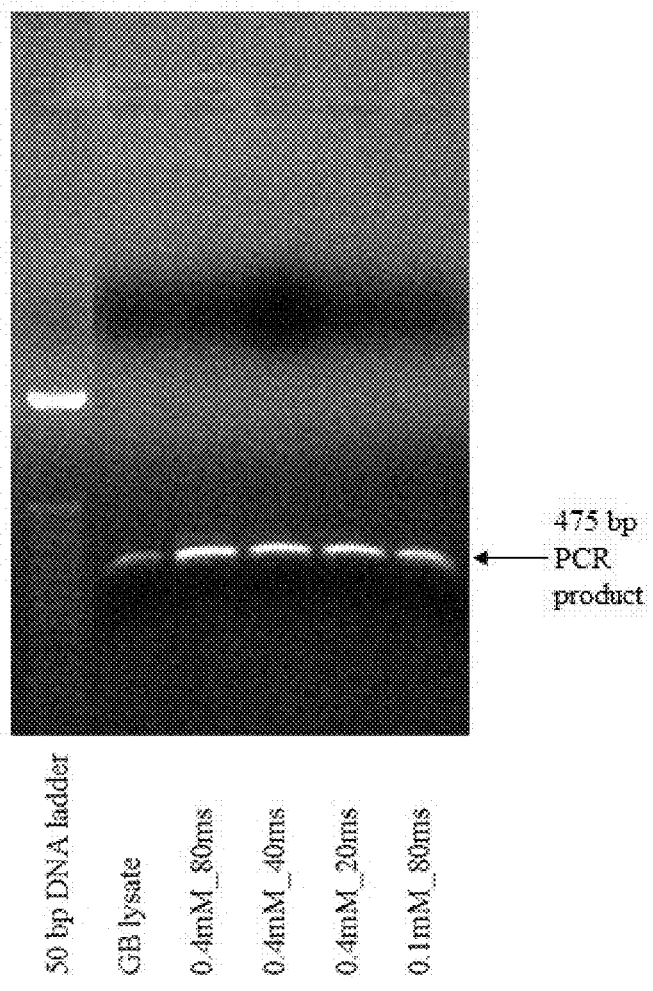
FIG. 15(G) illustrates a downstream application of genomic DNA in the E. coli cells cell lysate prepared by electrical lysis. The supernatant of cell lysate was subjected to PCR amplification of the bacterial 16S rDNA gene fragment. The PCR product was visualized after resolving on agarose gel electrophoresis.

A fragment of 16S rDNA was efficiently amplified from all electrical lysates prepared by different electrical parameters as indicated in FIG. 15(G), but only poor amplification was observed for glass bead lysate.

PCR inhibition effect by the inhibitors associated with cellular components of bacteria is a well known mechanism and this effect is usually overcome by sample dilution or using PCR inhibitor removal kit prior to PCR amplification. When the glass bead lysate was serially diluted prior to PCR reactions as recommended by Bacteria Identification Kit protocol, successful PCR amplification was observed in FIG. 16(*d*), indicating the presence of PCR inhibitory factors in GB lysate. To further demonstrate the capability of PCR-ready sample processing by electrical lysis, electrical treatments were applied to the supernatant of GB lysate with potential PCR inhibitory factors by passing the lysate through a wide and long channel and applying 140 V pulse and 10 kHz trains with duration of 34 or 44 ms, for which the corresponding current profile is presented in FIG. 16(*a*). As shown in FIG. 16(*d*), electrical treatment eliminates PCR inhibition effect present in GB lysate.

Example 2.6 Capability of the Device to Release Intact Plasmid DNA for Downstream Applications This example demonstrates the capability of the device to release plasmid DNA with preserved integrity for downstream applications.

NEB 5-alpha competent *E. coli* cells, transformed with pUC19 plasmid which contains ampicillin resistance gene and beta-galactosidase gene, were cultured in LB broth supplemented with 100 μg/mL Ampicillin overnight at 37° C. The cells were centrifuged at 7000 rpm for 5 min. The cell pellet was washed twice and re-suspended in 0.4 mM phosphate buffer pH 7.4 at a concentration of $1 \times 10^9$ CFU/mL.

As a reference plasmid purification method, pUC19 plasmid was purified using GenElute Miniprep kit (Sigma). Following the manufacturer's protocol, the cells were lysed in sodium hydroxide lysing buffer and re-suspended in the neutralization/binding buffer. During cell lysis, double-stranded nucleic acids of both genomic DNA and plasmid DNA are denatured by the alkaline pH. During neutralization step, although plasmid DNA can re-nature back to double-stranded structure, denatured genomic DNA precipitates and is removed by centrifugation. The plasmid in the supernatant was purified using a spin column and eluted in nuclease-free water. In the case of glass bead or, electrical lysis, the supernatant of the cell lysate was mixed with the neutralization/binding buffer of GenElute Miniprep kit and the purification was continued as the reference plasmid purification method.

Figure 16A:
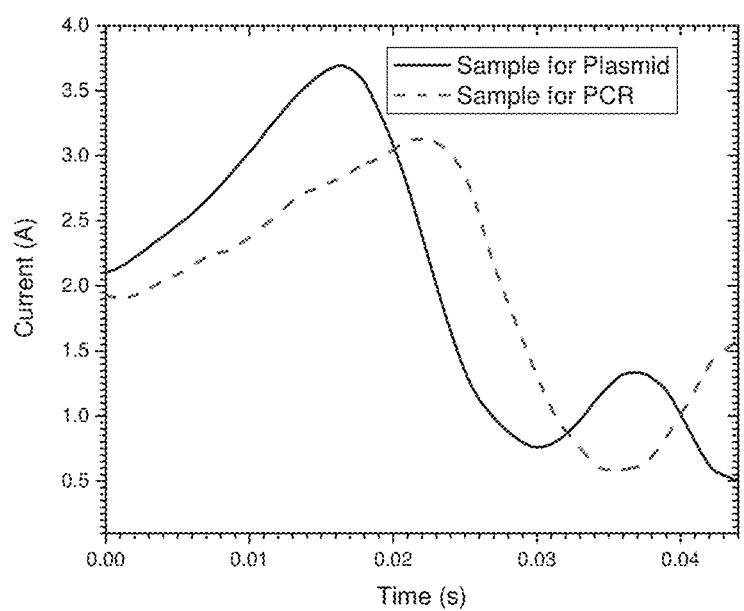
FIG. 16(A) shows the measured current envelopes for the channel in which the purified plasmid DNA and *E. coli* cells GB lysate for PCR were electrically treated.
Figures 16B, 16C:
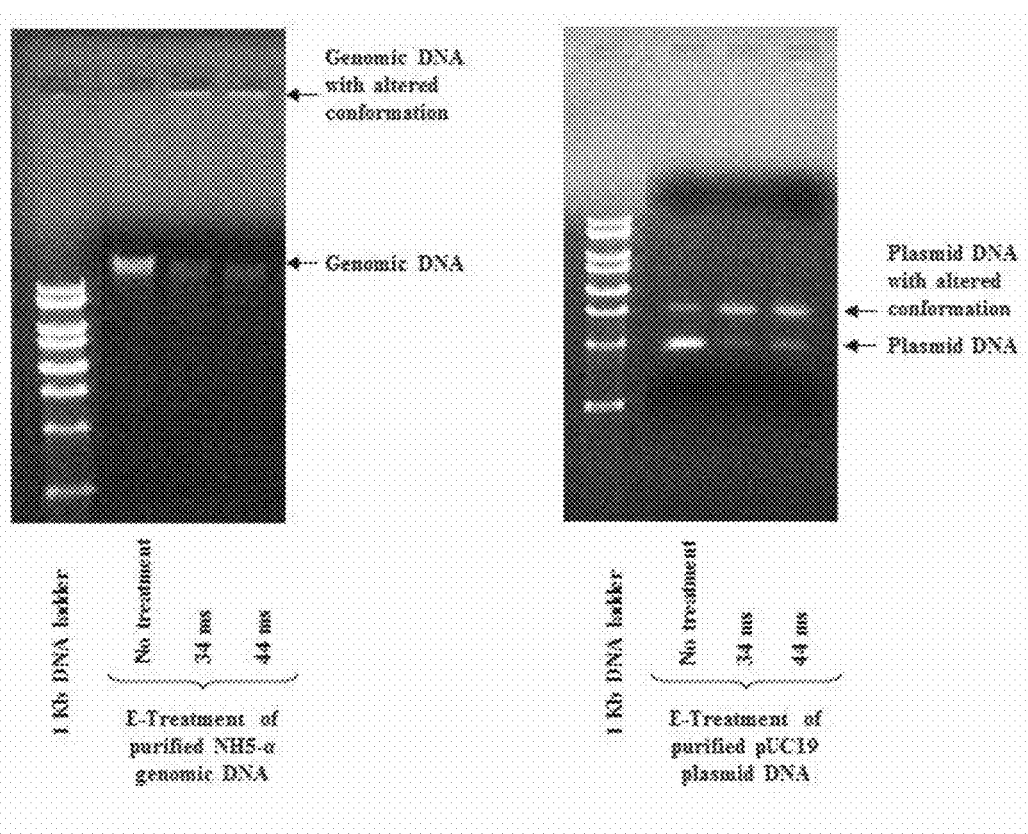
FIGS. 16(B) and 16(C) illustrate conformational change in nucleic acids as a result of electrical treatment of purified NH5-α genomic DNA and purified pUC19 plasmid DNA.
Figure 16D:
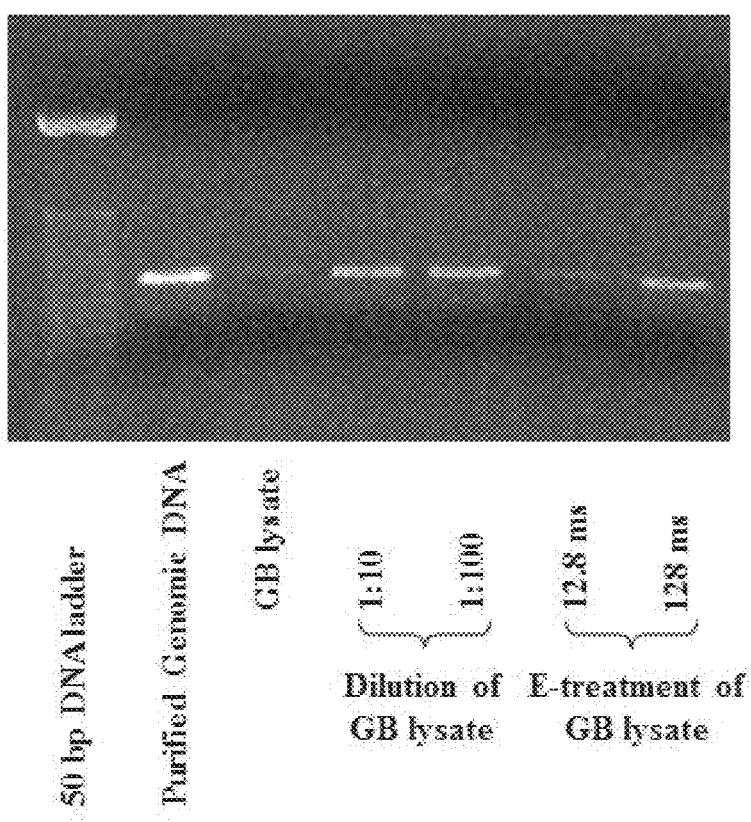
FIG. 16(D) shows PCR-ready quality of cell lysate prepared by electrical treatment. The supernatant of glass bead cell lysate was serially diluted or electrically treated prior to PCR amplification of the bacterial 16S rDNA gene fragment. The PCR product was visualized after resolving on agarose gel electrophoresis.
Figure 16E:
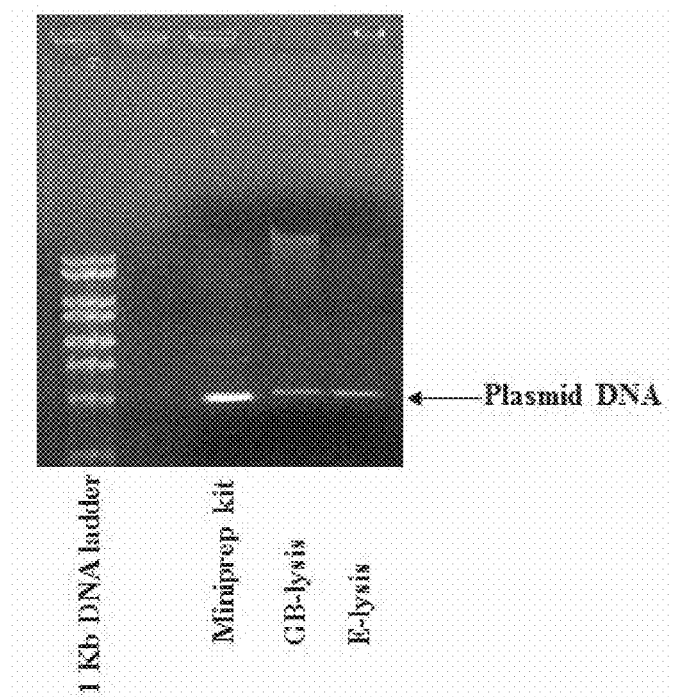
FIG. 16(E) shows the plasmid DNA purified from the supernatant of cell lysate.
Figure 16F:
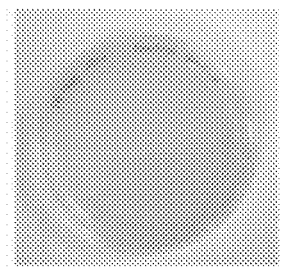
FIGS. 16(F)-(I) demonstrate the integrity of plasmid DNA in the supernatant of cell lysate by culturing *E. coli* on a selection medium after transformation with purified pUC19 plasmid, showing plated results 16(F) without plasmid, 16(G) with purified plasmid control, 16(H) with purified plasmid from glass bead lysis and 16(I) with purified plasmid from E-lysis.
Figure 16G:
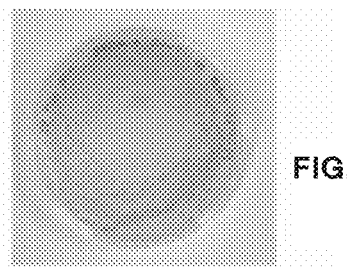
Figure 16H:
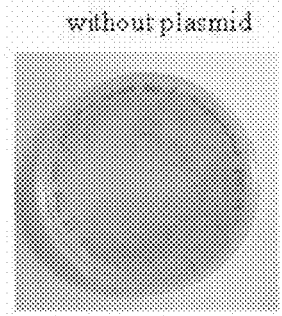
Figure 16I:
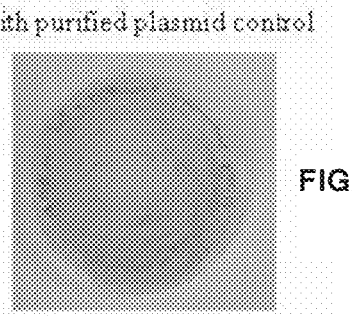

The plasmids purified from 3 different types of cell lysis were resolved by agarose gel electrophoresis and the release of plasmid by glass bead beating or electrical lysis was presented in FIG. 16e. Modification of genomic DNA structure as a result of electrical lysis by the device could be advantageous for plasmid DNA purification without the requirement of hazardous chemical lysis and macromolecular denaturation by sodium hydroxide. For example, after electrical treatment of the lysate, the genomic DNA, having an altered conformational state (as evidenced in FIGS. 15(F), 16(B) and 16(E)), could be separated from the plasmid DNA by a separation method. The separation method could include purification in a spin column and/or separation of the altered genomic DNA from the plasmid DNA using a filter.

To assess the integrity of the plasmid DNA for its possible downstream applications, pUC19 plasmid purified from GB lysis or electrical lysis and the reference plasmid purified by GenElute kit were transformed into DH5-alpha strain of competent *E. coli* cells, using TransformAid Bacteria transformation kit (Fermentas). The transformants were cultured overnight on LB agar plates supplemented with 100 µg/mL Ampicillin, 60 µg/mL X-gal and 0.1 mM isopropylthio-β-D-galactosidase (IPTG) at 37° C.

The growth of transformed *E. coli* cells was observed on LB medium with Ampicillin and X-Gal with similar transformation efficiency for the plasmids obtained from 3 different sample preparation methods, as can be seen in FIGS. 16(f)-(i). This indicates the release of intact cloning quality plasmids by E-lysis.

Example 3: Electrical Lysis of *Streptococcus pneumoniae*

The experiments described in this example are intended to demonstrate the effects of the electrical parameters on the efficiency of the device for lysing *S. pneumoniae* cells. ATCC 6303 strain *S. pneumoniae* cells were grown on Trypticase Soy agar with 5% sheep blood and a single colony of *S. pneumoniae* was cultured in Tryptic Soy Broth overnight at 37° C. For the lysis experiment, the cells were centrifuged at 10000 rpm for 5 min. The cell pellet was washed twice and re-suspended in 0.2 to 0.4 mM phosphate buffer pH 7.4 at a concentration of $1 \times 10^9$ CFU/mL.

Cell lysis efficiency was assessed by total protein assay and quantitative total nucleic acid assay. As a reference cell lysis control, cells were lysed mechanically by beating with an equal volume of glass beads (106 µm, Sigma) for 2 min and the supernatant of glass bead cell lysate was assayed after centrifugation.

Example 3.1 Effects of Pulse Amplitude and Train Duration and Ionic Strength on Electrical Lysis Efficiency The bacteria suspension of $1 \times 10^9$ CFU/mL concentration in 0.2 and 0.4 mM phosphate buffer pH 7.4 was passed through a wide channel in steps of 10 µL/10 s and 20 kHz pulse trains with different durations and amplitudes were applied to the suspension. The duration and amplitudes of any two different parameter sets, $(t_1, V_1)$ and $(t_2, V_2)$, were related by $t_1/t_2=(V_2/V_1)^2$ to ensure nearly equivalent electrical power delivery to the channel for both cases. The experiments were repeated for five different values of amplitude. The current envelopes for two amplitude limits are presented in FIG. 17(A). For both ionic strengths the train durations are longer than corresponding $t_c$.

Figure 17A:
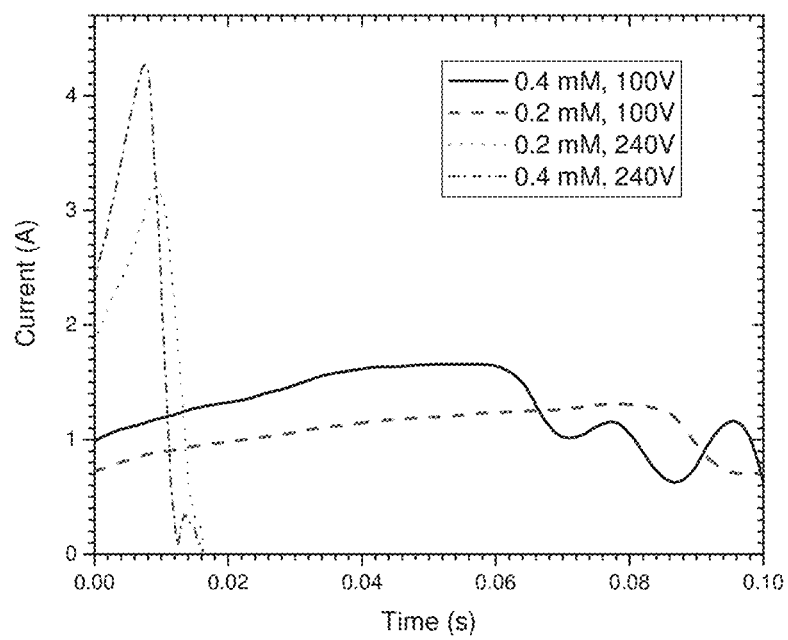
FIG. 17(A) shows the measured current envelopes, corresponding to 4 parameter sets, for the channels in which *Streptococcus pneumoniae* cells were electrically lysed.
Figure 17B:
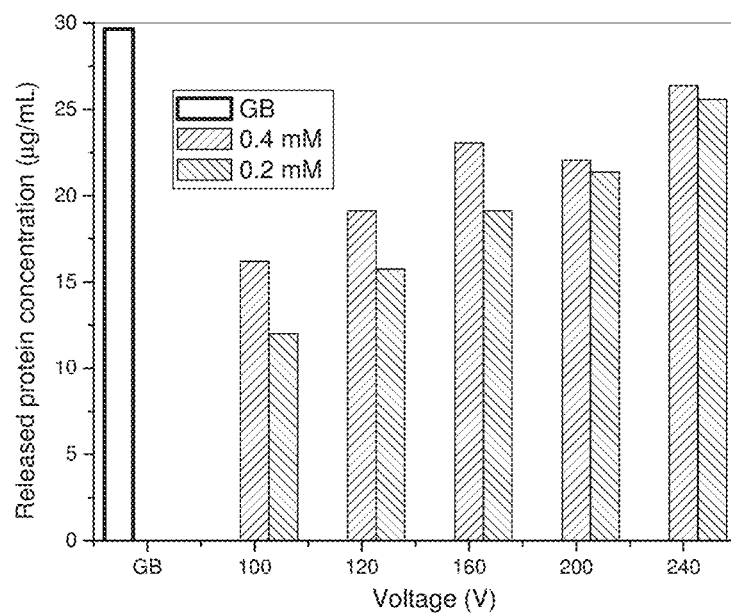
FIG. 17(B) shows the effects of voltage pulse amplitude and ionic strength on the electrical lysis performance of the device as determined by quantifying the release of proteins from *Streptococcus pneumoniae*.
Figure 17C:
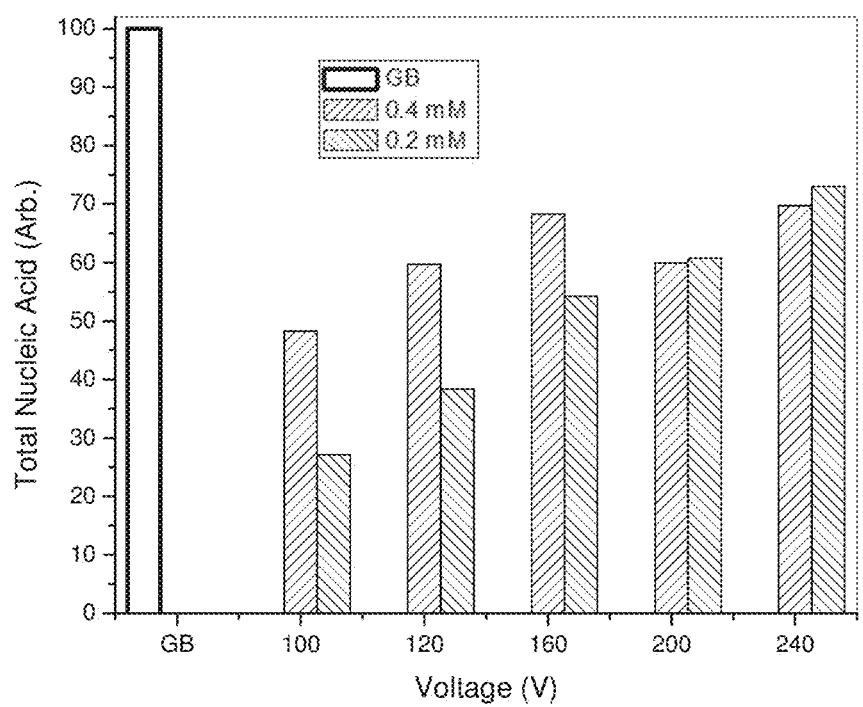
FIG. 17(C) shows the effects of voltage pulse amplitude and ionic strength on the electrical lysis performance of the device as determined by quantifying the release of nucleic acids from *Streptococcus pneumoniae*.

The results of two analytical assays, detections of total protein and total nucleic acid, are presented in FIGS. 17(B) and 17(C). The lysis efficiency is improved by increasing the pulse amplitude and the heating rate.

Example 3.2 the State of Nucleic Acids in the Electrically Prepared Lysate

To assess the spectrum of different types of nucleic acids released by electrical lysis, the cell lysates were centrifuged at 10000 rpm for 5 min and the nucleic acids in the supernatants were resolved by gel electrophoresis on 0.5% agarose gel in 0.5×TBE buffer and 0.5 µg/mL ethidium bromide (EtBr) at 150 volts for 45 min. The release of genomic DNA and total RNA by electrical lysis was observed in FIG. 17(d). In comparison with glass bead lysis, the released genomic DNA by electrical lysis was mainly observed as a slower mobility band with less fluorescence intensity. Similar to the case of the *E. coli*, this observation was attributed to conformational change of the genomic DNA to relaxed state.

Example 3.3 Capability of the Device to Prepare Sample for Polymerase Chain Reaction (*Streptococcus pneumoniae*)

This example demonstrates the effectiveness of the lysate treatment action of the device in terms of reducing the inhibitory factors of PCR, enabling direct PCR processing without the need for additional reagents. Bacteria-specific 16S rRNA gene (rDNA) was amplified by PCR, using Bacteria Identification Kit (BioChain Institute, Inc.). The experiments were performed by lysing *Streptococcus pneumoniae* cells under the parameter set similar to (0.4 mM, 240V), the case whose corresponding current is represented in FIG. 17(a).

Figures 17D, 17E:
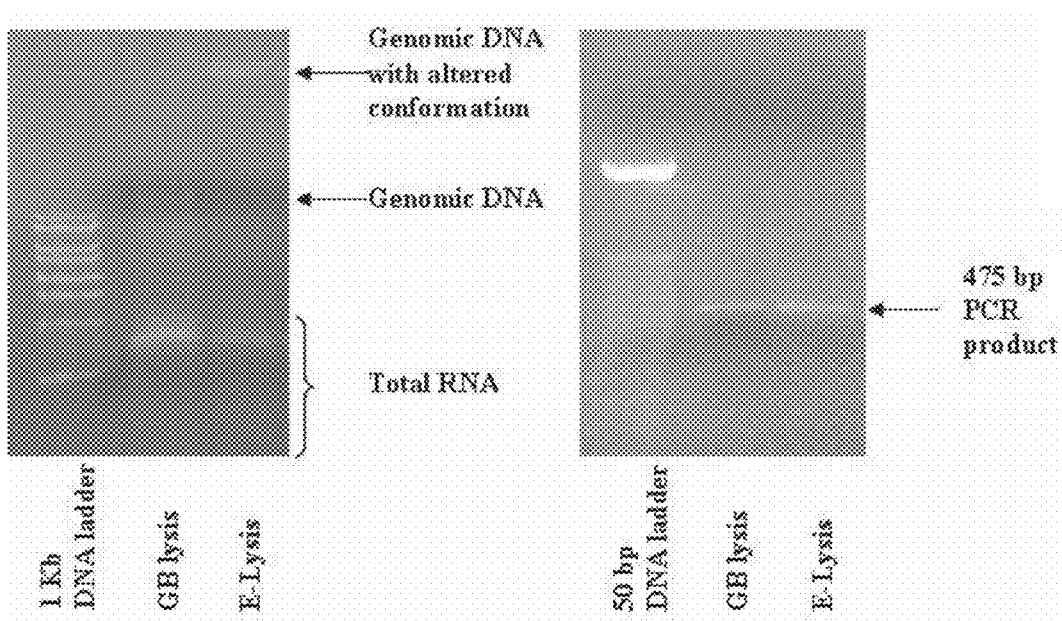
FIGS. 17(D) and 17(E) show spectra of nucleic acids (17D) and PCR amplification of the bacterial 16S rDNA gene fragment derived from *Streptococcus pneumoniae*, visualized after resolving on agarose gel electrophoresis.

Although total cell lysate can be used as an assay-ready sample, to demonstrate the efficient release of genomic DNA out of the cells, the supernatant of the cell lysate was used for PCR. The cell lysate was centrifuged at 7000 rpm for 5 min and the supernatant containing released genomic DNA was collected. The cell lysate supernatant of 1 µL volume was used for PCR amplification. The resulting PCR product of 475 base pair fragment of 16S rDNA was resolved by gel electrophoresis on 1.2% agarose gel in 0.5×TBE buffer and 0.5 µg/mL ethidium bromide at 150 volts for 30 min. A fragment of 16S rDNA was efficiently amplified from the supernatant of electrical lysate as indicated in FIG. 17(e).

Figure 18A:
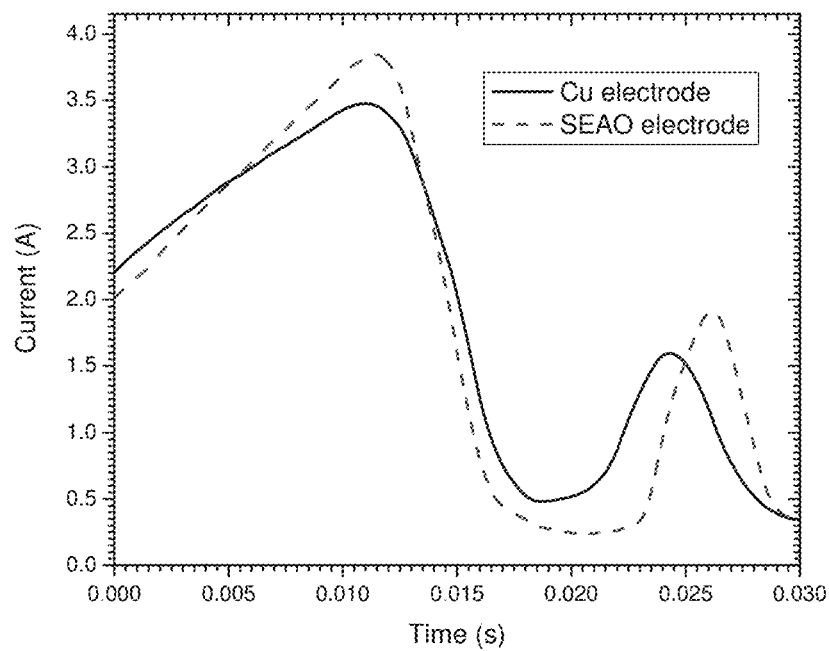
FIG. 18(A) shows the measured current envelopes, corresponding to different devices used for lysing *Streptococcus pneumoniae* cells.

Example 3.4 Dependence of the Device Lysis Performance on Electrode Material This study shows the advantages of using SEOA as electrode material in terms of preserving macromolecule integrity during electrical lysis. *S. pneumoniae* cells, suspended in 0.4 mM phosphate buffer pH 7.4, were lysed in geometrically similar wide channels; one channel having SEOA2 electrodes and the other having copper electrodes. The pulse amplitude and frequency were 200 V and 20 kHz, respectively. The current envelope corresponding to these cases are presented in FIG. 18(A).

Figures 18B, 18C:
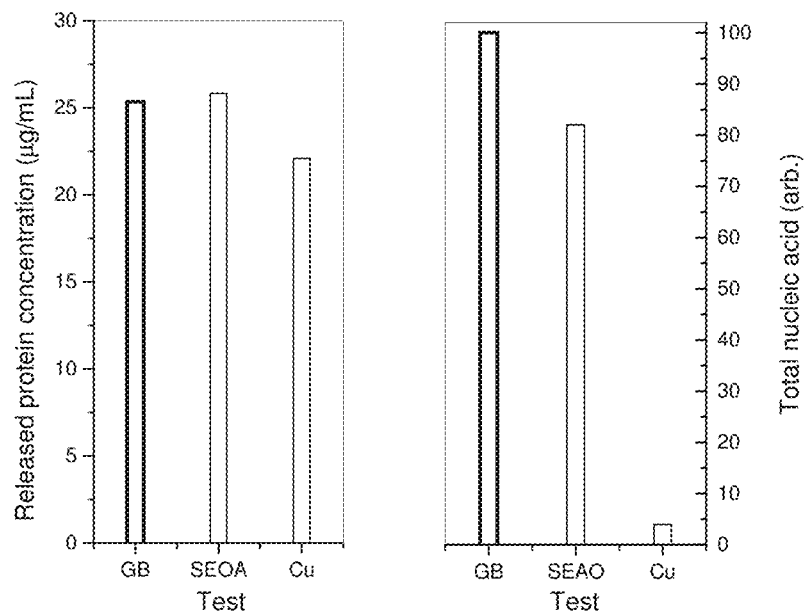
FIGS. 18(B) and 18(C) show the effects of electrode material on the lysis performance of the cells as determined by quantifying the release of 18(B) proteins and 18(C) nucleic acids from *Streptococcus pneumoniae*.
Figure 18D:
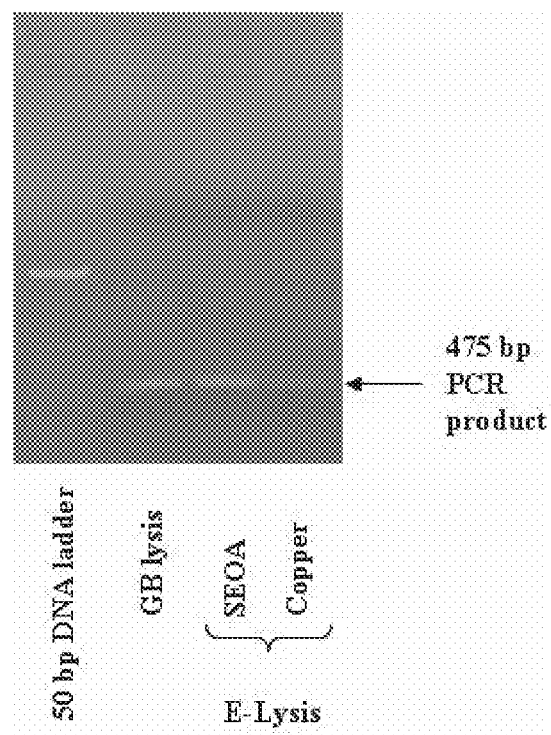
FIG. 18(D) shows PCR amplification of the bacterial 16S rDNA gene fragment of *Streptococcus pneumoniae* as visualized after resolving on agarose gel electrophoresis.

The performances of the devices were assessed by running Bradford protein assays and total nucleic acid assays, following the protocols of example 3.1. The results are presented in FIGS. 18(b) and 18(c). While the two channels are similar in terms of releasing proteins, the total nucleic acid signal is very low for the case of copper electrode, indicating possible degradation of the nucleic acid molecules during electrical lysis. To further verify this observation PCR was performed on samples lysed by the two devices and the result was presented in FIG. 18*d*.

Example 4: Electrical Lysis of *Saccharomyces cerevisiae*

The experiments described in this example are intended to demonstrate the effects of the electrical parameters on the efficiency of the device for lysing *S. cerevisiae* fungal cells. The cells were grown on Trypticase Soy agar with 5% sheep blood and a single colony of *S. cerevisiae* was cultured in Tryptic Soy Broth overnight at 37° C. For the lysis experiment, the cells were centrifuged at 10000 rpm for 5 min. The cell pellet was washed twice and re-suspended in 0.4 mM phosphate buffer pH 7.4 at a concentration of $2.5 \times 10^7$ CFU/mL.

Cell lysis efficiency was assessed by total protein assay and quantitative total nucleic acid assay. As a reference cell lysis control, cells were lysed mechanically by beating with an equal volume of glass beads (710-1180 µm, G1152 Sigma) for 2 min and the supernatant of GB was assayed after centrifugation.

The cell suspension was passed through a wide channel in steps of 10 µL/10 s and 20 kHz pulse trains with a duration of 29 ms and pulse amplitude of 190 V. The experiments were repeated under two conditions, open and restricted ports. In the later case, a restriction in the movement of the liquid at the inlet and outlet ports enabled superheating. The current envelopes for the two cases are presented in FIG. 19(A). The estimated average temperature of the superheated liquid in the restricted channel was approximately 160° C.

Figures 19B, 19C:
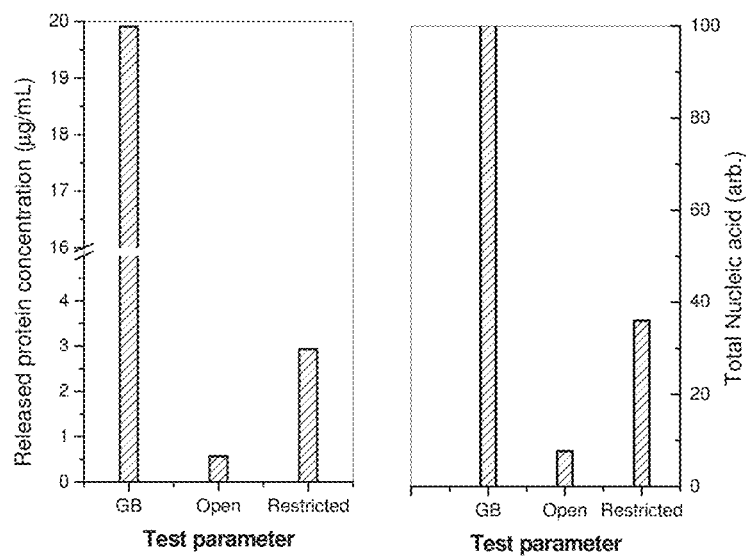
FIGS. 19(B) and 19(C) demonstrate lysis efficiency of the electrical lysis method, as compared to that of glass bead lysis, according to the measured 19(B) total protein concentration and 19(C) total nucleic acid released from lysed *S. cerevisiae* cells.

The results of two analytical assays, measurements of total released protein and nucleic acid, are presented in FIGS. 19(B) AND 19(C). The lysis efficiency is substantially improved by superheating.

Figure 20A:
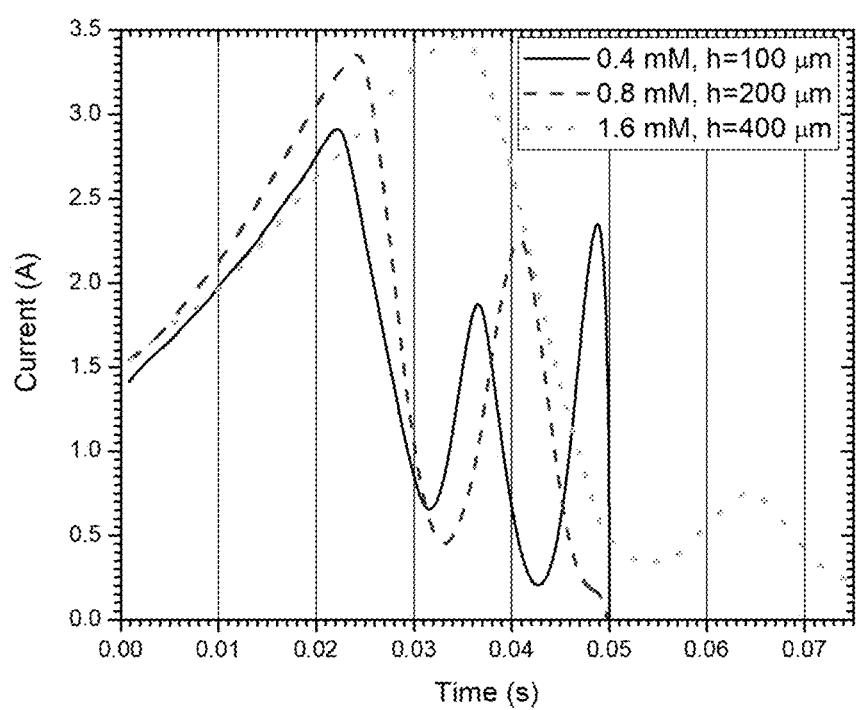
FIG. 20(A) shows the measured current envelopes, corresponding to different devices used for lysing *E. coli* cells.

Example 5: Capability of the Device to Prepare Assay-Ready Sample for Reverse Transcription (RT)-PCR of rRNA This example demonstrates the assay readiness of the lysate prepared in the device by subjecting the lysate to enzymatic transcription of a section of rRNA followed by PCR amplification of the resulting cDNA. The tests were performed using three wide channels with differing heights; h=100 µm, h=200 µm, and h=400 µm. The ionic strengths of the cell suspensions lysed in these channels were, respectively, 0.4, 0.8 and 1.6 mM, thus ensuring nearly similar initial ionic currents in the channels for a given applied voltage. Moreover, the liquid was injected in differing steps of 5 µL/10 s (for h=100 µm), 10 µL/10 s (for h=200 µm) and 20 µL/10 s (for h=400 µm) into the three channels such that each cell experienced the 10 kHz and 160 V pulse trains twice. The current envelopes for the three cases are presented in FIG. 20(A).

Bacteria-specific 16S rRNA was detected by reverse transcription polymerase chain reaction (RT-PCR), using SuperScript III One-Step RT-PCR system with Platinum Taq DNA polymerase (Invitrogen, Life Technologies). NEB5-alpha *E. coli* cells of $10^4$ CFU/mL in 0.4 to 1.6 mM phosphate buffer pH 7.4 were lysed by E-lysis. As reference cell lysis methods, cells were lysed mechanically by beating with an equal volume of glass beads or thermally by incubation at 95° C. for 5 min. As a negative RT-PCR control, RT-PCR grade water (Invitrogen, Life Technologies) was used instead of the sample. RT-PCR reaction of 25 µL volume was prepared by mixing 1 µL of sample (either the lysate, denoted by T, or the supernatant of the lysate, denoted by S), 12.5 µl of 2× Reaction mix, 0.5 µl of forward primer (16S rRNA forward, 10 µM, Integrated DNA Technology), 0.5 µl of reverse primer (BU1.3R, 10 µM), 0.5 µl of SuperScript III RT/Platinum Taq Mix, 10 µl of RT-PCR grade water. 16 s rRNA forward primer (5'-AGAGTTT-GATCCTGGCTAG-3') (SEQ. ID. 6) is a commercially available primer, and BU1.3R (5'-TAAGGTTCTTCGCGTTGCTT-3') (SEQ. ID. 7) is a bacteria specific universal primer designed by sequence alignment software (Bioedit, Ibis Biosciences, USA) and primer design software (Primer3, National Institutes of Health). The 16S rRNA gene fragment of 992 base pairs was amplified by one-step RT-PCR by reverse transcription at 55° C. for 10 min, inactivation of reverse transcriptase at 94° C. for 2 min, followed by 30 cycles of cDNA amplification at 94° C. for 15 sec, 55° C. for 30 sec, and 68° C. for 45 sec, and final extension at 68° C. for 5 min.

Figure 20B:
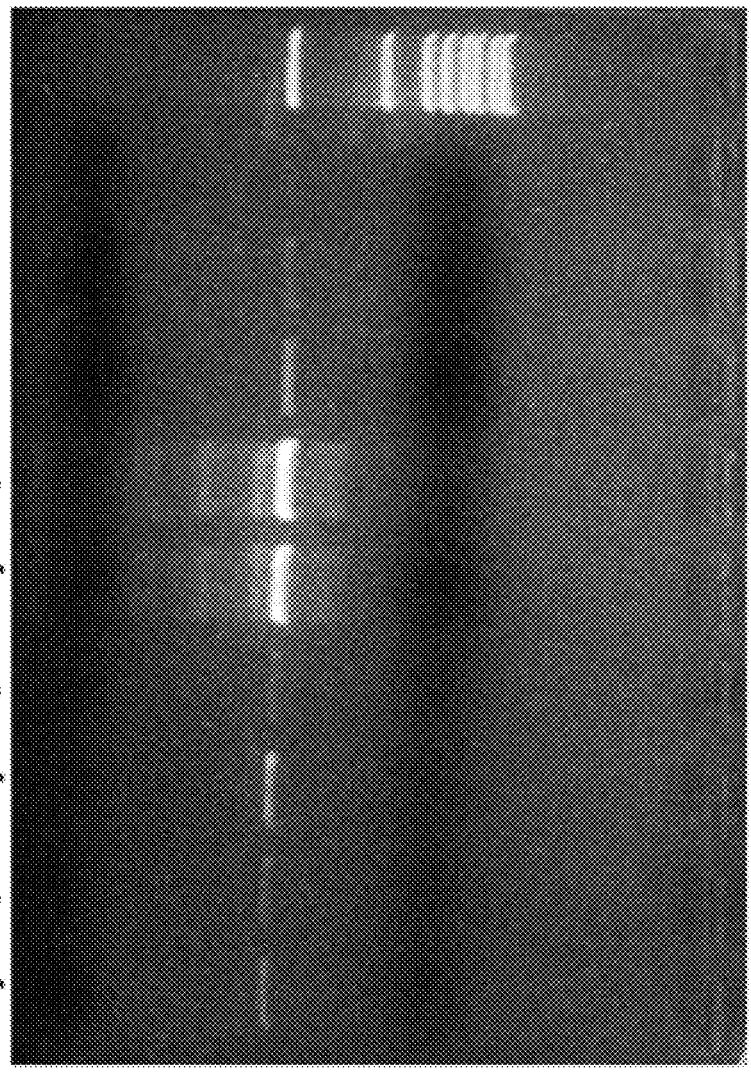
FIG. 20(B) shows reverse transcription (RT)-PCR amplification of a section of *E. coli* rRNA visualized after resolving on agarose gel electrophoresis (S=supernatant,T=total lysate).

The resulting PCR product was resolved by gel electrophoresis on 1% agarose gel in 0.5×TBE buffer and 0.5 µg/mL ethidium bromide at 150 volts for 30 min. RT-PCR product of rRNA derived from E-lysis of NEB5-alpha *E. coli* cells was observed in FIG. 20(B) (where "S" denotes PCR performed on the supernatant of the lysate, and "T" denotes PCR performed on the total lysate). The result indicated that while taller channels (h=200 and 400 µm) perform similar to glass bead beating, the signal corresponding to h=100 µm channel is much higher, making the device more suitable for sensitive detection of bacterial cells.

Example 6: Control of Electrical Treatment and Electrical Lysis Via Electrical Feedback Example 6.1: Fabrication of Device with Open and Closed Channels In this example, two devices were constructed for which the inlet and outlet channels were accordingly dimensioned so as to yield channels which were fluidically unrestricted (open) or restricted. With reference to FIG. 5(D), devices were constructed with polycarbonate top and bottom plates (230 and 231), surface enhanced oxidized aluminum electrodes on the channel top and bottom surfaces (225 and 226) and a polyimide spacer in which the electrical channel (220) and inlet and outlet channels (221 and 222) were formed. The electrical channels for both open and restricted conditions were 15 mm long, 6.4 mm wide and 0.2 mm in height. The inlet and outlet channels were 0.1 mm in height, 10 mm in length and 1.5 mm and 0.5 mm in width for the open and restricted channels respectively.

The channels were exposed to atmospheric pressure at the entrance and exit ports and subjected to an applied voltage in the form of a square bipolar pulse train with 200 pulses, a constant amplitude of 195 V and a frequency of 10 kHz. The current flowing across the channel is plotted in FIG. 21 for 0.8 mM phosphate buffer solution.

Figure 21:
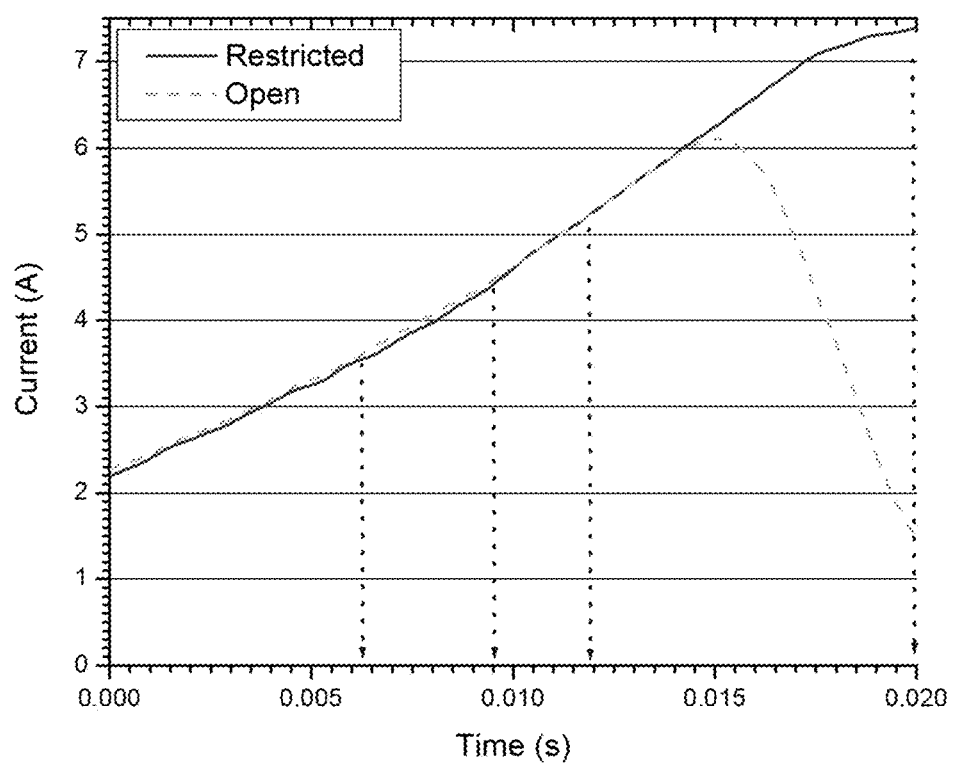
FIG. 21 shows the measured current through an aqueous media subjected to electrical pulse trains inside electrical channels with open and restricted inlet and outlet ports.

For the open channel, the characteristic increase of the electrical current to a maximum value followed by a rapid decrease due to the onset of a liquid to gas phase transition is displayed in FIG. 21. As described in detail in above, it is believed that the maximum current represents a minimum electrical impedance of the fluid and is indicative of the temperature of the fluid. At this point the fluid is in a saturated liquid state in some regions of the channel combined with some regions of initial vapor formation and zones of fluid at cooler temperatures near the boundaries. The subsequent decrease of current in the open channel appears to result from the expansion of the vapor region and the consequent momentary expulsion of fluid from the channel through the inlet and outlet ports into tubes mounted at the ports. The displaced liquid and vapour rapidly cool, and condensation of the vapour occurs returning the liquid to the channel momentarily following expulsion.

The electrical channel with restricted inlet and outlet achieves a higher electrical current, and hence a lower impedance, indicating a higher liquid temperature as compared to the case of an open channel with similar channel dimensions. This is due to the buildup of pressure in the channel afforded by the higher fluidic resistance of the inlet and outlet channels which suppresses phase change and allows temperatures in excess of those in the open channel to be achieved.

In this example for the restricted channel electrical pulses were halted at 0.02 seconds which prevented the occurrence of extended phase change and vapour formation which would have led to a decrease in the electrical current as occurred for the open channel example. The ratio of the initial impedance to the minimum impedance in FIG. 21 are 3.16 and 2.55 for the restricted and open channels respectively which illustrates the higher temperature achieved in the restricted channel.

The finite differences analysis of transient heat transfer in the fluid filled electrical channel was used to estimate channel temperatures both during and following the electrical pulse train. Fourier's law of heat conduction was solved numerically in conjunction with conservation of energy for a channel spatially discretized across the thickness and the width of the layered channel assembly and for which temperature is assumed to be uniform over the length of the channel.

Figure 22:
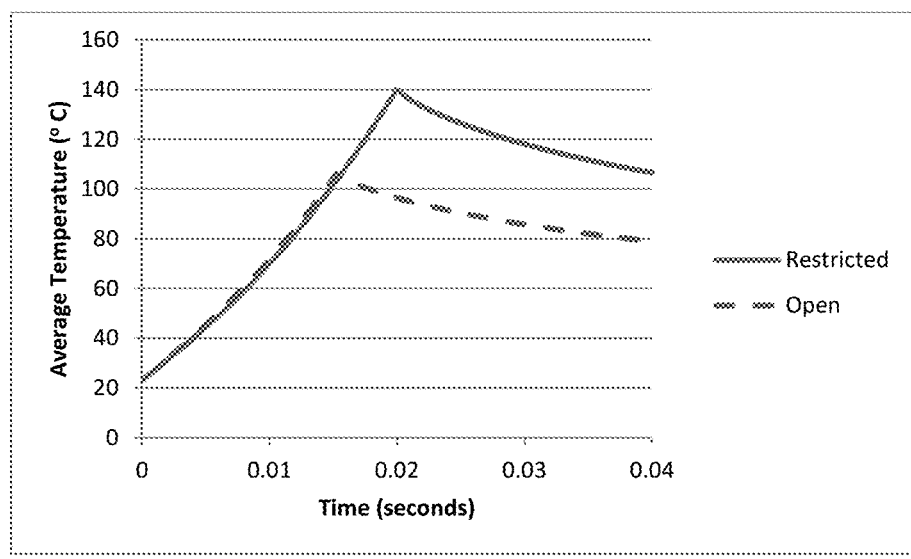
FIG. 22 shows the calculated time dependent average temperatures of the restricted and open channels with the current responses presented in FIG. 21.

The finite differences analysis described earlier was used to analyse Joule heating of the channel fluid using measured voltage and current and assuming a linear thermal dependence of the conductance of the fluid with an assumed value of 2.5% per degree Celcius. The calculated average channel temperatures are presented in FIG. 22 for the open and restricted channel example described above over a period of 0.04 seconds for which the voltage pulse train was halted at 0.02 seconds. The calculations indicate that a central region of the channel achieves superheated temperatures of approximately 120° C. and 160° C. for the open and restricted channels respectively. Peak average channel temperatures reached are 106° C. and 140° C. respectively. In another electrical channel embodiment, described further in an example below, the inlet and outlet channels are equipped with valves (223 and 224 in FIG. 5 which allow the electrical channel to be effectively closed during the application of the voltage pulse train. The buildup of pressure in the channel can in this case be greater than the case of the restricted channel of the above example, thus higher fluid temperatures can be achieved before reaching the boiling threshold. Pressure buildup in the channel cannot for practical purposes be allowed to increase arbitrarily since, depending on the structure and materials of which the channel is constructed, the device will possess a failure pressure at which point the channel will leak or fail catastrophically.

Active control of the voltage pulse train may be employed to limit the maximum pressure experienced by the channel. Active control may also be used to avoid vapour formation with its concomitant expulsion of fluid from the channel which may be undesirable in some applications such as, for example, integration into a fluidic cartridge.

Example 6.2: Temperature Dependence of Electrical Lysis Efficiency in Electrical Channels with Restricted Inlet and Outlet Channels This example demonstrates the dependence of electrical lysis efficiency on the temperature at the electrical channel. *C. albicans* cells were grown on tryptic soy agar with 5% sheep blood. A single colony of *C. albicans* was cultured in tryptic soy broth overnight at 37° C. The cells were centrifuged at 7000 rpm for 5 min. The cell pellet was washed twice and re-suspended in 0.8 mM phosphate buffer pH 7.4, which was pre-filtered through a 0.2 μm filter. Four aliquots of *C. albicans* cells in phosphate buffer were subjected to voltage pulse trains of amplitude 195 V and frequency 10 kHz which were halted at predetermined voltage train durations. The electrical channel was as described above with restricted inlet and outlet channels. The current response of the channel is similar to that presented in FIG. 21 and the selected train durations are indicated by arrows. The measured electrical response and the estimated channel temperatures are presented in FIG. 23 for the designated conditions.

Two hundred fungal cells were added into 1000 μL of filter-sterilized 0.8 mM phosphate buffer. For each condition 70 μL of the sample was electrically lysed in steps of 10 μL/10 s. As a reference method comparison control, 100 μL aliquot of the same cell suspension was mechanically lysed using glass beads. An equal volume of glass beads (710-1180 μm, Sigma) was added to the cell suspension and the mixture was vortexed at maximum speed for 5 min. Then the cell lysate supernatant was collected after centrifugation. This lysis method will be known as GB lysis.

Reverse transcription-PCR assay was performed on 5 μL of each lysate, which is equivalent to detection at a single cell level using KAPA SYBR FAST One-Step qRT-PCR Universal kit (KAPA Biosystems). As a negative RT-PCR control, pre-filtered 0.8 mM phosphate buffer pH 7.4, used for cell suspension was added instead of the sample. The reverse transcription PCR protocol used UFF4 forward primer; 5'-AATTTCTGCCCTATCAACTTTCG-3' (SEQ. ID 1) and UFR4 reverse primer, 5'-CCCAAGGTTCAAC-TACGAGCTT-3' (SEQ. ID 2). The fungal specific primers are designed by sequence alignment software (Bioedit, Ibis Biosciences, USA) and primer design software (Primer3, National Institutes of Health), and synthesized by Invitrogen, Life Technologies. Reverse transcription PCR reaction of 20 μL volume was prepared by mixing 5 μL of 2×KAPA SYBR FAST qPCR 2× mastermix, 0.4 μL 50×KAPA RT mix, 0.5 μl of forward primer (10 μM), 0.5 μl of reverse primer (10 μM) and 3.6 μl of nuclease-free water. The 18S rRNA gene fragment of 343 base pairs at a hypervariable region of all fungal species (nucleotide 296 to 639 using *Candida albicans* AB013586 as a reference) was amplified. One-step real time reverse transcription PCR was performed by reverse transcription at 55° C. for 5 min, inactivation of reverse transcription at 95° C. for 2 min, followed by 30 cycles of cDNA amplification at 95° C. for 3 sec, 59° C. for 3 sec, and 72° C. for 3 sec in Eco real time PCR system (Illumina).

Figures 24A, 24B:
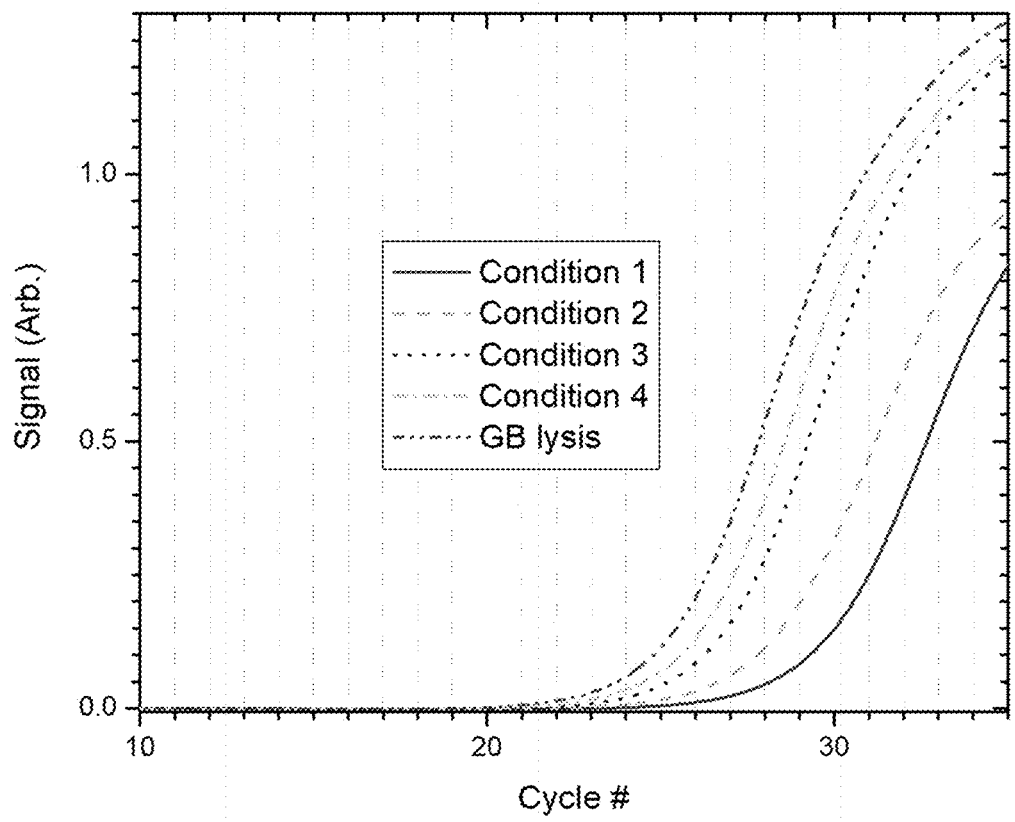
FIG. 24(A) shows the fluorescence signal measured during real time RT-PCR assay for different conditions in Example 6.2.
FIG. 24(B) shows the CT values of the real time RT-PCR assay described in FIG. 24a for the detection of fungal cells lysed under different conditions.
Figure 25A:
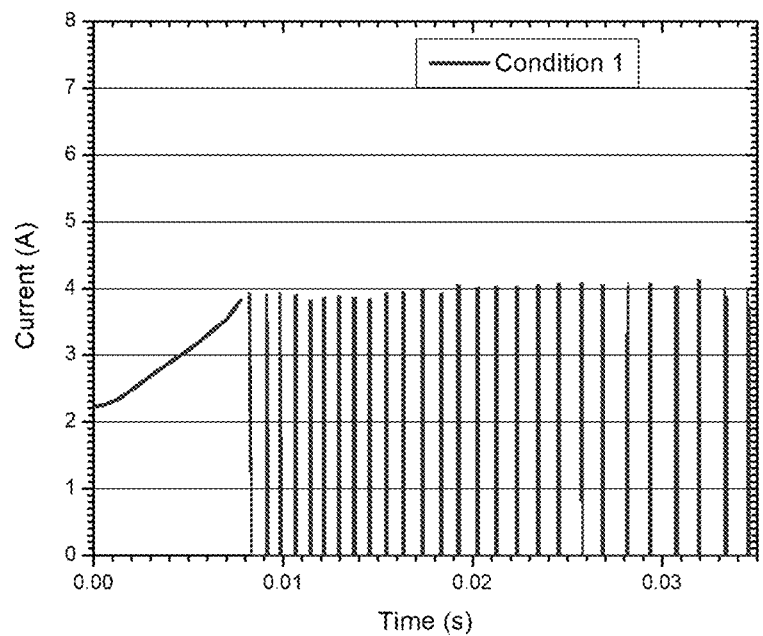
FIG. 25(A) shows the measured current through a cell suspension subjected to electrical pulse trains inside the restricted electrical channel corresponding to the condition 1 of Example 6.3.
Figure 25B:
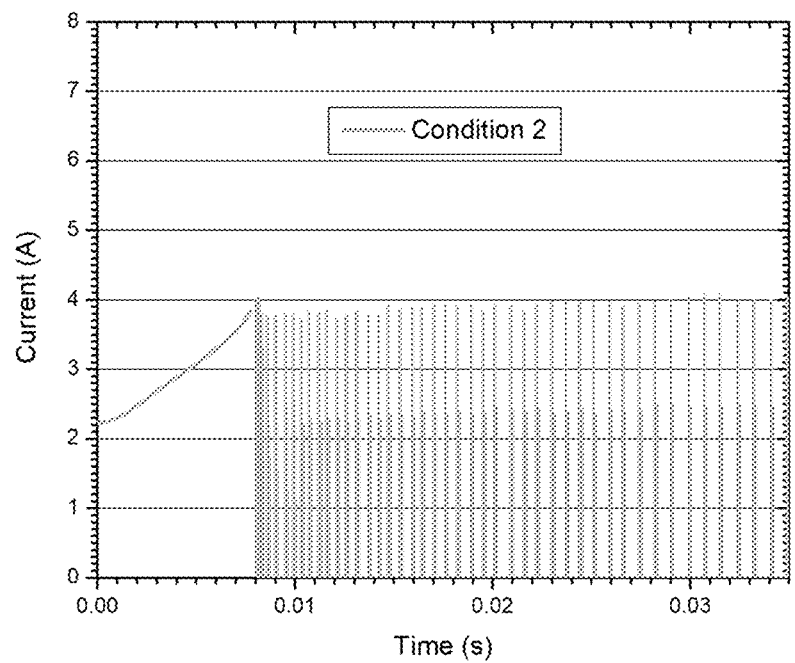
FIG. 25(B) shows the measured current through a cell suspension subjected to electrical pulse trains inside the restricted electrical channel corresponding to the condition 2 of Example 6.3.
Figure 25C:
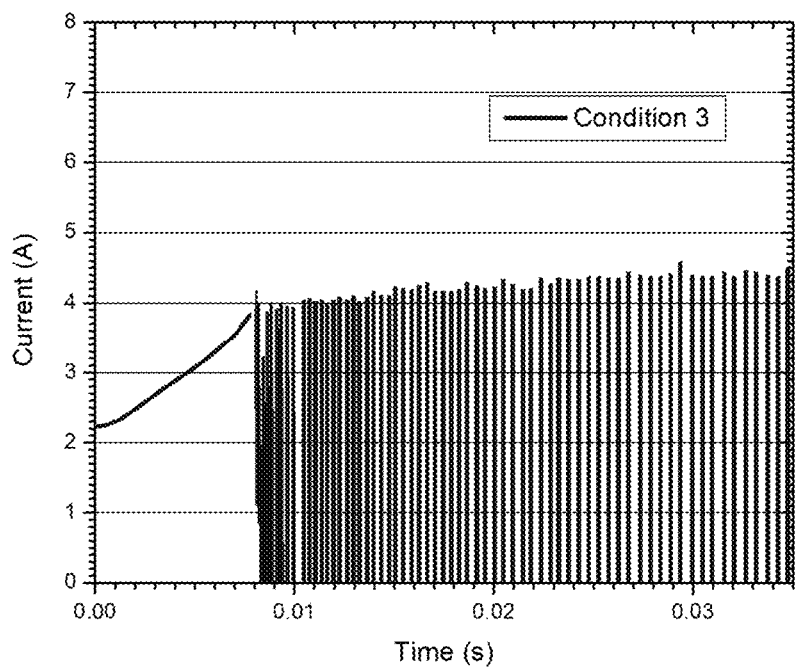
FIG. 25(C) shows the measured current through a cell suspension subjected to electrical pulse trains inside the restricted electrical channel corresponding to the condition 3 of Example 6.3.
Figure 25D:
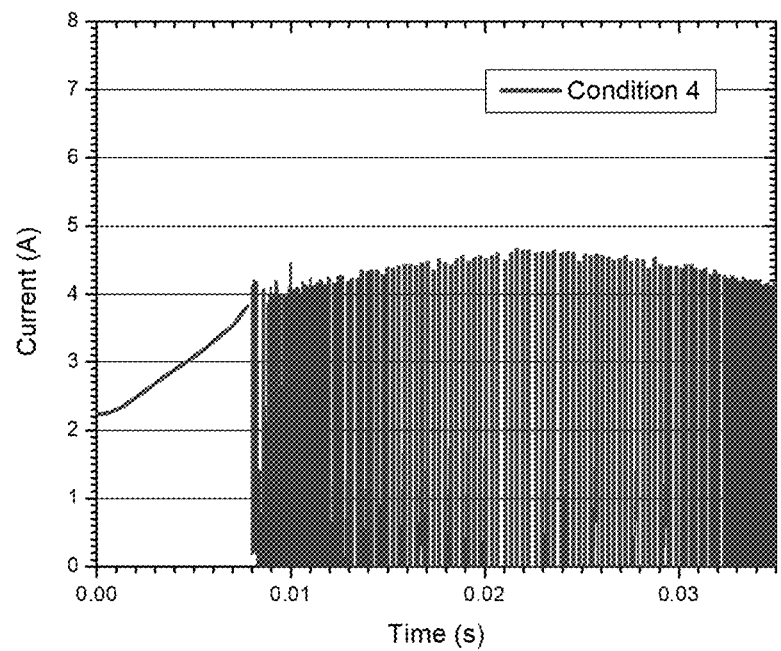
FIG. 25(D) shows the measured current through a cell suspension subjected to electrical pulse trains inside the restricted electrical channel corresponding to the condition 4 of Example 6.3.
Figure 25E:
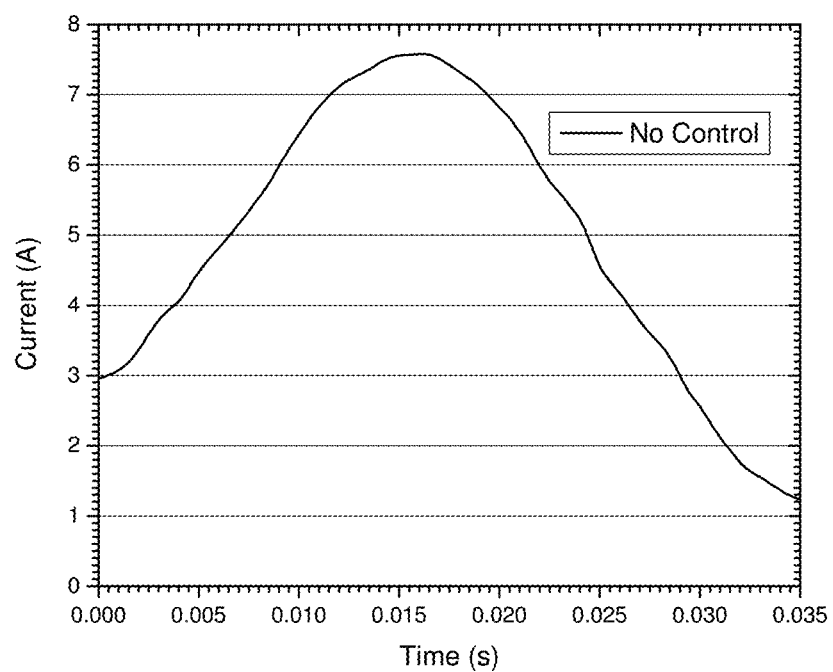
FIG. 25(E) shows the measured current through a cell suspension subjected to electrical pulse trains inside the restricted electrical channel corresponding to the case when the pulse density was kept at the maximum value over the whole duration of the pulse train.

The RT-PCR fluorescence signals versus cycle number plots are presented in FIG. 24(A). The standard deviation, σ, of the signal over the first 10 cycles, where the signal is predominately background noise, is calculated for each curve and a threshold signal level is decided to be 6σ. The cycle number where the recorded signal exceeds the threshold level is defined as $C_T$. The determined $C_T$ values are presented in FIG. 24(B). As it is observed the lysis efficiency, inferred from the $C_T$ values, increases with peak liquid temperature, approaching the GB lysis efficiency.

It is expected that higher lysis and treatment efficiency can be obtained with higher peak temperatures which can only be achieved in the present channel by further restriction or closure of the inlet and outlet ports together with feedback control which is described in Example 6.4 below. Lysis and treatment efficiency may also be increased by increasing the residence time at elevated temperatures using feedback control of the voltage pulses which is described in Example 6.3 below. This approach also offers a way to overcome a potential limitation on the power available from the constant voltage power supply by increasing efficiency at lower power levels.

Example 6.3: Dependence of Electrical Lysis Efficiency in an Electrical Channel on the Pulse Density Over an Extended Residence Time This example demonstrates the method of increasing the electrical lysis efficiency by extending the residence time. The method may improve electrical lysis and treatment effectiveness and can also be advantageous when the power supply is not able to deliver high currents and the system design constraints require operation at lower channel temperatures. The method is based on rapidly increasing the channel temperature to a desired value corresponding to a preselected impedance setpoint. Thereafter the pulse density is decreased such that the average channel temperature is maintained within desired bounds.

The measured current responses corresponding to five conditions are presented in FIGS. 25(A)-25E). In all cases voltage pulses with a constant amplitude of 195V and frequency 10 kHz were applied. In the case of the first four conditions the channel temperature is brought to the estimated maximum value of 67° C. in approximately 8 ms by the voltage pulse train and feedback control was activated when the current reached 3.9 Amps. Thereafter impedance feedback control was activated introducing delays between pulses in response to the impedance error signal. Controller parameters were varied to create the conditions 1, 2, 3 and 4 whose resulting current behavior is shown in FIGS. 25(A) to 25(D), respectively.

It can be seen from these plots that the pulse density during the control period differed somewhat between conditions as did the ability of the controller to accurately hold impedance at a constant value. In all these cases, significant vapour formation in the channel was prevented.

For the uncontrolled case, whose electrical response is shown in FIG. 25 (E), the maximum pulse density is maintained at its maximum value for the whole train duration of 35 ms. After approximately 16 ms following the onset of the pulse train the vapour formation threshold (at temperatures similar to the restricted channel of FIG. 22) is reached and the liquid experiences rapid expulsion due to the formation of a vapour phase causing a rapid decrease in the current.

*C. albicans* cell suspension containing two hundred fungal cells in 1000 µL of filter-sterilized 0.8 mM phosphate buffer was prepared following the steps described in example 1. Reverse transcription-PCR assay was performed on 5 µL of each lysate, which is equivalent to detection at a single cell level, using KAPA SYBR FAST One-Step qRT-PCR Universal kit (KAPA Biosystems). As a negative reverse transcription-PCR control, pre-filtered 0.8 mM phosphate buffer pH 7.4, used for cell suspension was added instead of the sample. The reverse transcription PCR protocol used UFF4 forward primer; 5'-AATTTCTGCCCTAT-CAACTTTCG-3' and UFR4 reverse primer, 5'-CC-CAAGGTTCAACTACGAGCTT-3'. The fungal specific primers are designed by sequence alignment software (Bioedit, Ibis Biosciences, USA) and primer design software (Primer3, National Institutes of Health), and synthesized by Invitrogen, Life Technologies. Reverse transcription PCR reaction of 20 µL volume was prepared by mixing 5 µL of sample, 10 µl of 2×KAPA SYBR FAST qPCR 2× mastermix, 0.4 µL 50×KAPA RT mix, 0.5 µl of forward primer (10 µM), 0.5 µl of reverse primer (10 µM) and 3.6 µl of nuclease-free water. The 18S rRNA gene fragment of 343 base pairs at a hypervariable region of all fungal species (nucleotide 296 to 639 using *Candida albicans* AB013586 as a reference) was amplified. One-step real time reverse transcription PCR was performed by reverse transcription at 55° C. for 5 min, inactivation of reverse transcription at 95° C. for 2 min, followed by 30 cycles of cDNA amplification at 95° C. for 3 sec, 59° C. for 3 sec, and 72° C. for 3 sec in Eco real time PCR system (Illumina).

Figures 26A, 26B:
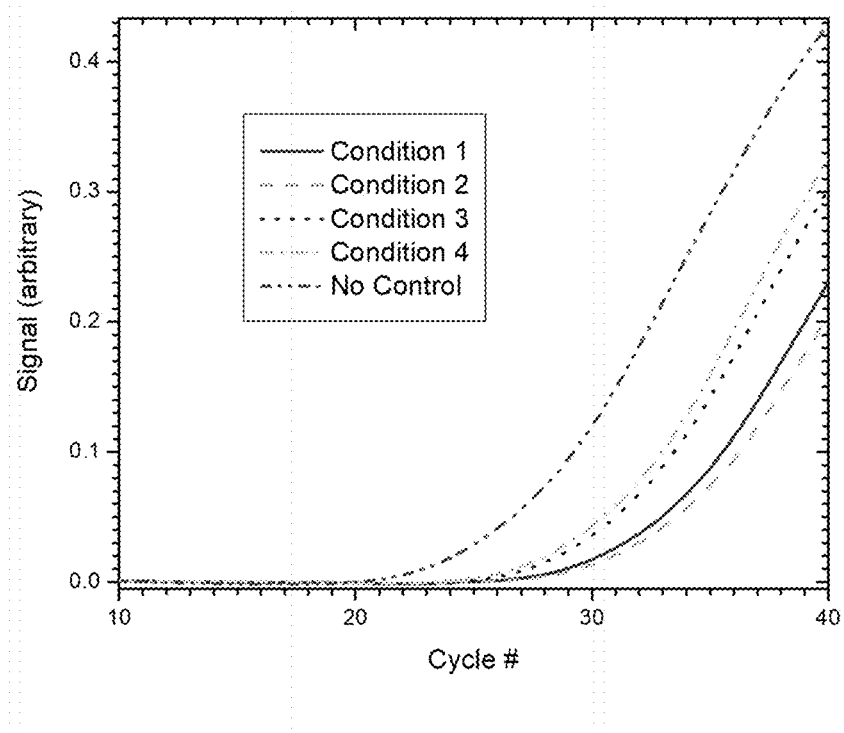
FIG. 26(A) shows the fluorescence signal measured during real time RT-PCR assay for different conditions of Example 6.3.
FIG. 26(B) shows the CT values of the real time RT-PCR assay described in FIG. 26($a$) for the detection of fungal cells lysed under different conditions.

The reverse transcription-PCR fluorescence signals versus cycle number plots are presented in FIG. 26(A). The standard deviation, a, of the signal over the first 10 cycles, where the signal is predominately background noise, is calculated for each curve and a threshold signal level is decided to be 6σ. The cycle number where the recorded signal exceeds the threshold level is defined as $C_T$. The determined $C_T$ values are presented in FIG. 26(B). As it is observed the lysis efficiency, inferred from the $C_T$ values, has increased with increasing the pulse density.

Example 6.4: Efficient Lysis of Fungal Cells in a Closed Electrical Channel Employing Voltage Amplitude Regulation Scheme This example demonstrates the method of increasing the electrical lysis efficiency by superheating the liquid without increasing the current beyond some preselected level. The method may improve electrical lysis and treatment effectiveness and is also advantageous in the case of closed electrical channels whenever the power supply is not able to deliver high currents.

Figure 27A:
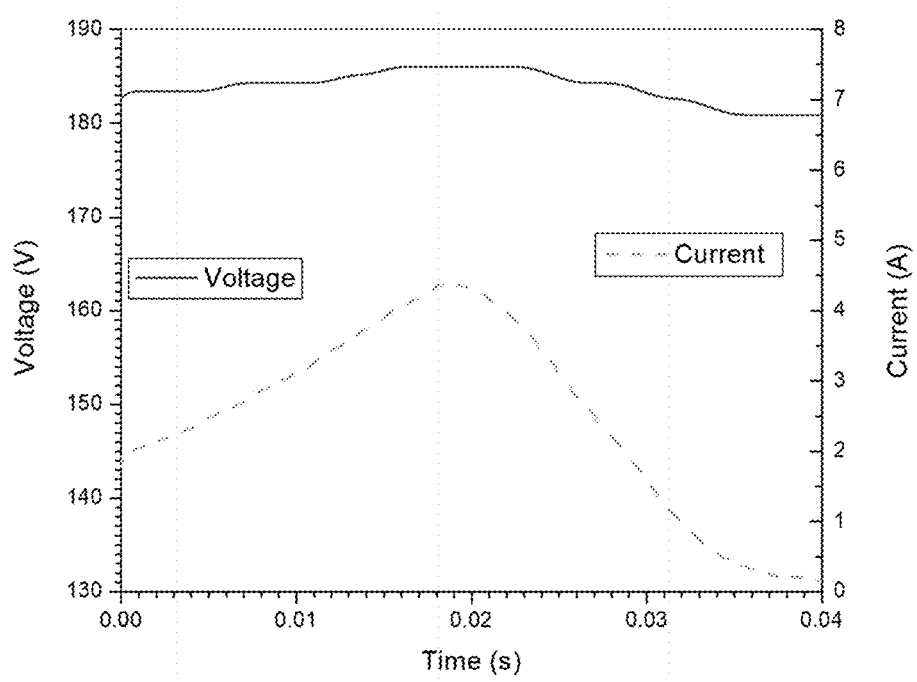
FIG. 27(A) shows the applied voltage and measured current through a cell suspension subjected to electrical pulse trains inside an open electrical channel.
Figure 27B:
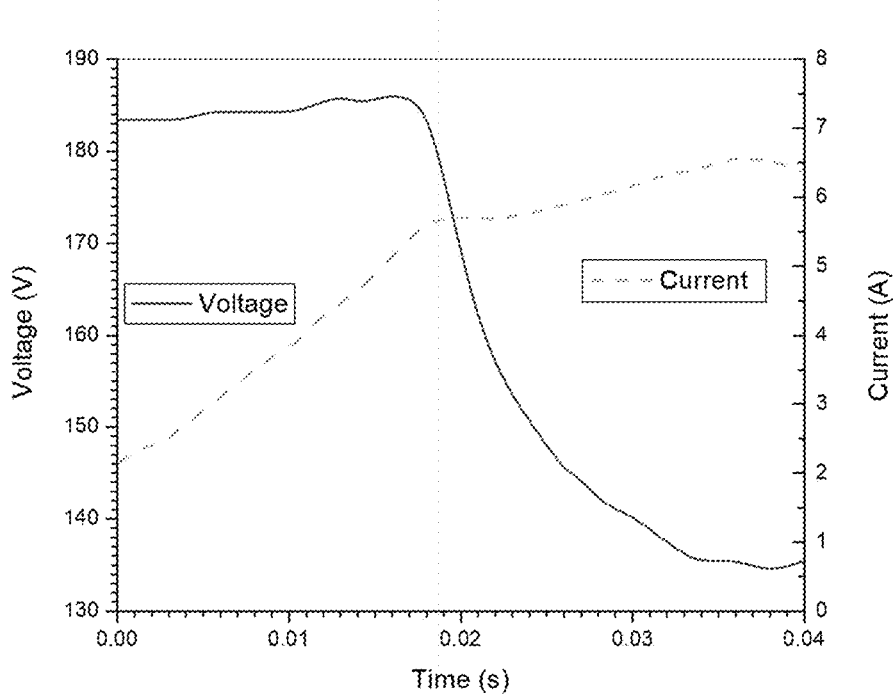
FIG. 27(B) shows the applied voltage and measured current through a cell suspension subjected to electrical pulse trains inside a closed electrical channel.
Figure 27C:
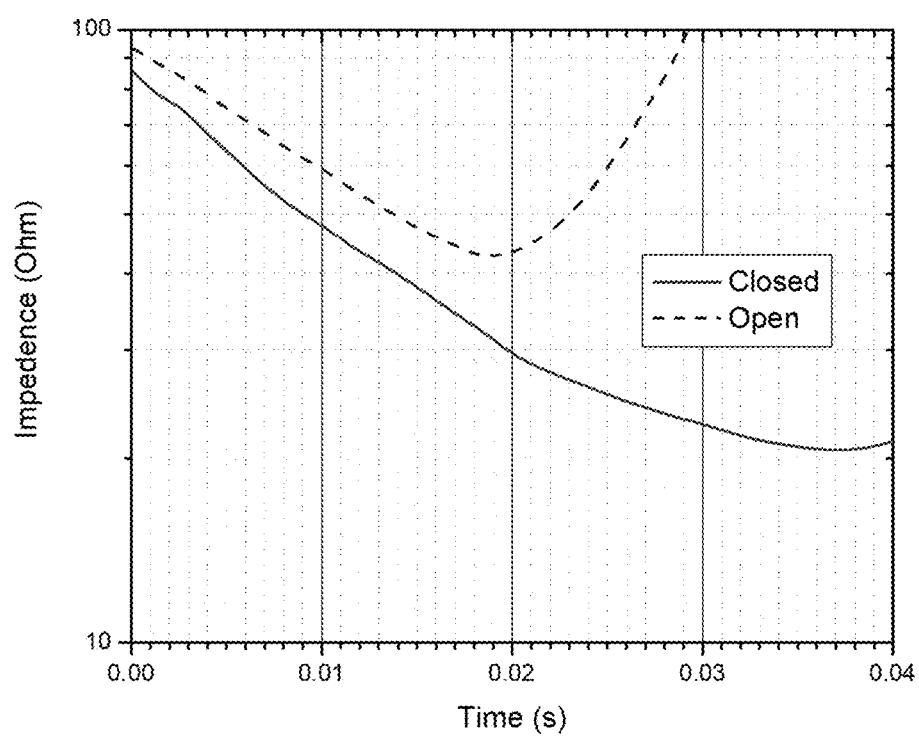
FIG. 27(C) shows the measured impedances of the open and closed channels with electrical responses presented in FIGS. 29$a$ and 29$b$.

In this example, the cells were subjected to mechanical lysis using glass beads as a reference method and electrical lysis under 2 conditions: open and closed channel ports. The cell suspension of $1 \times 10^3$ CFU/mL in 0.6 mM phosphate buffer pH 7.4 was passed through the channel in steps of 10 µL/15 s and the pulse train was applied when the suspension was brought to rest. The electrical response is presented in FIGS. 27 (A) and 27(B) for the two electrical channels. The initial voltage pulse train consisted of approximately 185 V, 10 kHz pulses for which impedance feedback control was introduced when the current reached approximately 5.5 Amps. The voltage amplitude was regulated by the controller to control the channel impedance seen in FIG. 27(C). The impedance minimum value was limited by the controller to prevent channel leakage and channel fluid vaporization.

Fungal rRNA in the cell lysate samples ($10^3$ CFU/mL) was detected by reverse transcription-PCR, targeting a hypervariable region in 18S rRNA of all fungal species. Reverse transcription-PCR reaction of 25 µL volume was prepared by mixing 10 µL of the sample (nominal 10 cells per sample), 12.5 µl of 2×PCR reaction mix (2G Robust HotStart, KAPA Biosystems), 1.2 µL of reverse transcriptase (GoScript, Promega), 0.65 µl of forward primer (UFF3, 10 µM) and 0.65 µl of reverse primer (UFR3, 10 µM). As a negative reverse transcription-PCR control, pre-filtered 0.6 mM phosphate buffer pH 7.4, used for cell suspension was added instead of the sample. UFF3 forward primer (5'-AACGAAAGTTAGGGGATCGAAG-3') (SEQ. ID. 3) and UFR3 reverse primer (5'-CTTTAAGTTTCAGCCTTGCGA-3') (SEQ. ID. 4) are fungal specific primers designed by sequence alignment software (Bioedit, Ibis Biosciences, USA) and primer design software (Primer3, National Institutes of Health), and synthesized by Invitrogen, Life Technologies. The 18S rRNA gene fragment of 167 base pairs at a hypervariable region of all fungi species (nucleotides 940 to 1107 using *Candida albicans* AB013586 as a reference) was amplified by one-step reverse transcription-PCR by reverse transcription at 55° C. for 5 min, inactivation of reverse transcriptase and activation of hot start DNA polymerase at 95° C. for 3 min, followed by 35 cycles of cDNA amplification at 95° C. for 3 sec, 58° C. for 3 sec, and 72° C. for 3 sec, and final extension at 72° C. for 1 min.

The resulting reverse transcription-PCR product of 15 µL was resolved by gel electrophoresis on 1% agarose gel in 0.5×TBE buffer and 0.5 µg/mL ethidium bromide at 150 volts for 30 min. The amplified region of 18S rRNA derived from E-lysis and GB lysis of *C. albicans* cells was observed in FIG. 28 (A). This example demonstrates the performance of electrical lysis with closed channel electrical channel which is superior to electrical lysis with open channel electrical channel and GB lysis.

As a quantitative method of detection, the specific nucleotide sequences within the amplified region were detected using the molecular beacon. reverse transcription-PCR product of 5 µL was mixed with 1 µL of the buffer containing 20 mM Tris-HCl pH 8, 10 mM KCl and 7 mM MgCl$_2$ as well as 1 µM of the molecular beacon 6-FAM-5'-CCGAGCCGTAGTCTTAACCATAAACTATGCGCT-3'-DABCYL (SEQ. ID. 5) (nucleotides 977 to 997 using *Candida albicans* AB013586 as a reference) designed to detect all fungal pathogens. The mixture was heated at 95° C. for 30 sec to denature the amplicon and the molecular beacon, followed by cooling to room temperature, allowing hybridization of the molecular beacon to the target sequence. The resulting mixture of 6 µL was transferred to a microwell and the fluorescence intensity of the samples and negative buffer controls at excitation wavelength of 492 nm and emission wavelength of 517 nm was measured using fluorescence microscopy (LumaScope, Etaluma).

Figures 28A, 28B:
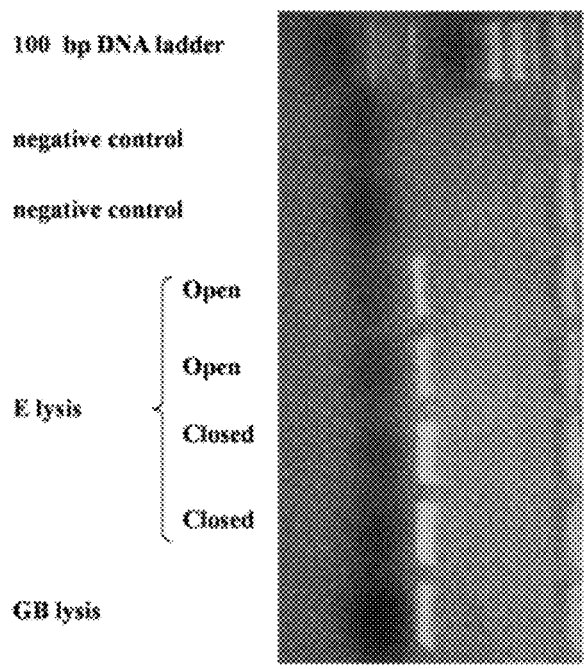
FIG. 28(A) qualitatively demonstrates lysing efficiency of fungal cells in open and closed channel electrical channels by detection of RT-PCR amplified product of *Candida albicans* 18S rRNA fragment, as was visualized after resolving on agarose gel electrophoresis.
FIG. 28(B) quantitatively demonstrates lysing efficiency of fungal cells in open and closed channel electrical channels by detection of RT-PCR amplified product of *Candida albicans* 18S rRNA fragment, as detected by monitoring the hybridization of molecular beacon probes.

The fluorescence signals detected by molecular beacon for the corresponding amplicons resolved by gel electrophoresis in FIG. 28(A) are presented in FIG. 28(B). The quantitative detection also shows the performance of electrical lysis in the electrical channel with closed channels is superior to electrical lysis in the electrical channel with open channels and GB lysis.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

The invention claimed is:

1. A method of electrically processing a cell-containing liquid within a microfluidic device, the method comprising:
flowing the liquid into a microfluidic channel of the microfluidic device;
closing the microfluidic channel, such that the liquid is confined within the closed volume of the microfluidic channel;
while maintaining the microfluidic channel in a closed state, applying bipolar voltage pulses across the microfluidic channel; and
while applying the bipolar voltage pulses:
measuring an electrical current within the microfluidic channel; and
controlling one or more properties of the bipolar voltage pulses, according to feedback based on the electrical current, to achieve conditions within the channel that are sufficient to effect lysis of the at least one cell.

2. The method according to claim 1 wherein the one or more properties of the bipolar voltage pulses are controlled according to a feedback parameter associated with the electrical current.

3. The method according to claim 2 wherein the feedback parameter is one of the electrical current and an impedance of the microfluidic channel.

4. The method according to claim 2 wherein the bipolar voltage pulses are modified after detecting that the feedback parameter associated with the electrical current has reached a pre-selected value.

5. The method according to claim 4 wherein, after detecting that the feedback parameter has reached the pre-selected value, modifying the delivery of the bipolar voltage pulses to maintain the feedback parameter at the pre-selected value.

6. The method according to claim 1 wherein the one or more properties of the bipolar voltage pulses are controlled, according to the feedback from the electrical current, to prevent a phase change from a liquid phase to a vapour phase.

7. The method according to claim 1 wherein the one or more properties of the bipolar voltage pulses are controlled, according to the feedback from the electrical current, to maintain the liquid in a superheated state.

8. The method according to claim 1 wherein the one or more properties of the bipolar voltage pulses that are controlled based on feedback from the electrical current include one or more of voltage pulse train amplitude, pulse density, duty cycle, and pulsewidth.

9. The method according to claim 1 wherein a known temperature dependence of an electrical conductivity of the liquid within the microfluidic device is employed to infer a temperature of the liquid based on the electrical current, and wherein the one or more properties of the bipolar voltage pulses are controlled based on the temperature.

10. The method according to claim 9 wherein the one or more properties of the bipolar voltage pulses are controlled to maintain the liquid at a pre-selected temperature for a pre-selected residence time.

11. The method according to claim 1 wherein the one or more properties of the bipolar voltage pulses are controlled, according to the feedback from the electrical current, such that delivery of the bipolar voltage pulses is maintained after having detected a feature in the electrical current.

12. The method according to claim 11 wherein the feature comprises one or more of a peak, a maximum, and a minimum.

13. The method according to claim 1 wherein the bipolar voltage pulses are applied such that an electric field generated across a thickness of the microfluidic channel is between approximately 2 kV/cm and 30 kV/cm such that the liquid is heated with a heating rate of at least 250 degrees Celsius per second.

* * * * *

SEQUENCE LISTING

<160> NUMBER OF SEQ ID NOS: 7

<210> SEQ ID NO 1
<211> LENGTH: 23
<212> TYPE: DNA
<213> ORGANISM: Artificial
<220> FEATURE:
<223> OTHER INFORMATION: Pan fungal primer

<400> SEQUENCE: 1
aatttctgcc ctatcaactt tcg                                    23

<210> SEQ ID NO 2
<211> LENGTH: 22
<212> TYPE: DNA
<213> ORGANISM: Artificial
<220> FEATURE:
<223> OTHER INFORMATION: Pan fungal primer

<400> SEQUENCE: 2
cccaaggttc aactacgagc tt                                     22

<210> SEQ ID NO 3
<211> LENGTH: 22
<212> TYPE: DNA
<213> ORGANISM: Artificial
<220> FEATURE:
<223> OTHER INFORMATION: Pan fungal primer

<400> SEQUENCE: 3
aacgaaagtt aggggatcga ag                                     22

```
<210> SEQ ID NO 4
<211> LENGTH: 21
<212> TYPE: DNA
<213> ORGANISM: Artificial
<220> FEATURE:
<223> OTHER INFORMATION: Pan fungal primer

<400> SEQUENCE: 4
ctttaagttt cagccttgcg a                                          21

<210> SEQ ID NO 5
<211> LENGTH: 33
<212> TYPE: DNA
<213> ORGANISM: Artificial
<220> FEATURE:
<223> OTHER INFORMATION: Pan fungal probe

<400> SEQUENCE: 5
ccgagccgta gtcttaacca taaactatgc gct                             33

<210> SEQ ID NO 6
<211> LENGTH: 19
<212> TYPE: DNA
<213> ORGANISM: Artificial
<220> FEATURE:
<223> OTHER INFORMATION: Pan bacterial primer

<400> SEQUENCE: 6
agagtttgat cctggctag                                             19

<210> SEQ ID NO 7
<211> LENGTH: 20
<212> TYPE: DNA
<213> ORGANISM: Artificial
<220> FEATURE:
<223> OTHER INFORMATION: Pan bacterial primer

<400> SEQUENCE: 7
taaggttctt cgcgttgctt                                            20
```